(12) United States Patent
Kurokawa et al.

(10) Patent No.: US 9,102,971 B2
(45) Date of Patent: Aug. 11, 2015

(54) PROCESS FOR PRODUCTION OF PROTEIN

(75) Inventors: Megumi Kurokawa, Gunma (JP);
Keina Yamaguchi, Gunma (JP); Risa Ogawa, Gunma (JP); Masayoshi Tsukahara, Gunma (JP); Koichi Kawakami, Shizuoka (JP); Yoko Hayashi, Gunma (JP)

(73) Assignees: Inter-University Research Institute Corporation Research Organization of Information and Systems, Tokyo (JP);
KYOWA HAKKO KIRIN CO., LTD, Tokyo (JP)

( * ) Notice: Subject to any disclaimer, the term of this patent is extended or adjusted under 35 U.S.C. 154(b) by 16 days.

(21) Appl. No.: 13/326,873

(22) Filed: Dec. 15, 2011

(65) Prior Publication Data

US 2012/0196327 A1   Aug. 2, 2012

(30) Foreign Application Priority Data

Dec. 15, 2010 (JP) ................. 2010-279849

(51) Int. Cl.
| | |
|---|---|
| C12P 21/00 | (2006.01) |
| C12N 15/85 | (2006.01) |
| C12N 5/10 | (2006.01) |
| C12P 21/02 | (2006.01) |
| C07K 16/10 | (2006.01) |
| C07K 16/24 | (2006.01) |
| C07K 16/28 | (2006.01) |

(52) U.S. Cl.
CPC ............. *C12P 21/02* (2013.01); *C07K 16/1018* (2013.01); *C07K 16/241* (2013.01); *C07K 16/2887* (2013.01); *C07K 16/2896* (2013.01); *C12N 15/85* (2013.01); *C07K 2317/14* (2013.01); *C12N 2800/107* (2013.01); *C12N 2800/90* (2013.01)

(58) Field of Classification Search
None
See application file for complete search history.

(56) References Cited

U.S. PATENT DOCUMENTS

| | | | |
|---|---|---|---|
| 7,737,325 B2* | 6/2010 | Kanda et al. ............... | 800/14 |
| 2003/0037346 A1 | 2/2003 | Craig et al. | |
| 2004/0242512 A1 | 12/2004 | Misawa et al. | |
| 2006/0141627 A1* | 6/2006 | Comer ....................... | 435/472 |
| 2010/0129914 A1 | 5/2010 | Koga et al. | |
| 2010/0311116 A1 | 12/2010 | Wurm et al. | |
| 2011/0045532 A1 | 2/2011 | Kawakami et al. | |

FOREIGN PATENT DOCUMENTS

| | | |
|---|---|---|
| EP | 1 484 395 A1 | 12/2004 |
| JP | 2003-512051 T | 4/2003 |
| JP | 2003235575 A2 * | 8/2003 |
| WO | 00/65042 A1 | 11/2000 |
| WO | 01/29204 A2 | 4/2001 |
| WO | 2004/009792 A2 | 1/2004 |
| WO | 2007/082164 A2 | 7/2007 |
| WO | 2008-072540 A1 | 6/2008 |
| WO | 2010/036976 A2 | 4/2010 |

OTHER PUBLICATIONS

Lattenmayer et al. (Biotechnology and Bioengineering, vol. 96, No. 6, Apr. 15, 2007).*
Poche et al. (Mol Gen Genet. Sep. 1979;175(2):181-5., Abstract only).*
Urusaki et al. (Genetics 174 (2), 639-649 (2006)).*
Sumiyama, et al., "New methods for mouse transgenesis with the Tol2 transposable element", Division of Population Genetics, National Institute of Genetics/Division of Molecular and Development Biology, vol. 28, No. 16, 2010, pp. 2653-2660.
Yagita, et al., "Real-time monitoring of circadian clock oscillations in primary cultures of mammalian cells using Tol2 transposon-mediated gene transfer strategy", Methodology Article, BMC Biotechnology, 2010, pp. 1-7.
Urasaki, et al., "Functional Dissection of the Tol2 Transposable Element Identified the Minimal *cis*-Sequence and a Highly repetitive Sequence on the Subterminal region Essential for Transposition", Genetics Society of America, Aug. 4, 2006, pp. 639-649.
Ahkihiko Koga; et al.; "Transposable element in fish"; Scientific Correspondence; Nature; vol. 383; Sep. 5, 1996; one (1) page total.
Zoltan Ivics; et al.; " Molecular Reconstruction of Sleeping Beauty, a Tc1-like Transposon from Fish, and Its Transposition in Human Cells"; Cell Press, Nov. 14, 1997, vol. 91, pp. 501-510.
Csaba Miskey, et al.; "The Frog Prince: a reconstructed transposon from *Rana pipiens* with high transpositional activity in vertebrate cells"; Nucleic Acids Research; 2003; vol. 31 No. 23; pp. 6873 to 6881.
M. J. Fraser; et al.; "Precise excision of TTAA-soecific lepidopteran transposons piggyBac (IFP2) and tagalong (TFP3) from baculovirus genome in cell lines from two species of Lepidoptera"; Insect Molecular Biology; 1996; vol. 5 No. 2; pp. 141-151.
Koichi Kawakami, et al.; "Transposition of the Tol@ Element, an Ac-Like Element from the Japanese Medaka Fish *Oryzias* Laptipes, in Mouse Embryonic Stem Cells", Genetics Society of America; 2004; vol. 166; pp. 895-899.
Darius Balciuanas; "Harnessing a High Cargo-Capacity Transposon for Genetic Applications in Vertebrates"; PLoS Genetics; Nov. 2006; vol. 2 Issue 11; pp. 1715-1724.
Guangbin Luo; et al.; "Chromosomal transposition of a Tcl/mariner-like element in mouse embryonic stem cells"; Proc. Nat'l Acad. Sci (PNAS); USA; Sep. 1998; vol. 95; pp. 10769-10773.
Sylvia E J. Fischer; et al.; "Regulated transposition of a fish transposon in the mouse germ line"; PNAS; Jun. 2001; vol. 98 No. 12; pp. 6759-6764.

(Continued)

*Primary Examiner* — Suzanne M Noakes
*Assistant Examiner* — Jae W Lee
(74) *Attorney, Agent, or Firm* — Sughrue Mion, PLLC

(57) ABSTRACT

The present invention relates to a method for integrating a gene fragment inserted between a pair of transposon sequences into a chromosome of a mammalian cell, comprising introducing at least one expression vector which comprises a gene fragment comprising a DNA encoding a protein of interest and also comprises a pair of transposon sequences at both terminals of the gene fragment, into a suspension mammalian cell; and a method for producing the protein of interest comprising suspension-culturing a suspension mammalian cell which produces the protein of interest; and an a suspension mammalian cell which expresses the protein of interest.

9 Claims, 13 Drawing Sheets

(56) References Cited

OTHER PUBLICATIONS

Adam Dupuy; "Mammalian mutagenesis using a highly mobile somatic Sleeping Beauty transposon system"; Nature Publishing Group; Jul. 2005; vol. 436 No. 14; pp. 221-226.

Juan Cadinanos; et al.; "Generation of an inducible and optimized piggyBac transposon system"; Nucleic Acids Research 2007; vol. 35 No. 12; 8 pp. total.

Sareina Chiung-Yuan Wu; et al.'; "piggyBac is a flexible and highly active transposon as compared to Sleeping Beauty, tol2, and Mos1, in mammalian cells"; PNAS; Oct. 2006; vol. 103 No. 41; pp. 15008 to 15013.

Christine Lattenmayer, et al.; "Protein-Free Transfection of CHO Host Cells With an IgG-Fusion Protein: Selection and Characterization of Stable High Producers and Comparison to Conventionally Transfected Clones"; Biotechnology and Bioengineering; Apr. 2007; vol. 96 No. 6; pp. 1118-1126.

Florian M. Wurm; "Production of recombinant protein therapeutics in cultivated mammalian cells"; Nature Biotechnology; Nov. 2004; vol. 22 No. 11; pp. 1393-1398.

Louise M. Barnes, et al.; "Molecular Analysis of Successful Cell Line Selection in Transfected GS-NSO Myeloma Cells"; Biotechnology and Bioengineering; 2007; vol. 96 No. 2; pp. 337-348.

Allison A. Bianchi, et al.; "High-Level Expression of Full-length Antibodies Using Trans-Complementing Expression Vectors"; Biotechnology and Bioengineering;Nov. 2003; vol. 84, No. 4, pp. 439-444.

U.S. Patent and Trademark Office, Non-Final Office Action dated Oct. 16, 2012, issued in co-pending U.S. Appl. No. 12/813,920.

U.S. Patent and Trademark Office, Final Office Action dated Mar. 26, 2013, issued in co-pending U.S. Appl. No. 12/813,920.

U.S. Patent and Trademark Office, Election of Species Requirement dated Jul. 19, 2012, issued in co-pending U.S. Appl. No. 12/813,920.

"Amendment Under 37 C.F.R. § 1.11," submitted to U.S. Patent and Trademark Office on Jan. 16, 2013, in co-pending U.S. Appl. No. 12/813,920; pp. 1-21.

"Amendment Under 37 C.F.R. § 1.114(c)," submitted to U.S. Patent and Trademark Office on Jun. 26, 2013, in co-pending U.S. Appl. No. 12/813,920; pp. 1-15.

"Response to Election of Species Requirement," submitted to the U.S. Patent and Trademark Office on Aug. 16, 2012, in co-pending U.S. Appl. No. 12/813,920; pp. 1-2.

European Patent Office, Communication dated Apr. 25, 2014, issued in corresponding European Patent Application No. 11848424.5.

* cited by examiner

SEQUENCE LISTING

```
<160> NUMBER OF SEQ ID NOS: 60

<210> SEQ ID NO 1
<211> LENGTH: 2788
<212> TYPE: DNA
<213> ORGANISM: Artificial Sequence
<220> FEATURE:
<223> OTHER INFORMATION: Synthetic nonautologus Tol2 transposon

<400> SEQUENCE: 1
cagaggtgta aagtacttga gtaattttac ttgattactg tacttaagta ttatttttgg      60 ggattttac  tttacttgag tacaattaaa aatcaatact tttactttta cttaattaca     120
tttttttaga aaaaaaagta ctttttactc cttacaattt tatttacagt caaaaagtac     180
ttattttttg gagatcactt cattctattt tcccttgcta ttaccaaacc aattgaattg     240
cgctgatgcc cagtttaatt taaatgttat ttattctgcc tatgaaaatc gttttcacat     300
tatatgaaat tggtcagaca tgttcattgg tcctttggaa gtgacgtcat gtcacatcta     360
ttaccacaat gcacagcacc ttgacctgga aattagggaa attataacag tcaatcagtg     420
gaagaaaatg gaggaagtat gtgattcatc agcagctgcg agcagcacag tccaaaatca     480
gccacaggat caagagcacc cgtggccgta tcttcgcgaa ttcttttctt taagtggtgt     540
```

| | |
|---|---|
| aaataaagat tcattcaaga tgaaatgtgt cctctgtctc ccgcttaata agaaatatc | 600 |
| ggccttcaaa agttcgccat caaacctaag gaagcatatt gaggtaagta cattaagtat | 660 |
| tttgttttac tgatagtttt tttttttttt tttttttttt tttttgggtg tgcatgtttt | 720 |
| gacgttgatg gcgcgccttt tatatgtgta gtaggcctat tttcactaat gcatgcgatt | 780 |
| gacaatataa ggctcacgta ataaaatgct aaaatgcatt tgtaattggt aacgttaggt | 840 |
| ccacgggaaa tttggcgcct attgcagctt tgaataatca ttatcattcc gtgctctcat | 900 |
| tgtgtttgaa ttcatgcaaa acacaagaaa accaagcgag aaattttttt ccaaacatgt | 960 |
| tgtattgtca aaacggtaac actttacaat gaggttgatt agttcatgta ttaactaaca | 1020 |
| ttaaataacc atgagcaata catttgttac tgtatctgtt aatctttgtt aacgttagtt | 1080 |
| aatagaaata cagatgttca ttgtttgttc atgttagttc acagtgcatt aactaatgtt | 1140 |
| aacaagatat aaagtattag taaatgttga aattaacatg tatacgtgca gttcattatt | 1200 |
| agttcatgtt aactaatgta gttaactaac gaaccttatt gtaaaagtgt taccatcaaa | 1260 |
| actaatgtaa tgaaatcaat tcaccctgtc atgtcagcct tacagtcctg tgttttgtc | 1320 |
| aatataatca gaaataaaat taatgtttga ttgtcactaa atgctactgt atttctaaaa | 1380 |
| tcaacaagta tttaacatta taaagtgtgc aattggctgc aaatgtcagt tttattaaag | 1440 |
| ggttagttca cccaaaaatg aaaataatgt cattaatgac tcgccctcat gtcgttccaa | 1500 |
| gcccgtaaga cctccgttca tcttcagaac acagtttaag atattttaga tttagtccga | 1560 |
| gagctttctg tgcctccatt gagaatgtat gtacggtata ctgtccatgt ccagaaaggt | 1620 |
| aataaaaaca tcaaagtagt ccatgtgaca tcagtgggtt agttagaatt ttttgaagca | 1680 |
| tcgaatacat tttggtccaa aaataacaaa acctacgact ttattcggca ttgtattctc | 1740 |
| ttccgggtct gttgtcaatc cgcgttcacg acttcgcagt gacgctacaa tgctgaataa | 1800 |
| agtcgtaggt tttgttattt ttggaccaaa atgtatttc gatgcttcaa ataattctac | 1860 |
| ctaacccact gatgtcacat ggactacttt gatgttttta ttacctttct ggacatggac | 1920 |
| agtataccgt acatacattt tcagtggagg gacagaaagc tctcggacta aatctaaaat | 1980 |
| atcttaaact gtgttccgaa gatgaacgga ggtgttacgg gcttggaacg acatgagggt | 2040 |
| gagtcattaa tgacatcttt tcattttgg gtgaactaac cctttaatgc tgtaatcaga | 2100 |
| gagtgtatgt gtaattgtta catttattgc atacaatata aatatttatt tgttgttttt | 2160 |
| acagagaatg cacccaaatt acctcaaaaa ctactctaaa ttgacagcac agaagagaaa | 2220 |
| gatcgggaca gatctcatat gctcgagggc ccatctggcc tgtgtttcag acaccaggga | 2280 |
| gtctctgctc acgtttcctg ctatttgcag cctctctatc aagactaata cacctcttcc | 2340 |
| cgcatcggct gcctgtgaga ggcttttcag cactgcagga ttgcttttca gccccaaaag | 2400 |
| agctaggctt gacactaaca attttgagaa tcagcttcta ctgaagttaa atctgaggtt | 2460 |
| ttacaacttt gagtagcgtg tactggcatt agattgtctg tcttatagtt tgataattaa | 2520 |
| atacaaacag ttctaaagca ggataaaacc ttgtatgcat ttcatttaat gttttttgag | 2580 |
| attaaaagct taaacaagaa tctctagttt tctttcttgc ttttacttt acttccttaa | 2640 |
| tactcaagta caattttaat ggagtacttt tttactttta ctcaagtaag attctagcca | 2700 |
| gatactttta cttttaattg agtaaaattt tccctaagta cttgtacttt cacttgagta | 2760 |
| aaattttga gtacttttta cacctctg | 2788 |

<210> SEQ ID NO 2
<211> LENGTH: 200

```
<212> TYPE: DNA
<213> ORGANISM: Artificial Sequence
<220> FEATURE:
<223> OTHER INFORMATION: Synthetic Tol2-L transposon sequence

<400> SEQUENCE: 2
cagaggtgta aagtacttga gtaattttac ttgattactg tacttaagta ttattttttgg    60 ggattttttac tttacttgag tacaattaaa aatcaatact tttacttttta cttaattaca  120 tttttttaga aaaaaagta cttttttactc cttacaattt tatttacagt caaaaagtac   180
ttattttttg gagatcactt                                               200

<210> SEQ ID NO 3
<211> LENGTH: 504
<212> TYPE: DNA
<213> ORGANISM: Artificial Sequence
<220> FEATURE:
<223> OTHER INFORMATION: Synthetic Tol2-R transposon sequence

<400> SEQUENCE: 3
ctgctcacgt ttcctgctat ttgcagcctc tctatcaaga ctaatacacc tcttcccgca    60
tcggctgcct gtgagaggct tttcagcact gcaggattgc ttttcagccc caaaagagct  120
aggcttgaca ctaacaattt tgagaatcag cttctactga agttaaatct gaggttttac  180
aactttgagt agcgtgtact ggcattagat tgtctgtctt atagtttgat aattaaatac   240
aaacagttct aaagcaggat aaaaccttgt atgcatttca tttaatgttt tttgagatta  300
aaagcttaaa caagaatctc tagttttctt tcttgctttt actttttactt ccttaatact  360 caagtacaat tttaatggag tactttttta cttttactca agtaagattc tagccagata  420
cttttacttt taattgagta aaattttccc taagtacttg tactttcact tgagtaaaat  480
ttttgagtac ttttttacacc tctg                                         504

<210> SEQ ID NO 4
<211> LENGTH: 2156
<212> TYPE: DNA
<213> ORGANISM: Oryzias latipes
<220> FEATURE:
<221> NAME/KEY: CDS
<222> LOCATION: (85)..(2034)

<400> SEQUENCE: 4
acgtcatgtc acatctatta ccacaatgca cagcaccttg acctggaaat tagggaaatt      60
ataacagtca atcagtggaa gaaa atg gag gaa gta tgt gat tca tca gca        111
                          Met Glu Glu Val Cys Asp Ser Ser Ala
                            1               5 gct gcg agc agc aca gtc caa aat cag cca cag gat caa gag cac ccg       159
Ala Ala Ser Ser Thr Val Gln Asn Gln Pro Gln Asp Gln Glu His Pro
 10               15                  20                  25 tgg ccg tat ctt cgc gaa ttc ttt tct tta agt ggt gta aat aaa gat       207
Trp Pro Tyr Leu Arg Glu Phe Phe Ser Leu Ser Gly Val Asn Lys Asp
                30                  35                  40 tca ttc aag atg aaa tgt gtc ctc tgt ctc ccg ctt aat aaa gaa ata       255
Ser Phe Lys Met Lys Cys Val Leu Cys Leu Pro Leu Asn Lys Glu Ile
        45                  50                  55 tcg gcc ttc aaa agt tcg cca tca aac cta agg aag cat att gag aga       303
Ser Ala Phe Lys Ser Ser Pro Ser Asn Leu Arg Lys His Ile Glu Arg
    60                  65                  70 atg cac cca aat tac ctc aaa aac tac tct aaa ttg aca gca cag aag       351
Met His Pro Asn Tyr Leu Lys Asn Tyr Ser Lys Leu Thr Ala Gln Lys
75                  80                  85
```

-continued

| | | |
|---|---|---|
| aga aag atc ggg acc tcc acc cat gct tcc agc agt aag caa ctg aaa<br>Arg Lys Ile Gly Thr Ser Thr His Ala Ser Ser Ser Lys Gln Leu Lys<br>90                                    95                                100                          105 | 399 | |
| gtt gac tca gtt ttc cca gtc aaa cat gtg tct cca gtc act gtg aac<br>Val Asp Ser Val Phe Pro Val Lys His Val Ser Pro Val Thr Val Asn<br>                   110                            115                            120 | 447 | |
| aaa gct ata tta agg tac atc att caa gga ctt cat cct ttc agc act<br>Lys Ala Ile Leu Arg Tyr Ile Ile Gln Gly Leu His Pro Phe Ser Thr<br>         125                                130                                135 | 495 | |
| gtt gat ctg cca tca ttt aaa gag ctg att agt aca ctg cag cct ggc<br>Val Asp Leu Pro Ser Phe Lys Glu Leu Ile Ser Thr Leu Gln Pro Gly<br>140                                    145                                150 | 543 | |
| att tct gtc att aca agg cct act tta cgc tcc aag ata gct gaa gct<br>Ile Ser Val Ile Thr Arg Pro Thr Leu Arg Ser Lys Ile Ala Glu Ala<br>         155                                160                            165 | 591 | |
| gct ctg atc atg aaa cag aaa gtg act gct gcc atg agt gaa gtt gaa<br>Ala Leu Ile Met Lys Gln Lys Val Thr Ala Ala Met Ser Glu Val Glu<br>170                                  175                            180                          185 | 639 | |
| tgg att gca acc aca acg gat tgt tgg act gca cgt aga aag tca ttc<br>Trp Ile Ala Thr Thr Thr Asp Cys Trp Thr Ala Arg Arg Lys Ser Phe<br>                   190                            195                            200 | 687 | |
| att ggt gta act gct cac tgg atc aac cct gga agt ctt gaa aga cat<br>Ile Gly Val Thr Ala His Trp Ile Asn Pro Gly Ser Leu Glu Arg His<br>         205                                210                                215 | 735 | |
| tcc gct gca ctt gcc tgc aaa aga tta atg ggc tct cat act ttt gag<br>Ser Ala Ala Leu Ala Cys Lys Arg Leu Met Gly Ser His Thr Phe Glu<br>220                                  225                            230 | 783 | |
| gta ctg gcc agt gcc atg aat gat atc cac tca gag tat gaa ata cgt<br>Val Leu Ala Ser Ala Met Asn Asp Ile His Ser Glu Tyr Glu Ile Arg<br>         235                                240                            245 | 831 | |
| gac aag gtt gtt tgc aca acc aca gac agt ggt tcc aac ttt atg aag<br>Asp Lys Val Val Cys Thr Thr Thr Asp Ser Gly Ser Asn Phe Met Lys<br>250                                  255                            260                          265 | 879 | |
| gct ttc aga gtt ttt ggt gtg gaa aac aat gat atc gag act gag gca<br>Ala Phe Arg Val Phe Gly Val Glu Asn Asn Asp Ile Glu Thr Glu Ala<br>                   270                            275                            280 | 927 | |
| aga agg tgt gaa agt gat gac act gat tct gaa ggc tgt ggt gag gga<br>Arg Arg Cys Glu Ser Asp Asp Thr Asp Ser Glu Gly Cys Gly Glu Gly<br>         285                                290                                295 | 975 | |
| agt gat ggt gtg gaa ttc caa gat gcc tca cga gtc ctg gac caa gac<br>Ser Asp Gly Val Glu Phe Gln Asp Ala Ser Arg Val Leu Asp Gln Asp<br>300                                  305                            310 | 1023 | |
| gat ggc ttc gaa ttc cag cta cca aaa cat caa aag tgt gcc tgt cac<br>Asp Gly Phe Glu Phe Gln Leu Pro Lys His Gln Lys Cys Ala Cys His<br>         315                                320                            325 | 1071 | |
| tta ctt aac cta gtc tca agc gtt gat gcc caa aaa gct ctc tca aat<br>Leu Leu Asn Leu Val Ser Ser Val Asp Ala Gln Lys Ala Leu Ser Asn<br>330                                  335                            340                          345 | 1119 | |
| gaa cac tac aag aaa ctc tac aga tct gtc ttt ggc aaa tgc caa gct<br>Glu His Tyr Lys Lys Leu Tyr Arg Ser Val Phe Gly Lys Cys Gln Ala<br>                   350                            355                            360 | 1167 | |
| tta tgg aat aaa agc agc cga tcg gct cta gca gct gaa gct gtt gaa<br>Leu Trp Asn Lys Ser Ser Arg Ser Ala Leu Ala Ala Glu Ala Val Glu<br>         365                                370                            375 | 1215 | |
| tca gaa agc cgg ctt cag ctt tta agg cca aac caa acg cgg tgg aat<br>Ser Glu Ser Arg Leu Gln Leu Leu Arg Pro Asn Gln Thr Arg Trp Asn<br>380                                  385                            390 | 1263 | |
| tca act ttt atg gct gtt gac aga att ctt caa att tgc aaa gaa gca<br>Ser Thr Phe Met Ala Val Asp Arg Ile Leu Gln Ile Cys Lys Glu Ala | 1311 | |

```
                 395                 400                 405
gga gaa ggc gca ctt cgg aat ata tgc acc tct ctt gag gtt cca atg       1359
Gly Glu Gly Ala Leu Arg Asn Ile Cys Thr Ser Leu Glu Val Pro Met
410                 415                 420                 425 ttt aat cca gca gaa atg ctg ttc ttg aca gag tgg gcc aac aca atg       1407
Phe Asn Pro Ala Glu Met Leu Phe Leu Thr Glu Trp Ala Asn Thr Met
                430                 435                 440 cgt cca gtt gca aaa gta ctc gac atc ttg caa gcg gaa acg aat aca       1455
Arg Pro Val Ala Lys Val Leu Asp Ile Leu Gln Ala Glu Thr Asn Thr
            445                 450                 455 cag ctg ggg tgg ctg ctg cct agt gtc cat cag tta agc ttg aaa ctt       1503
Gln Leu Gly Trp Leu Leu Pro Ser Val His Gln Leu Ser Leu Lys Leu
        460                 465                 470 cag cga ctc cac cat tct ctc agg tac tgt gac cca ctt gtg gat gcc       1551
Gln Arg Leu His His Ser Leu Arg Tyr Cys Asp Pro Leu Val Asp Ala
    475                 480                 485 cta caa caa gga atc caa aca cga ttc aag cat atg ttt gaa gat cct       1599
Leu Gln Gln Gly Ile Gln Thr Arg Phe Lys His Met Phe Glu Asp Pro
490                 495                 500                 505 gag atc ata gca gct gcc atc ctt ctc cct aaa ttt cgg acc tct tgg       1647
Glu Ile Ile Ala Ala Ala Ile Leu Leu Pro Lys Phe Arg Thr Ser Trp
                510                 515                 520 aca aat gat gaa acc atc ata aaa cga ggc atg gac tac atc aga gtg       1695
Thr Asn Asp Glu Thr Ile Ile Lys Arg Gly Met Asp Tyr Ile Arg Val
            525                 530                 535 cat ctg gag cct ttg gac cac aag aag gaa ttg gcc aac agt tca tct       1743
His Leu Glu Pro Leu Asp His Lys Lys Glu Leu Ala Asn Ser Ser Ser
        540                 545                 550 gat gat gaa gat ttt ttc gct tct ttg aaa ccg aca aca cat gaa gcc       1791
Asp Asp Glu Asp Phe Phe Ala Ser Leu Lys Pro Thr Thr His Glu Ala
    555                 560                 565 agc aaa gag ttg gat gga tat ctg gcc tgt gtt tca gac acc agg gag       1839
Ser Lys Glu Leu Asp Gly Tyr Leu Ala Cys Val Ser Asp Thr Arg Glu
570                 575                 580                 585 tct ctg ctc acg ttt cct gct att tgc agc ctc tct atc aag act aat       1887
Ser Leu Leu Thr Phe Pro Ala Ile Cys Ser Leu Ser Ile Lys Thr Asn
                590                 595                 600 aca cct ctt ccc gca tcg gct gcc tgt gag agg ctt ttc agc act gca       1935
Thr Pro Leu Pro Ala Ser Ala Ala Cys Glu Arg Leu Phe Ser Thr Ala
            605                 610                 615 gga ttg ctt ttc agc ccc aaa aga gct agg ctt gac act aac aat ttt       1983
Gly Leu Leu Phe Ser Pro Lys Arg Ala Arg Leu Asp Thr Asn Asn Phe
        620                 625                 630 gag aat cag ctt cta ctg aag tta aat ctg agg ttt tac aac ttt gag       2031
Glu Asn Gln Leu Leu Leu Lys Leu Asn Leu Arg Phe Tyr Asn Phe Glu
    635                 640                 645 tag cgtgtactgg cattagattg tctgtcttat agtttgataa ttaaatacaa            2084
acagttctaa agcaggataa aaccttgtat gcatttcatt taatgttttt tgagattaaa     2144
agcttaaaca ag                                                         2156

<210> SEQ ID NO 5
<211> LENGTH: 649
<212> TYPE: PRT
<213> ORGANISM: Oryzias latipes

<400> SEQUENCE: 5

Met Glu Glu Val Cys Asp Ser Ser Ala Ala Ser Ser Thr Val Gln
1               5                   10                  15
```

Asn Gln Pro Gln Asp Gln Glu His Pro Trp Pro Tyr Leu Arg Glu Phe
            20                  25                  30

Phe Ser Leu Ser Gly Val Asn Lys Asp Ser Phe Lys Met Lys Cys Val
        35                  40                  45

Leu Cys Leu Pro Leu Asn Lys Glu Ile Ser Ala Phe Lys Ser Ser Pro
    50                  55                  60

Ser Asn Leu Arg Lys His Ile Glu Arg Met His Pro Asn Tyr Leu Lys
65                  70                  75                  80

Asn Tyr Ser Lys Leu Thr Ala Gln Lys Arg Lys Ile Gly Thr Ser Thr
                85                  90                  95

His Ala Ser Ser Ser Lys Gln Leu Lys Val Asp Ser Val Phe Pro Val
            100                 105                 110

Lys His Val Ser Pro Val Thr Val Asn Lys Ala Ile Leu Arg Tyr Ile
        115                 120                 125

Ile Gln Gly Leu His Pro Phe Ser Thr Val Asp Leu Pro Ser Phe Lys
    130                 135                 140

Glu Leu Ile Ser Thr Leu Gln Pro Gly Ile Ser Val Ile Thr Arg Pro
145                 150                 155                 160

Thr Leu Arg Ser Lys Ile Ala Glu Ala Ala Leu Ile Met Lys Gln Lys
                165                 170                 175

Val Thr Ala Ala Met Ser Glu Val Glu Trp Ile Ala Thr Thr Thr Asp
            180                 185                 190

Cys Trp Thr Ala Arg Arg Lys Ser Phe Ile Gly Val Thr Ala His Trp
        195                 200                 205

Ile Asn Pro Gly Ser Leu Glu Arg His Ser Ala Ala Leu Ala Cys Lys
    210                 215                 220

Arg Leu Met Gly Ser His Thr Phe Glu Val Leu Ala Ser Ala Met Asn
225                 230                 235                 240

Asp Ile His Ser Glu Tyr Glu Ile Arg Asp Lys Val Val Cys Thr Thr
                245                 250                 255

Thr Asp Ser Gly Ser Asn Phe Met Lys Ala Phe Arg Val Phe Gly Val
            260                 265                 270

Glu Asn Asn Asp Ile Glu Thr Glu Ala Arg Arg Cys Glu Ser Asp Asp
        275                 280                 285

Thr Asp Ser Glu Gly Cys Gly Glu Gly Ser Asp Gly Val Glu Phe Gln
    290                 295                 300

Asp Ala Ser Arg Val Leu Asp Gln Asp Asp Gly Phe Glu Phe Gln Leu
305                 310                 315                 320

Pro Lys His Gln Lys Cys Ala Cys His Leu Leu Asn Leu Val Ser Ser
                325                 330                 335

Val Asp Ala Gln Lys Ala Leu Ser Asn Glu His Tyr Lys Lys Leu Tyr
            340                 345                 350

Arg Ser Val Phe Gly Lys Cys Gln Ala Leu Trp Asn Lys Ser Ser Arg
        355                 360                 365

Ser Ala Leu Ala Ala Glu Ala Val Glu Ser Ser Arg Leu Gln Leu
    370                 375                 380

Leu Arg Pro Asn Gln Thr Arg Trp Asn Ser Thr Phe Met Ala Val Asp
385                 390                 395                 400

Arg Ile Leu Gln Ile Cys Lys Glu Ala Gly Gly Ala Leu Arg Asn
                405                 410                 415

Ile Cys Thr Ser Leu Glu Val Pro Met Phe Asn Pro Ala Glu Met Leu
            420                 425                 430

Phe Leu Thr Glu Trp Ala Asn Thr Met Arg Pro Val Ala Lys Val Leu

```
              435                 440                 445
Asp Ile Leu Gln Ala Glu Thr Asn Thr Gln Leu Gly Trp Leu Leu Pro
450                 455                 460

Ser Val His Gln Leu Ser Leu Lys Leu Gln Arg Leu His His Ser Leu
465                 470                 475                 480

Arg Tyr Cys Asp Pro Leu Val Asp Ala Leu Gln Gln Gly Ile Gln Thr
                485                 490                 495

Arg Phe Lys His Met Phe Glu Asp Pro Glu Ile Ile Ala Ala Ala Ile
                500                 505                 510

Leu Leu Pro Lys Phe Arg Thr Ser Trp Thr Asn Asp Glu Thr Ile Ile
                515                 520                 525

Lys Arg Gly Met Asp Tyr Ile Arg Val His Leu Glu Pro Leu Asp His
530                 535                 540

Lys Lys Glu Leu Ala Asn Ser Ser Ser Asp Asp Glu Asp Phe Phe Ala
545                 550                 555                 560

Ser Leu Lys Pro Thr Thr His Glu Ala Ser Lys Glu Leu Asp Gly Tyr
                565                 570                 575

Leu Ala Cys Val Ser Asp Thr Arg Glu Ser Leu Leu Thr Phe Pro Ala
                580                 585                 590

Ile Cys Ser Leu Ser Ile Lys Thr Asn Thr Pro Leu Pro Ala Ser Ala
                595                 600                 605

Ala Cys Glu Arg Leu Phe Ser Thr Ala Gly Leu Leu Phe Ser Pro Lys
610                 615                 620

Arg Ala Arg Leu Asp Thr Asn Asn Phe Glu Asn Gln Leu Leu Leu Lys
625                 630                 635                 640

Leu Asn Leu Arg Phe Tyr Asn Phe Glu
                645

<210> SEQ ID NO 6
<211> LENGTH: 4682
<212> TYPE: DNA
<213> ORGANISM: Oryzias latipes

<400> SEQUENCE: 6
cagaggtgta aagtacttga gtaattttac ttgattactg tacttaagta ttatttttgg      60 ggattttttac tttacttgag tacaattaaa aatcaatact tttactttta cttaattaca    120 ttttttttaga aaaaaagta cttttttactc cttacaattt tatttacagt caaaagtac    180 ttatttttg gagatcactt cattctattt tcccttgcta ttaccaaacc aattgaattg      240
cgctgatgcc cagtttaatt taaatgttat ttattctgcc tatgaaaatc gttttcacat     300
tatatgaaat tggtcagaca tgttcattgg tcctttggaa gtgacgtcat gtcacatcta     360
ttaccacaat gcacagcacc ttgacctgga aattagggaa attataacag tcaatcagtg    420
gaagaaaatg gaggaagtat gtgattcatc agcagctgcg agcagcacag tccaaaatca    480
gccacaggat caagagcacc cgtggccgta tcttcgcgaa ttctttttct taagtggtgt     540
aaataaagat tcattcaaga tgaaatgtgt cctctgtctc ccgcttaata agaaatatc      600 ggccttcaaa agttcgccat caaacctaag gaagcatatt gaggtaagta cattaagtat     660
tttgttttac tgatagtttt ttttttttt tttttttttt ttttttgggtg tgcatgtttt     720 gacgttgatg gcgcgccttt tatatgtgta gtaggcctat tttcactaat gcatgcgatt     780
gacaatataa ggctcacgta ataaaatgct aaaatgcatt tgtaattggt aacgttaggt     840
ccacgggaaa tttggcgcct attgcagctt tgaataatca ttatcattcc gtgctctcat     900
```

```
tgtgtttgaa ttcatgcaaa acacaagaaa accaagcgag aaattttttt ccaaacatgt    960
tgtattgtca aaacggtaac actttacaat gaggttgatt agttcatgta ttaactaaca   1020
ttaaataacc atgagcaata catttgttac tgtatctgtt aatctttgtt aacgttagtt   1080
aatagaaata cagatgttca ttgtttgttc atgttagttc acagtgcatt aactaatgtt   1140
aacaagatat aaagtattag taaatgttga aattaacatg tatacgtgca gttcattatt   1200
agttcatgtt aactaatgta gttaactaac gaaccttatt gtaaaagtgt taccatcaaa   1260
actaatgtaa tgaaatcaat tcaccctgtc atgtcagcct tacagtcctg tgtttttgtc   1320
aatataatca gaaataaaat taatgtttga ttgtcactaa atgctactgt atttctaaaa   1380
tcaacaagta tttaacatta taaagtgtgc aattggctgc aaatgtcagt tttattaaag   1440
ggttagttca cccaaaaatg aaaataatgt cattaatgac tcgccctcat gtcgttccaa   1500
gcccgtaaga cctccgttca tcttcagaac acagtttaag atattttaga tttagtccga   1560
gagctttctg tgcctccatt gagaatgtat gtacggtata ctgtccatgt ccagaaaggt   1620
aataaaaaca tcaaagtagt ccatgtgaca tcagtggggtt agttagaatt ttttgaagca   1680
tcgaatacat tttggtccaa aaataacaaa acctacgact ttattcggca ttgtattctc   1740
ttccgggtct gttgtcaatc cgcgttcacg acttcgcagt gacgctacaa tgctgaataa   1800
agtcgtaggt tttgttattt ttggaccaaa atgtattttc gatgcttcaa ataattctac   1860
ctaacccact gatgtcacat ggactacttt gatgttttta ttacctttct ggacatggac   1920
agtataccgt acatacattt tcagtggagg gacagaaagc tctcggacta aatctaaaat   1980
atcttaaact gtgttccgaa gatgaacgga ggtgttacgg gcttggaacg acatgagggt   2040
gagtcattaa tgacatcttt tcatttttgg gtgaactaac cctttaatgc tgtaatcaga   2100
gagtgtatgt gtaattgtta catttattgc atacaatata aatatttatt tgttgttttt   2160
acagagaatg cacccaaatt acctcaaaaa ctactctaaa ttgacagcac agaagagaaa   2220
gatcgggacc tccacccatg cttccagcag taagcaactg aaagttgact cagttttccc   2280
agtcaaacat gtgtctccag tcactgtgaa caaagctata ttaaggtaca tcattcaagg   2340
acttcatcct ttcagcactg ttgatctgcc atcatttaaa gagctgatta gtacactgca   2400
gcctggcatt tctgtcatta caaggcctac tttacgctcc aagatagctg aagctgctct   2460
gatcatgaaa cagaaagtga ctgctgccat gagtgaagtt gaatggattg caaccacaac   2520
ggattgttgg actgcacgta gaaagtcatt cattggtgta actgctcact ggatcaaccc   2580
tggaagtctt gaaagacatt ccgctgcact tgcctgcaaa agattaatgg gctctcatac   2640
ttttgaggta ctggccagtg ccatgaatga tatccactca gagtatgaaa tacgtgacaa   2700
ggttgtttgc acaaccacag acagtggttc caactttatg aaggctttca gagttttttgg   2760 tgtggaaaac aatgatatcg agactgaggc aagaaggtgt gaaagtgatg acactgattc   2820
tgaaggctgt ggtgagggaa gtgatggtgt ggaattccaa gatgcctcac gagtcctgga   2880
ccaagacgat ggcttcgaat ccagctacc aaaacatcaa aagtgtgcct gtcacttact   2940
taacctagtc tcaagcgttg atgcccaaaa agctctctca atgaacact acaagaaact   3000 ctacagatct gtctttggca aatgccaagc tttatggaat aaaagcagcc gatcggctct   3060
agcagctgaa gctgttgaat cagaaagccg gcttcagctt taaggccaa accaaacgcg   3120 gtggaattca acttttatgg ctgttgacag aattcttcaa atttgcaaag aagcaggaga   3180
aggcgcactt cggaatatat gcacctctct tgaggttcca atgtaagtgt tttttcccctc   3240 tatcgatgta aacaaatgtg ggttgttttt gtttaatact ctttgattat gctgatttct   3300
```

-continued

```
cctgtaggtt taatccagca gaaatgctgt tcttgacaga gtgggccaac acaatgcgtc    3360
cagttgcaaa agtactcgac atcttgcaag cggaaacgaa tacacagctg ggtggctgc    3420 tgcctagtgt ccatcagtta agcttgaaac ttcagcgact ccaccattct ctcaggtact    3480
gtgacccact tgtggatgcc ctacaacaag gaatccaaac acgattcaag catatgtttg    3540
aagatcctga gatcatagca gctgccatcc ttctccctaa atttcggacc tcttggacaa    3600
atgatgaaac catcataaaa cgaggtaaat gaatgcaagc aacatacact tgacgaattc    3660
taatctgggc aacctttgag ccataccaaa attattcttt tatttattta ttttttgcact    3720 ttttaggaat gttatatccc atctttggct gtgatctcaa tatgaatatt gatgtaaagt    3780
attcttgcag caggttgtag ttatccctca gtgtttcttg aaaccaaact catatgtatc    3840
atatgtggtt tggaaatgca gttagatttt atgctaaaat aagggatttg catgatttta    3900
gatgtagatg actgcacgta aatgtagtta atgacaaaat ccataaaatt tgttcccagt    3960
cagaagcccc tcaaccaaac ttttctttgt gtctgctcac tgtgcttgta ggcatggact    4020
acatcagagt gcatctggag cctttggacc acaagaagga attggccaac agttcatctg    4080
atgatgaaga ttttttcgct tctttgaaac cgacaacaca tgaagccagc aaagagttgg    4140
atggatatct ggcctgtgtt tcagacacca gggagtctct gctcacgttt cctgctattt    4200
gcagcctctc tatcaagact aatacacctc ttcccgcatc ggctgcctgt gagaggcttt    4260
tcagcactgc aggattgctt ttcagcccca aaagagctag gcttgacact aacaattttg    4320
agaatcagct tctactgaag ttaaatctga ggttttacaa ctttgagtag cgtgtactgg    4380
cattagattg tctgtcttat agtttgataa ttaaatacaa acagttctaa agcaggataa    4440
aaccttgtat gcatttcatt taatgttttt tgagattaaa agcttaaaca agaatctcta    4500
gttttctttc ttgcttttac ttttacttcc ttaatactca agtacaattt taatggagta    4560
cttttttact tttactcaag taagattcta gccagatact tttacttttta attgagtaaa    4620 attttcccta agtacttgta ctttcacttg agtaaaattt ttgagtactt tttacaccte    4680 tg                                                                   4682
```

<210> SEQ ID NO 7
<211> LENGTH: 321
<212> TYPE: DNA
<213> ORGANISM: Artificial Sequence
<220> FEATURE:
<223> OTHER INFORMATION: Synthetic Cycloheximide resistant gene
<220> FEATURE:
<221> NAME/KEY: CDS
<222> LOCATION: (1)..(321)

<400> SEQUENCE: 7

```
atg gtc aac gta cct aaa acc cga aga acc ttc tgt aag aag tgt ggc      48
Met Val Asn Val Pro Lys Thr Arg Arg Thr Phe Cys Lys Lys Cys Gly
1               5                   10                  15 aag cat cag cct cac aaa gtg aca cag tat aag aag ggc aag gat tct      96
Lys His Gln Pro His Lys Val Thr Gln Tyr Lys Lys Gly Lys Asp Ser
            20                  25                  30 ttg tat gcc cag gga agg agg cgc tat gat cgg aag cag agt ggc tat     144
Leu Tyr Ala Gln Gly Arg Arg Arg Tyr Asp Arg Lys Gln Ser Gly Tyr
        35                  40                  45 ggt ggg cag aca aag caa att ttc cgg aag aag gct aag acc aca aag     192
Gly Gly Gln Thr Lys Gln Ile Phe Arg Lys Lys Ala Lys Thr Thr Lys
    50                  55                  60 aag att gtg cta agg ctg gaa tgt gtt gag cct aac tgc aga tcc aag     240
Lys Ile Val Leu Arg Leu Glu Cys Val Glu Pro Asn Cys Arg Ser Lys
```

| | | | | | | | | | | | | | | | |
|---|---|---|---|---|---|---|---|---|---|---|---|---|---|---|---|
|Lys|Ile|Val|Leu|Arg|Leu|Glu|Cys|Val|Glu|Pro|Asn|Cys|Arg|Ser|Lys|
|65| | | |70| | | |75| | | |80| | | |

```
agg atg ctg gcc att aag aga tgc aag cat ttt gaa ctg gga gga gat     288
Arg Met Leu Ala Ile Lys Arg Cys Lys His Phe Glu Leu Gly Gly Asp
             85                  90                  95 aag aag aga aag ggc caa gtg atc cag ttc taa                         321
Lys Lys Arg Lys Gly Gln Val Ile Gln Phe
100                 105
```

```
<210> SEQ ID NO 8
<211> LENGTH: 106
<212> TYPE: PRT
<213> ORGANISM: Artificial Sequence
<220> FEATURE:
<223> OTHER INFORMATION: Synthetic Construct

<400> SEQUENCE: 8
```

Met Val Asn Val Pro Lys Thr Arg Arg Thr Phe Cys Lys Lys Cys Gly
1               5                   10                  15

Lys His Gln Pro His Lys Val Thr Gln Tyr Lys Lys Gly Lys Asp Ser
            20                  25                  30

Leu Tyr Ala Gln Gly Arg Arg Arg Tyr Asp Arg Lys Gln Ser Gly Tyr
        35                  40                  45

Gly Gly Gln Thr Lys Gln Ile Phe Arg Lys Lys Ala Lys Thr Thr Lys
    50                  55                  60

Lys Ile Val Leu Arg Leu Glu Cys Val Glu Pro Asn Cys Arg Ser Lys
65                  70                  75                  80

Arg Met Leu Ala Ile Lys Arg Cys Lys His Phe Glu Leu Gly Gly Asp
            85                  90                  95

Lys Lys Arg Lys Gly Gln Val Ile Gln Phe
        100                 105

```
<210> SEQ ID NO 9
<211> LENGTH: 1404
<212> TYPE: DNA
<213> ORGANISM: Artificial Sequence
<220> FEATURE:
<223> OTHER INFORMATION: Synthetic M2Z3 Heavy chain
<220> FEATURE:
<221> NAME/KEY: CDS
<222> LOCATION: (1)..(1404)

<400> SEQUENCE: 9 atg gac tgg acc tgg agc atc ctt ttc ttg gtg gca gca aca ggt         48
Met Asp Trp Thr Trp Ser Ile Leu Phe Leu Val Ala Ala Thr Gly
1               5                   10                  15 gcc cac tcc cag gtt cag ctg gtg cag tct gga gct gag gtg aag aag     96
Ala His Ser Gln Val Gln Leu Val Gln Ser Gly Ala Glu Val Lys Lys
            20                  25                  30 cct ggg gcc tca gtg aag gtc tcc tgc aag gct tct ggt tac acc ttt    144
Pro Gly Ala Ser Val Lys Val Ser Cys Lys Ala Ser Gly Tyr Thr Phe
        35                  40                  45 acc agc tat ggt atc agc tgg gtg cga cag gcc cct gga caa ggg ctt    192
Thr Ser Tyr Gly Ile Ser Trp Val Arg Gln Ala Pro Gly Gln Gly Leu
    50                  55                  60 gag tgg atg gga tgg atc agc gct tac aat ggt aac aca aac tat gca    240
Glu Trp Met Gly Trp Ile Ser Ala Tyr Asn Gly Asn Thr Asn Tyr Ala
65                  70                  75                  80 cag aag ctc cag ggc aga gtc acc atg acc aca gac aca tcc acg agc    288
Gln Lys Leu Gln Gly Arg Val Thr Met Thr Thr Asp Thr Ser Thr Ser
            85                  90                  95
```

| | | |
|---|---|---|
| aca gcc tac atg gag ctg agg agc ctg aga tct gac gac acg gcc gtg<br>Thr Ala Tyr Met Glu Leu Arg Ser Leu Arg Ser Asp Asp Thr Ala Val<br>100                        105                      110 | | 336 |
| tat tac tgt gcg agg gca gca gct ggc gga tac ttc cag cac tgg ggc<br>Tyr Tyr Cys Ala Arg Ala Ala Ala Gly Gly Tyr Phe Gln His Trp Gly<br>         115                      120                      125 | | 384 |
| cag ggc acc ctg gtc acc gtc tcc tca gct agc acc aag ggc cca tcg<br>Gln Gly Thr Leu Val Thr Val Ser Ser Ala Ser Thr Lys Gly Pro Ser<br>130                        135                      140 | | 432 |
| gtc ttc ccc ctg gca ccc tcc tcc aag agc acc tct ggg ggc aca gcg<br>Val Phe Pro Leu Ala Pro Ser Ser Lys Ser Thr Ser Gly Gly Thr Ala<br>145                        150                      155                      160 | | 480 |
| gcc ctg ggc tgc ctg gtc aag gac tac ttc ccc gaa ccg gtg acg gtg<br>Ala Leu Gly Cys Leu Val Lys Asp Tyr Phe Pro Glu Pro Val Thr Val<br>                 165                      170                      175 | | 528 |
| tcg tgg aac tca ggc gcc ctg acc agc ggc gtg cac acc ttc ccg gct<br>Ser Trp Asn Ser Gly Ala Leu Thr Ser Gly Val His Thr Phe Pro Ala<br>             180                      185                      190 | | 576 |
| gtc cta cag tcc tca gga ctc tac tcc ctc agc agc gtg gtg acc gtg<br>Val Leu Gln Ser Ser Gly Leu Tyr Ser Leu Ser Ser Val Val Thr Val<br>                 195                      200                      205 | | 624 |
| ccc tcc agc agc ttg ggc acc cag acc tac atc tgc aac gtg aat cac<br>Pro Ser Ser Ser Leu Gly Thr Gln Thr Tyr Ile Cys Asn Val Asn His<br>210                        215                      220 | | 672 |
| aag ccc agc aac acc aag gtg gac aag aaa gtt gag ccc aaa tct tgt<br>Lys Pro Ser Asn Thr Lys Val Asp Lys Lys Val Glu Pro Lys Ser Cys<br>225                        230                      235                      240 | | 720 |
| gac aaa act cac aca tgc cca ccg tgc cca gca cct gaa ctc ctg ggg<br>Asp Lys Thr His Thr Cys Pro Pro Cys Pro Ala Pro Glu Leu Leu Gly<br>                 245                      250                      255 | | 768 |
| gga ccg tca gtc ttc ctc ttc ccc cca aaa ccc aag gac acc ctc atg<br>Gly Pro Ser Val Phe Leu Phe Pro Pro Lys Pro Lys Asp Thr Leu Met<br>             260                      265                      270 | | 816 |
| atc tcc cgg acc cct gag gtc aca tgc gtg gtg gtg gac gtg agc cac<br>Ile Ser Arg Thr Pro Glu Val Thr Cys Val Val Val Asp Val Ser His<br>                 275                      280                      285 | | 864 |
| gaa gac cct gag gtc aag ttc aac tgg tac gtg gac ggc gtg gag gtg<br>Glu Asp Pro Glu Val Lys Phe Asn Trp Tyr Val Asp Gly Val Glu Val<br>290                        295                      300 | | 912 |
| cat aat gcc aag aca aag ccg cgg gag gag cag tac aac agc acg tac<br>His Asn Ala Lys Thr Lys Pro Arg Glu Glu Gln Tyr Asn Ser Thr Tyr<br>305                        310                      315                      320 | | 960 |
| cgt gtg gtc agc gtc ctc acc gtc ctg cac cag gac tgg ctg aat ggc<br>Arg Val Val Ser Val Leu Thr Val Leu His Gln Asp Trp Leu Asn Gly<br>                 325                      330                      335 | | 1008 |
| aag gag tac aag tgc aag gtc tcc aac aaa gcc ctc cca gcc ccc atc<br>Lys Glu Tyr Lys Cys Lys Val Ser Asn Lys Ala Leu Pro Ala Pro Ile<br>             340                      345                      350 | | 1056 |
| gag aaa acc atc tcc aaa gcc aaa ggg cag ccc cga gaa cca cag gtg<br>Glu Lys Thr Ile Ser Lys Ala Lys Gly Gln Pro Arg Glu Pro Gln Val<br>                 355                      360                      365 | | 1104 |
| tac acc ctg ccc cca tcc cgg gat gag ctg acc aag aac cag gtc agc<br>Tyr Thr Leu Pro Pro Ser Arg Asp Glu Leu Thr Lys Asn Gln Val Ser<br>370                        375                      380 | | 1152 |
| ctg acc tgc ctg gtc aaa ggc ttc tat ccc agc gac atc gcc gtg gag<br>Leu Thr Cys Leu Val Lys Gly Phe Tyr Pro Ser Asp Ile Ala Val Glu<br>385                        390                      395                      400 | | 1200 |
| tgg gag agc aat ggg cag ccg gag aac aac tac aag acc acg cct ccc<br>Trp Glu Ser Asn Gly Gln Pro Glu Asn Asn Tyr Lys Thr Thr Pro Pro<br>                 405                      410                      415 | | 1248 |

-continued

```
gtg ctg gac tcc gac ggc tcc ttc ttc ctc tac agc aag ctc acc gtg      1296
Val Leu Asp Ser Asp Gly Ser Phe Phe Leu Tyr Ser Lys Leu Thr Val
        420                 425                 430 gac aag agc agg tgg cag cag ggg aac gtc ttc tca tgc tcc gtg atg      1344
Asp Lys Ser Arg Trp Gln Gln Gly Asn Val Phe Ser Cys Ser Val Met
    435                 440                 445 cat gag gct ctg cac aac cac tac acg cag aag agc ctc tcc ctg tct      1392
His Glu Ala Leu His Asn His Tyr Thr Gln Lys Ser Leu Ser Leu Ser
450                 455                 460 ccg ggt aaa tga                                                       1404
Pro Gly Lys
465

<210> SEQ ID NO 10
<211> LENGTH: 467
<212> TYPE: PRT
<213> ORGANISM: Artificial Sequence
<220> FEATURE:
<223> OTHER INFORMATION: Synthetic Construct

<400> SEQUENCE: 10

Met Asp Trp Thr Trp Ser Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Ile Ser Trp Val Arg Gln Ala Pro Gly Gln Gly Leu
    50                  55                  60

Glu Trp Met Gly Trp Ile Ser Ala Tyr Asn Gly Asn Thr Asn Tyr Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Ala Ala Ala Gly Gly Tyr Phe Gln His Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
```

```
                275                 280                 285
Glu Asp Pro Glu Val Lys Phe Asn Trp Tyr Val Asp Gly Val Glu Val
290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Asp Glu Leu Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Lys
465

<210> SEQ ID NO 11
<211> LENGTH: 708
<212> TYPE: DNA
<213> ORGANISM: Artificial Sequence
<220> FEATURE:
<223> OTHER INFORMATION: Synthetic M2Z3 Light chian
<220> FEATURE:
<221> NAME/KEY: CDS
<222> LOCATION: (1)..(708)

<400> SEQUENCE: 11 atg gcc agc ttc cct ctc ctc ctc acc ctc ctc act cac tgt gca ggg    48
Met Ala Ser Phe Pro Leu Leu Leu Thr Leu Leu Thr His Cys Ala Gly
1               5                   10                  15 tcc tgg gcc cag tct gtg ctg act cag cca ccc tca gcg tct ggg acc    96
Ser Trp Ala Gln Ser Val Leu Thr Gln Pro Pro Ser Ala Ser Gly Thr
            20                  25                  30 ccc ggg cag agg gtc acc atc tct tgt tct gga agc aac tcc aac atc    144
Pro Gly Gln Arg Val Thr Ile Ser Cys Ser Gly Ser Asn Ser Asn Ile
        35                  40                  45 gga agt aaa act gta aac tgg tac cag cag ctc cca gga acg gcc ccc    192
Gly Ser Lys Thr Val Asn Trp Tyr Gln Gln Leu Pro Gly Thr Ala Pro
    50                  55                  60 aaa ctc ctc atc tct agt aat aat cag cgg ccc tca ggg gtc cct gac    240
Lys Leu Leu Ile Ser Ser Asn Asn Gln Arg Pro Ser Gly Val Pro Asp
65                  70                  75                  80 cga ttc tct ggc tcc aag tct ggc acc tca gcc tcc ctg gcc atc agt    288
Arg Phe Ser Gly Ser Lys Ser Gly Thr Ser Ala Ser Leu Ala Ile Ser
                85                  90                  95 ggg ctc cag tct gag gat gag gct gat tat tac tgt gca gca tgg gat    336
Gly Leu Gln Ser Glu Asp Glu Ala Asp Tyr Tyr Cys Ala Ala Trp Asp
            100                 105                 110
```

| | | |
|---|---|---|
| gac agc ctg aat ggt gtg gta ttc ggc gga ggg acc aag ctg acc gtc<br>Asp Ser Leu Asn Gly Val Val Phe Gly Gly Gly Thr Lys Leu Thr Val<br>      115                                120                        125 | 384 |
| cta ggt cag ccc aag gct gcc ccc tcg gtc act ctg ttc cca ccc tcc<br>Leu Gly Gln Pro Lys Ala Ala Pro Ser Val Thr Leu Phe Pro Pro Ser<br>130                                135                                140 | 432 |
| tct gag gag ctt caa gcc aac aag gcc aca ctg gtg tgt ctc ata agt<br>Ser Glu Glu Leu Gln Ala Asn Lys Ala Thr Leu Val Cys Leu Ile Ser<br>145                                150                              155                        160 | 480 |
| gac ttc tac ccg gga gcc gtg aca gtg gcc tgg aag gca gat agc agc<br>Asp Phe Tyr Pro Gly Ala Val Thr Val Ala Trp Lys Ala Asp Ser Ser<br>                        165                              170                            175 | 528 |
| ccc gtc aag gcg gga gtg gag acc acc aca ccc tcc aaa caa agc aac<br>Pro Val Lys Ala Gly Val Glu Thr Thr Thr Pro Ser Lys Gln Ser Asn<br>                            180                              185                              190 | 576 |
| aac aag tac gcg gcc agc agc tac ctg agc ctg acg cct gag cag tgg<br>Asn Lys Tyr Ala Ala Ser Ser Tyr Leu Ser Leu Thr Pro Glu Gln Trp<br>                    195                              200                              205 | 624 |
| aag tcc cac aaa agc tac agc tgc cag gtc acg cat gaa ggg agc acc<br>Lys Ser His Lys Ser Tyr Ser Cys Gln Val Thr His Glu Gly Ser Thr<br>210                              215                              220 | 672 |
| gtg gag aag aca gtg gcc cct aca gaa tgt tca tag<br>Val Glu Lys Thr Val Ala Pro Thr Glu Cys Ser<br>225                              230                              235 | 708 |

<210> SEQ ID NO 12
<211> LENGTH: 235
<212> TYPE: PRT
<213> ORGANISM: Artificial Sequence
<220> FEATURE:
<223> OTHER INFORMATION: Synthetic Construct

<400> SEQUENCE: 12

Met Ala Ser Phe Pro Leu Leu Leu Thr Leu Leu Thr His Cys Ala Gly
1               5                   10                  15

Ser Trp Ala Gln Ser Val Leu Thr Gln Pro Pro Ser Ala Ser Gly Thr
            20                  25                  30

Pro Gly Gln Arg Val Thr Ile Ser Cys Ser Gly Ser Asn Ser Asn Ile
        35                  40                  45

Gly Ser Lys Thr Val Asn Trp Tyr Gln Gln Leu Pro Gly Thr Ala Pro
    50                  55                  60

Lys Leu Leu Ile Ser Ser Asn Asn Gln Arg Pro Ser Gly Val Pro Asp
65                  70                  75                  80

Arg Phe Ser Gly Ser Lys Ser Gly Thr Ser Ala Ser Leu Ala Ile Ser
                85                  90                  95

Gly Leu Gln Ser Glu Asp Glu Ala Asp Tyr Tyr Cys Ala Ala Trp Asp
            100                 105                 110

Asp Ser Leu Asn Gly Val Val Phe Gly Gly Gly Thr Lys Leu Thr Val
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp

```
              195                 200                 205
Lys Ser His Lys Ser Tyr Ser Cys Gln Val Thr His Glu Gly Ser Thr
        210                 215                 220

Val Glu Lys Thr Val Ala Pro Thr Glu Cys Ser
225                 230                 235

<210> SEQ ID NO 13
<211> LENGTH: 1855
<212> TYPE: DNA
<213> ORGANISM: Artificial Sequence
<220> FEATURE:
<223> OTHER INFORMATION: Synthetic nonautologus Tol1 transposon

<400> SEQUENCE: 13
cagtagcggt tctaggcacg ggccgtccgg gcggtggcct ggggcggaaa actgaagggg      60
ggcggcaccg gcggctcagc cctttgtaat atattaatat gcaccactat tggtttactt     120
atgtcacagt ttgtaagttt gtaacagcct gaacctggcc gcgccgccgc cctcgccccg     180
cagctgcgct ctcctgtctt tgagaagtag acacaaatgt gtgtgaagaa ggagaaggga     240
gggggcgcgg ggtgagcacg gagcgtcgcc gcgtttgcgc atgcgcaaaa cctggctggc     300
tcatctttca ggggaggcga cggtcgcggg cttgatgaaa aaataaaaag taaaaactgc     360
gactgcgccg tcatgtagcg aatcagcgcc cctggctgta gctgcacgcg ctcctgctgg     420
aaatgtgtga agaggggggg ggggggggg gctgcgggga atcagttcaa ttgtgggacg     480
cttccaaatt aagtggctag gtggggacaa gggcgggggt ttgaatctac ttcataaaac     540 cttttttatat tataagtcag tcataaggtg acattctata acctacattt taataaaggt     600
ataaaaaata tattctgctt tttttgggtt aattttgtgt gaaatgtcca aataaaaaaa     660
atggcaacac aaaacaatgc tgtcactaag gtgacagttg gttcagtcga cggacttgat     720
gccttcttcg tgacgtgagg acatttatgc caaacaaacg ccaataaaca tctaaaatat     780
ggaaaagaaa aggtcaaagc catctggtgc ccaatttaga aagaaaagaa aagaagaaga     840
ggagaaaaga gataagaaa agggtaagtc ctcacagctt gatgcatgtt ttttctaaat     900
tctaatgcta cctgccctac aacaacgttg ccgatgaaaa ctttattttg gtcgatgacc     960
aacactgaat taggcccaaa tgttgcaaat agcgtcattt ttttttttt ttttagattt    1020 tattcttaaa aatttgctct gccttaactt gtaacattag ttatgattca tgtgtctgtc    1080
tgctctgctg taacacaaag gttttgttgg gttttgctgt tgtatactag ctcataatgt    1140
taaaaaagct gtgatggtta cacagcatgc tggtgctgcc ataagatgct aatggggcaa    1200
ataatttgag attggtcatt aatttaataa tcatttgtgg cagcctaaac gttttcacaa    1260 tgttttttttg acatttaact ggggatttag gggttaattt tgagcctgca tatgaagttt    1320 atttttatt tgttttacaa atgtgggatt atatttttag ccaatagaat ttccataaat    1380
ctgtaggtag tttaaaaaat gaatatttac catttactgc aactctatgg ggacaaaaca    1440
taatgtaaca ggtcataact aaaaatgtgc caatcaaagg attgaagacg gaaaacatga    1500
gttaattttt cttctctgaa gtagagatcg atatagaaca tgacaattta aatttccaat    1560
tcataaatgt ttttaaaata tttattttat attatttatt taacattgag tttgattcaa    1620
tattttctta gctaactgta tttttgccat gcttatggtc ttttattttt tgtgttctga    1680 taactttttat aatgcttttc agaatttga catcttttgt atccacttct taatttcaat    1740
gacaataaaa catttcagtt gacgaagaca aacaaagttc tgttgtgact atgggggggg    1800
ggggcgcctg gggatggtct cgcccgggga gtaattcagg gtagaaccgc cactg         1855
```

<210> SEQ ID NO 14
<211> LENGTH: 200
<212> TYPE: DNA
<213> ORGANISM: Artificial Sequence
<220> FEATURE:
<223> OTHER INFORMATION: Synthetic Tol1-L transposon sequence

<400> SEQUENCE: 14

```
cagtagcggt tctaggcacg ggccgtccgg gcggtggcct ggggcggaaa actgaagggg      60
ggcggcaccg gcggctcagc cctttgtaat atattaatat gcaccactat tggtttactt     120
atgtcacagt ttgtaagttt gtaacagcct gaacctggcc gcgccgccgc cctcgccccg     180
cagctgcgct ctcctgtctt                                                 200
```

<210> SEQ ID NO 15
<211> LENGTH: 505
<212> TYPE: DNA
<213> ORGANISM: Artificial Sequence
<220> FEATURE:
<223> OTHER INFORMATION: Synthetic Tol1-R transoposon sequence

<400> SEQUENCE: 15

```
atatttttag ccaatagaat ttccataaat ctgtaggtag ttttaaaaat gaatatttac      60
catttactgc aactctatgg ggacaaaaca taatgtaaca ggtcataact aaaaatgtgc     120
caatcaaagg attgaagacg gaaaacatga gttaattttt cttctctgaa gtagagatcg     180
atatagaaca tgacaattta aatttccaat tcataaatgt ttttaaaata tttatttat    240 attatttatt taacattgag tttgattcaa tattttctta gctaactgta tttttgccat     300
gcttatggtc ttttattttt tgtgttctga taacttttat aatgcttttc agaattttga     360
catcttttgt atccacttct taatttcaat gacaataaaa catttcagtt gacgaagaca     420
aacaaagttc tgttgtgact atggggggg ggggcgcctg gggatggtct cgcccgggga     480
gtaattcagg gtagaaccgc cactg                                           505
```

<210> SEQ ID NO 16
<211> LENGTH: 2745
<212> TYPE: DNA
<213> ORGANISM: Oryzias latipes
<220> FEATURE:
<221> NAME/KEY: CDS
<222> LOCATION: (30)..(2585)

<400> SEQUENCE: 16

```
gccaaacaaa cgccaaaaac atctaaaat atg gag aaa aaa agg tca aag cca       53
                              Met Glu Lys Lys Arg Ser Lys Pro
                                1               5 tct ggt gcc caa ttt aga aag aaa aga aaa gaa gaa gag gag aaa aga      101
Ser Gly Ala Gln Phe Arg Lys Lys Arg Lys Glu Glu Glu Glu Lys Arg
     10                  15                  20 gat aaa gaa aag ggg gca ctt cta aga tat ttt gga tcg tct acc act      149
Asp Lys Glu Lys Gly Ala Leu Leu Arg Tyr Phe Gly Ser Ser Thr Thr
 25                  30                  35                  40 gct caa gat gag aca tct acc tcc ctg cca gct atc tca tca gcc aca      197
Ala Gln Asp Glu Thr Ser Thr Ser Leu Pro Ala Ile Ser Ser Ala Thr
                 45                  50                  55 gtc aca gtc tca ccc cct cag gat gag cta cca tct aca tcc tct gct      245
Val Thr Val Ser Pro Pro Gln Asp Glu Leu Pro Ser Thr Ser Ser Ala
             60                  65                  70 act cat gta gtt cca cag ttg tta cct gag caa agt ttt gat agt gag      293
```

```
                Thr His Val Val Pro Gln Leu Leu Pro Glu Gln Ser Phe Asp Ser Glu
                        75                  80                  85 gct gaa gac gtt gtt cca tct acg tct acc cag ctt gag act tca gaa       341
Ala Glu Asp Val Val Pro Ser Thr Ser Thr Gln Leu Glu Thr Ser Glu
        90                  95                  100 atg cct ggt gat gaa acc cca ctg acc ccg act gct gag gac cag cct       389
Met Pro Gly Asp Glu Thr Pro Leu Thr Pro Thr Ala Glu Asp Gln Pro
105                 110                 115                 120 cta cca act gac cct gca aag tgg ccc tca cct ctg act gac agg ata       437
Leu Pro Thr Asp Pro Ala Lys Trp Pro Ser Pro Leu Thr Asp Arg Ile
                125                 130                 135 cgg atg gag ctg gtt cga aga gga cca agt agc ata cca cct gac ttt       485
Arg Met Glu Leu Val Arg Arg Gly Pro Ser Ser Ile Pro Pro Asp Phe
            140                 145                 150 gtt ttc cca aga aat gac agt gat ggg aga agt tgt cat cac cac tat       533
Val Phe Pro Arg Asn Asp Ser Asp Gly Arg Ser Cys His His His Tyr
        155                 160                 165 ttc agg aag aca cta gta agt ggt gaa aaa ata gca aga act tgg ttg       581
Phe Arg Lys Thr Leu Val Ser Gly Glu Lys Ile Ala Arg Thr Trp Leu
    170                 175                 180 atg tat tca aaa gtg aag aac agc ctc ttt tgc ttt tgt tgc aaa ttg       629
Met Tyr Ser Lys Val Lys Asn Ser Leu Phe Cys Phe Cys Cys Lys Leu
185                 190                 195                 200 ttt tcc aac aaa aac att aat tta aca act tct ggt aca gca aac tgg       677
Phe Ser Asn Lys Asn Ile Asn Leu Thr Thr Ser Gly Thr Ala Asn Trp
                205                 210                 215 aaa cat gca agc aca tac ctc aca gca cac gaa aaa agc cca gaa cac       725
Lys His Ala Ser Thr Tyr Leu Thr Ala His Glu Lys Ser Pro Glu His
            220                 225                 230 ctc aat tgt atg aaa gca tgg aag gaa ctg tca ggg agg atc aga agt       773
Leu Asn Cys Met Lys Ala Trp Lys Glu Leu Ser Gly Arg Ile Arg Ser
        235                 240                 245 ggg aaa aca att gat aag cag gag atg gca ctt ctg gaa gag gag cgg       821
Gly Lys Thr Ile Asp Lys Gln Glu Met Ala Leu Leu Glu Glu Glu Arg
    250                 255                 260 gtg aga tgg aga gca gtg cta acc cgt ctc att gct att gtg cag tca       869
Val Arg Trp Arg Ala Val Leu Thr Arg Leu Ile Ala Ile Val Gln Ser
265                 270                 275                 280 ctg gca gtt cgg aat ttg gct cta agg gga cac aca gaa aca ctg ttc       917
Leu Ala Val Arg Asn Leu Ala Leu Arg Gly His Thr Glu Thr Leu Phe
                285                 290                 295 aca tca tca aat ggg aat ttt ttg aaa gag gtt gaa ctg atg gcc agg       965
Thr Ser Ser Asn Gly Asn Phe Leu Lys Glu Val Glu Leu Met Ala Arg
            300                 305                 310 ttt gat ccc ata atg aaa gat cat ctt aac cgt gta tta aga gga aca      1013
Phe Asp Pro Ile Met Lys Asp His Leu Asn Arg Val Leu Arg Gly Thr
        315                 320                 325 gca agt cac aac agc tac ata ggc cat cat gtg cag aat gaa ctt att      1061
Ala Ser His Asn Ser Tyr Ile Gly His His Val Gln Asn Glu Leu Ile
    330                 335                 340 gat ttg ttg agc agc aaa atc cta tcc gct ata gtg gat gac atc aaa      1109
Asp Leu Leu Ser Ser Lys Ile Leu Ser Ala Ile Val Asp Asp Ile Lys
345                 350                 355                 360 aag gca aaa tat ttt tca ata att ctg gac tgc act ctg gat ata agc      1157
Lys Ala Lys Tyr Phe Ser Ile Ile Leu Asp Cys Thr Leu Asp Ile Ser
                365                 370                 375 cac aca gaa cag ttg tca gtt ata att aga gtg gtg tca ctg atg gag      1205
His Thr Glu Gln Leu Ser Val Ile Ile Arg Val Val Ser Leu Met Glu
            380                 385                 390
```

```
aag cct cag atc agg gaa cat ttt atg ggg ttt ttg gag gca gag gag    1253
Lys Pro Gln Ile Arg Glu His Phe Met Gly Phe Leu Glu Ala Glu Glu
        395                 400                 405 tcc aca ggc cag cac ttg gca tcc atg atc tta aac aga ctt gag gag    1301
Ser Thr Gly Gln His Leu Ala Ser Met Ile Leu Asn Arg Leu Glu Glu
    410                 415                 420 tta gga att tct ttt gaa gac tgc aga gga caa tca tat gat aat ggg    1349
Leu Gly Ile Ser Phe Glu Asp Cys Arg Gly Gln Ser Tyr Asp Asn Gly
425                 430                 435                 440 gca aat atg aaa ggc aaa aat aag gga gta caa gcc agg ctc tta gaa    1397
Ala Asn Met Lys Gly Lys Asn Lys Gly Val Gln Ala Arg Leu Leu Glu
            445                 450                 455 aag aat ccc cgt gct ctg ttt ttg cca tgc ggt gca cac aca ttg aat    1445
Lys Asn Pro Arg Ala Leu Phe Leu Pro Cys Gly Ala His Thr Leu Asn
        460                 465                 470 tta gtt gtg tgt gat gct gct aag aga tct gtt gat gct atg agc tac    1493
Leu Val Val Cys Asp Ala Ala Lys Arg Ser Val Asp Ala Met Ser Tyr
    475                 480                 485 ttt ggt gtc ctg caa aag ctt tac act tta ttt tca gcc tct gcc caa    1541
Phe Gly Val Leu Gln Lys Leu Tyr Thr Leu Phe Ser Ala Ser Ala Gln
490                 495                 500 cga tgg gcc ata ctg aag agt cag gtg agc atc act cta aag tcg tgg    1589
Arg Trp Ala Ile Leu Lys Ser Gln Val Ser Ile Thr Leu Lys Ser Trp
505                 510                 515                 520 aca gaa aca agg tgg gag agc aaa atc aaa agc atc gag ccc atg agg    1637
Thr Glu Thr Arg Trp Glu Ser Lys Ile Lys Ser Ile Glu Pro Met Arg
                525                 530                 535 tac cag gga gct gca gtg aga gag gct tta ata gaa gtg aga gac aag    1685
Tyr Gln Gly Ala Ala Val Arg Glu Ala Leu Ile Glu Val Arg Asp Lys
            540                 545                 550 acc aaa gac cca gtt ata aag gct gag gcc cag tct ttg tct gaa gag    1733
Thr Lys Asp Pro Val Ile Lys Ala Glu Ala Gln Ser Leu Ser Glu Glu
        555                 560                 565 gta ggg tcg tac cgc ttc aac atc tgc aca gtc gta tgg cat gac att    1781
Val Gly Ser Tyr Arg Phe Asn Ile Cys Thr Val Val Trp His Asp Ile
    570                 575                 580 cta tct aca ata aag cat gtc agc aaa ctc atg cag tct cca aat atg    1829
Leu Ser Thr Ile Lys His Val Ser Lys Leu Met Gln Ser Pro Asn Met
585                 590                 595                 600 cat gtg gac cta gct gtg agt ctt ttg aag aag act gaa caa agt ctc    1877
His Val Asp Leu Ala Val Ser Leu Leu Lys Lys Thr Glu Gln Ser Leu
                605                 610                 615 cag agc tac agg gca aat ggc ttt gtg aat gca cag atg gca gcc aaa    1925
Gln Ser Tyr Arg Ala Asn Gly Phe Val Asn Ala Gln Met Ala Ala Lys
            620                 625                 630 gaa atg tgc aag gaa atg aat gtc gag gct att ttg aaa caa aaa aga    1973
Glu Met Cys Lys Glu Met Asn Val Glu Ala Ile Leu Lys Gln Lys Arg
        635                 640                 645 ata aga tcc aca aag tgc caa ttc tcg tat gaa tca cac gat gag cct    2021
Ile Arg Ser Thr Lys Cys Gln Phe Ser Tyr Glu Ser His Asp Glu Pro
    650                 655                 660 ttc agt gac gca ctt aaa aag ttg gag gtt gaa ttt ttc aat gtt gtt    2069
Phe Ser Asp Ala Leu Lys Lys Leu Glu Val Glu Phe Phe Asn Val Val
665                 670                 675                 680 gtt gat gaa gcc ttg tca gcc atc gcg gag agg ttt tcc aca ttg gaa    2117
Val Asp Glu Ala Leu Ser Ala Ile Ala Glu Arg Phe Ser Thr Leu Glu
                685                 690                 695 gtt gta caa aac aga ttt ggg gtt ttg acc aat ttc cca agc ctt gga    2165
Val Val Gln Asn Arg Phe Gly Val Leu Thr Asn Phe Pro Ser Leu Gly
            700                 705                 710
```

```
gac gag gag ctg acg gag caa tgc gag gca cta ggc aac ata ctc cat    2213
Asp Glu Glu Leu Thr Glu Gln Cys Glu Ala Leu Gly Asn Ile Leu His
            715                 720                 725 ttt gag aag aac tgg gat ttg gac agt aga gag ctt gtt cag gaa atc    2261
Phe Glu Lys Asn Trp Asp Leu Asp Ser Arg Glu Leu Val Gln Glu Ile
730                 735                 740 aag aac ttg cct aac tta cca tca acg act cca agt ctc ctt gag ctc    2309
Lys Asn Leu Pro Asn Leu Pro Ser Thr Thr Pro Ser Leu Leu Glu Leu
745                 750                 755                 760 atc tct ttc atg tct gat aag gat cta tca gaa atc tat ccg aac ttt    2357
Ile Ser Phe Met Ser Asp Lys Asp Leu Ser Glu Ile Tyr Pro Asn Phe
                765                 770                 775 tgg act gct ctc agg att gca ctc acc ttg cca gtc act gtg gct caa    2405
Trp Thr Ala Leu Arg Ile Ala Leu Thr Leu Pro Val Thr Val Ala Gln
            780                 785                 790 gca gag agg agc ttt tca aaa cta aaa ttg atc aag tcg tac ctg agg    2453
Ala Glu Arg Ser Phe Ser Lys Leu Lys Leu Ile Lys Ser Tyr Leu Arg
        795                 800                 805 tca aca atg tca cag gag cga ctc act aac ctt gcc gtt gtt agc atc    2501
Ser Thr Met Ser Gln Glu Arg Leu Thr Asn Leu Ala Val Val Ser Ile
    810                 815                 820 aat cac tca gta ggg gag cag ata tca tat gat gat gtt att gac gag    2549
Asn His Ser Val Gly Glu Gln Ile Ser Tyr Asp Asp Val Ile Asp Glu
825                 830                 835                 840 ttt gca tca aga aag gct agg aag gtt agg ttt tag ttggtgtttt         2595
Phe Ala Ser Arg Lys Ala Arg Lys Val Arg Phe
                845                 850 ctgttattgt attggtgctg cagttatatt tattttagcg tgtcatttgt gtgataaaag  2655
gtttgtgctt tataatattt atttttatatt atttattcaa tattgagttt gattcaatat 2715 tttcttagct aactgtattt ttgccatgct                                   2745

<210> SEQ ID NO 17
<211> LENGTH: 851
<212> TYPE: PRT
<213> ORGANISM: Oryzias latipes

<400> SEQUENCE: 17

Met Glu Lys Lys Arg Ser Lys Pro Ser Gly Ala Gln Phe Arg Lys Lys
1               5                   10                  15

Arg Lys Glu Glu Glu Lys Arg Asp Lys Glu Lys Gly Ala Leu Leu
            20                  25                  30

Arg Tyr Phe Gly Ser Ser Thr Thr Ala Gln Asp Glu Thr Ser Thr Ser
        35                  40                  45

Leu Pro Ala Ile Ser Ser Ala Thr Val Thr Val Ser Pro Pro Gln Asp
    50                  55                  60

Glu Leu Pro Ser Thr Ser Ser Ala Thr His Val Val Pro Gln Leu Leu
65                  70                  75                  80

Pro Glu Gln Ser Phe Asp Ser Glu Ala Glu Asp Val Val Pro Ser Thr
                85                  90                  95

Ser Thr Gln Leu Glu Thr Ser Glu Met Pro Gly Asp Glu Thr Pro Leu
            100                 105                 110

Thr Pro Thr Ala Glu Asp Gln Pro Leu Pro Thr Asp Pro Ala Lys Trp
        115                 120                 125

Pro Ser Pro Leu Thr Asp Arg Ile Arg Met Glu Leu Val Arg Arg Gly
    130                 135                 140

Pro Ser Ser Ile Pro Pro Asp Phe Val Phe Pro Arg Asn Asp Ser Asp
```

-continued

```
            145                 150                 155                 160
        Gly Arg Ser Cys His His His Tyr Phe Arg Lys Thr Leu Val Ser Gly
                        165                 170                 175
        Glu Lys Ile Ala Arg Thr Trp Leu Met Tyr Ser Lys Val Lys Asn Ser
                        180                 185                 190
        Leu Phe Cys Phe Cys Cys Lys Leu Phe Ser Asn Lys Asn Ile Asn Leu
                        195                 200                 205
        Thr Thr Ser Gly Thr Ala Asn Trp Lys His Ala Ser Thr Tyr Leu Thr
                    210                 215                 220
        Ala His Glu Lys Ser Pro Glu His Leu Asn Cys Met Lys Ala Trp Lys
        225                 230                 235                 240
        Glu Leu Ser Gly Arg Ile Arg Ser Gly Lys Thr Ile Asp Lys Gln Glu
                            245                 250                 255
        Met Ala Leu Leu Glu Glu Arg Val Arg Trp Arg Ala Val Leu Thr
                        260                 265                 270
        Arg Leu Ile Ala Ile Val Gln Ser Leu Ala Val Arg Asn Leu Ala Leu
                        275                 280                 285
        Arg Gly His Thr Glu Thr Leu Phe Thr Ser Ser Asn Gly Asn Phe Leu
                    290                 295                 300
        Lys Glu Val Glu Leu Met Ala Arg Phe Asp Pro Ile Met Lys Asp His
        305                 310                 315                 320
        Leu Asn Arg Val Leu Arg Gly Thr Ala Ser His Asn Ser Tyr Ile Gly
                        325                 330                 335
        His His Val Gln Asn Glu Leu Ile Asp Leu Leu Ser Ser Lys Ile Leu
                        340                 345                 350
        Ser Ala Ile Val Asp Asp Ile Lys Lys Ala Lys Tyr Phe Ser Ile Ile
                    355                 360                 365
        Leu Asp Cys Thr Leu Asp Ile Ser His Thr Glu Gln Leu Ser Val Ile
                    370                 375                 380
        Ile Arg Val Val Ser Leu Met Glu Lys Pro Gln Ile Arg Glu His Phe
        385                 390                 395                 400
        Met Gly Phe Leu Glu Ala Glu Ser Thr Gly Gln His Leu Ala Ser
                        405                 410                 415
        Met Ile Leu Asn Arg Leu Glu Glu Leu Gly Ile Ser Phe Glu Asp Cys
                        420                 425                 430
        Arg Gly Gln Ser Tyr Asp Asn Gly Ala Asn Met Lys Gly Lys Asn Lys
                    435                 440                 445
        Gly Val Gln Ala Arg Leu Leu Glu Lys Asn Pro Arg Ala Leu Phe Leu
                    450                 455                 460
        Pro Cys Gly Ala His Thr Leu Asn Leu Val Val Cys Asp Ala Ala Lys
        465                 470                 475                 480
        Arg Ser Val Asp Ala Met Ser Tyr Phe Gly Val Leu Gln Lys Leu Tyr
                        485                 490                 495
        Thr Leu Phe Ser Ala Ser Ala Gln Arg Trp Ala Ile Leu Lys Ser Gln
                        500                 505                 510
        Val Ser Ile Thr Leu Lys Ser Trp Thr Glu Thr Arg Trp Glu Ser Lys
                    515                 520                 525
        Ile Lys Ser Ile Glu Pro Met Arg Tyr Gln Gly Ala Ala Val Arg Glu
                    530                 535                 540
        Ala Leu Ile Glu Val Arg Asp Lys Thr Lys Asp Pro Val Ile Lys Ala
        545                 550                 555                 560
        Glu Ala Gln Ser Leu Ser Glu Glu Val Gly Ser Tyr Arg Phe Asn Ile
                        565                 570                 575
```

```
Cys Thr Val Val Trp His Asp Ile Leu Ser Thr Ile Lys His Val Ser
            580                 585                 590

Lys Leu Met Gln Ser Pro Asn Met His Val Asp Leu Ala Val Ser Leu
            595                 600                 605

Leu Lys Lys Thr Glu Gln Ser Leu Gln Ser Tyr Arg Ala Asn Gly Phe
610                 615                 620

Val Asn Ala Gln Met Ala Ala Lys Glu Met Cys Lys Glu Met Asn Val
625                 630                 635                 640

Glu Ala Ile Leu Lys Gln Lys Arg Ile Arg Ser Thr Lys Cys Gln Phe
            645                 650                 655

Ser Tyr Glu Ser His Asp Glu Pro Phe Ser Asp Ala Leu Lys Lys Leu
            660                 665                 670

Glu Val Glu Phe Phe Asn Val Val Asp Glu Ala Leu Ser Ala Ile
            675                 680                 685

Ala Glu Arg Phe Ser Thr Leu Glu Val Val Gln Asn Arg Phe Gly Val
            690                 695                 700

Leu Thr Asn Phe Pro Ser Leu Gly Asp Glu Glu Leu Thr Glu Gln Cys
705                 710                 715                 720

Glu Ala Leu Gly Asn Ile Leu His Phe Glu Lys Asn Trp Asp Leu Asp
            725                 730                 735

Ser Arg Glu Leu Val Gln Glu Ile Lys Asn Leu Pro Asn Leu Pro Ser
            740                 745                 750

Thr Thr Pro Ser Leu Leu Glu Leu Ile Ser Phe Met Ser Asp Lys Asp
            755                 760                 765

Leu Ser Glu Ile Tyr Pro Asn Phe Trp Thr Ala Leu Arg Ile Ala Leu
            770                 775                 780

Thr Leu Pro Val Thr Val Ala Gln Ala Glu Arg Ser Phe Ser Lys Leu
785                 790                 795                 800

Lys Leu Ile Lys Ser Tyr Leu Arg Ser Thr Met Ser Gln Glu Arg Leu
            805                 810                 815

Thr Asn Leu Ala Val Val Ser Ile Asn His Ser Val Gly Glu Gln Ile
            820                 825                 830

Ser Tyr Asp Asp Val Ile Asp Glu Phe Ala Ser Arg Lys Ala Arg Lys
            835                 840                 845

Val Arg Phe
    850

<210> SEQ ID NO 18
<211> LENGTH: 417
<212> TYPE: DNA
<213> ORGANISM: Artificial Sequence
<220> FEATURE:
<223> OTHER INFORMATION: Synthetic VH region of anti-CD98 antibody
<220> FEATURE:
<221> NAME/KEY: CDS
<222> LOCATION: (1)..(417)

<400> SEQUENCE: 18 atg aag cac ctg tgg ttc ttc ctc ctg ctg gtg gcg gct ccc aga tgg     48
Met Lys His Leu Trp Phe Phe Leu Leu Leu Val Ala Ala Pro Arg Trp
1               5                   10                  15 gtc ctg tcc cag ctg cag ctg cag gag tcg ggc cca gga ctg gtg aag     96
Val Leu Ser Gln Leu Gln Leu Gln Glu Ser Gly Pro Gly Leu Val Lys
            20                  25                  30 cct tcg gag acc ctg tcc ctc acc tgc act gtc tct ggt ggc tcc atc    144
Pro Ser Glu Thr Leu Ser Leu Thr Cys Thr Val Ser Gly Gly Ser Ile
        35                  40                  45
```

```
agc agt agt agt tac tac tgg ggc tgg atc cgc cag ccc cca ggg aag      192
Ser Ser Ser Ser Tyr Tyr Trp Gly Trp Ile Arg Gln Pro Pro Gly Lys
        50                  55                  60 ggg ctg gag tgg att ggg agt atc tat tat agt ggg agt acc tac tac      240
Gly Leu Glu Trp Ile Gly Ser Ile Tyr Tyr Ser Gly Ser Thr Tyr Tyr
 65              70                  75                  80 aac ccg tcc ctc aag agt cga gtc acc ata tcc gta gac acg tcc aag      288
Asn Pro Ser Leu Lys Ser Arg Val Thr Ile Ser Val Asp Thr Ser Lys
                 85                  90                  95 aac cag ttc tcc ctg aag ctg agc tct gtg acc gcc gca gac acg gct      336
Asn Gln Phe Ser Leu Lys Leu Ser Ser Val Thr Ala Ala Asp Thr Ala
                100                 105                 110 gtg tat tac tgt gcg aga caa ggg acg ggg ctc gcc cta ttt gac tac      384
Val Tyr Tyr Cys Ala Arg Gln Gly Thr Gly Leu Ala Leu Phe Asp Tyr
            115                 120                 125 tgg ggc cag gga acc ctg gtc acc gtc tcc tca                          417
Trp Gly Gln Gly Thr Leu Val Thr Val Ser Ser
        130                 135

<210> SEQ ID NO 19
<211> LENGTH: 139
<212> TYPE: PRT
<213> ORGANISM: Artificial Sequence
<220> FEATURE:
<223> OTHER INFORMATION: Synthetic Construct

<400> SEQUENCE: 19

Met Lys His Leu Trp Phe Phe Leu Leu Leu Val Ala Ala Pro Arg Trp
 1               5                  10                  15

Val Leu Ser Gln Leu Gln Leu Gln Glu Ser Gly Pro Gly Leu Val Lys
                20                  25                  30

Pro Ser Glu Thr Leu Ser Leu Thr Cys Thr Val Ser Gly Gly Ser Ile
             35                  40                  45

Ser Ser Ser Ser Tyr Tyr Trp Gly Trp Ile Arg Gln Pro Pro Gly Lys
        50                  55                  60

Gly Leu Glu Trp Ile Gly Ser Ile Tyr Tyr Ser Gly Ser Thr Tyr Tyr
 65              70                  75                  80

Asn Pro Ser Leu Lys Ser Arg Val Thr Ile Ser Val Asp Thr Ser Lys
                 85                  90                  95

Asn Gln Phe Ser Leu Lys Leu Ser Ser Val Thr Ala Ala Asp Thr Ala
                100                 105                 110

Val Tyr Tyr Cys Ala Arg Gln Gly Thr Gly Leu Ala Leu Phe Asp Tyr
            115                 120                 125

Trp Gly Gln Gly Thr Leu Val Thr Val Ser Ser
        130                 135

<210> SEQ ID NO 20
<211> LENGTH: 120
<212> TYPE: PRT
<213> ORGANISM: Artificial Sequence
<220> FEATURE:
<223> OTHER INFORMATION: Synthetic VH region of anti-CD98 antibody

<400> SEQUENCE: 20

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
```

```
                35                  40                  45
Trp Ile Gly Ser Ile Tyr Tyr Ser Gly Ser Thr Tyr Tyr Asn Pro Ser
         50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Gln Gly Thr Gly Leu Ala Leu Phe Asp Tyr Trp Gly Gln
            100                 105                 110

Gly Thr Leu Val Thr Val Ser Ser
        115                 120

<210> SEQ ID NO 21
<211> LENGTH: 387
<212> TYPE: DNA
<213> ORGANISM: Artificial Sequence
<220> FEATURE:
<223> OTHER INFORMATION: Synthetic VL region of anti-CD98 antibody
<220> FEATURE:
<221> NAME/KEY: CDS
<222> LOCATION: (1)..(387)

<400> SEQUENCE: 21 atg gaa acc cca gcg cag ctt ctc ttc ctc ctg cta ctc tgg ctc cca      48
Met Glu Thr Pro Ala Gln Leu Leu Phe Leu Leu Leu Leu Trp Leu Pro
 1               5                  10                  15 gat acc acc gga gaa att gtg ttg acg cag tct cca ggc acc ctg tct      96
Asp Thr Thr Gly Glu Ile Val Leu Thr Gln Ser Pro Gly Thr Leu Ser
             20                  25                  30 ttg tct cca ggg gaa aga gcc acc ctc tcc tgc agg gcc agt cag agt     144
Leu Ser Pro Gly Glu Arg Ala Thr Leu Ser Cys Arg Ala Ser Gln Ser
         35                  40                  45 gtt agc agc agc ttc tta gcc tgg tac cag cag aaa cct ggc cag gct     192
Val Ser Ser Ser Phe Leu Ala Trp Tyr Gln Gln Lys Pro Gly Gln Ala
     50                  55                  60 ccc agg ctc ctc atc tat ggt gca tcc agc agg gcc act ggc atc cca     240
Pro Arg Leu Leu Ile Tyr Gly Ala Ser Ser Arg Ala Thr Gly Ile Pro
 65                  70                  75                  80 gac agg ttc agt ggc agt ggg tct ggg aca gac ttc act ctc acc atc     288
Asp Arg Phe Ser Gly Ser Gly Ser Gly Thr Asp Phe Thr Leu Thr Ile
                 85                  90                  95 agc aga ctg gag cct gaa gat ttc gca gtg tat tac tgt cag cag tat     336
Ser Arg Leu Glu Pro Glu Asp Phe Ala Val Tyr Tyr Cys Gln Gln Tyr
            100                 105                 110 ggt agc tca cct cta ttc act ttc ggc cct ggg acc aaa gtg gat atc     384
Gly Ser Ser Pro Leu Phe Thr Phe Gly Pro Gly Thr Lys Val Asp Ile
        115                 120                 125 aaa                                                                  387
Lys

<210> SEQ ID NO 22
<211> LENGTH: 129
<212> TYPE: PRT
<213> ORGANISM: Artificial Sequence
<220> FEATURE:
<223> OTHER INFORMATION: Synthetic Construct

<400> SEQUENCE: 22

Met Glu Thr Pro Ala Gln Leu Leu Phe Leu Leu Leu Leu Trp Leu Pro
 1               5                  10                  15

Asp Thr Thr Gly Glu Ile Val Leu Thr Gln Ser Pro Gly Thr Leu Ser
```

```
            20                  25                  30
Leu Ser Pro Gly Glu Arg Ala Thr Leu Ser Cys Arg Ala Ser Gln Ser
        35                  40                  45

Val Ser Ser Ser Phe Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Pro Leu Phe Thr Phe Gly Pro Gly Thr Lys Val Asp Ile
        115                 120                 125

Lys

<210> SEQ ID NO 23
<211> LENGTH: 109
<212> TYPE: PRT
<213> ORGANISM: Artificial Sequence
<220> FEATURE:
<223> OTHER INFORMATION: Synthetic VL region of anti-CD98 antibody

<400> SEQUENCE: 23

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Phe Thr Phe Gly Pro Gly Thr Lys Val Asp Ile Lys
            100                 105

<210> SEQ ID NO 24
<211> LENGTH: 420
<212> TYPE: DNA
<213> ORGANISM: Artificial Sequence
<220> FEATURE:
<223> OTHER INFORMATION: Synthetic VH region of anti-TNF alpha antibody
<220> FEATURE:
<221> NAME/KEY: CDS
<222> LOCATION: (1)..(420)

<400> SEQUENCE: 24 atg gag ttg gga ctg agc tgg att ttc ctt ttg gct att tta aaa ggt      48
Met Glu Leu Gly Leu Ser Trp Ile Phe Leu Leu Ala Ile Leu Lys Gly
1               5                   10                  15 gtc cag tgt gag gtg cag ctg gtg gag tct ggg gga ggc ttg gta cag      96
Val Gln Cys Glu Val Gln Leu Val Glu Ser Gly Gly Gly Leu Val Gln
            20                  25                  30 ccc ggc agg tcc ctg aga ctc tcc tgt gcg gcc tct gga ttc acc ttt     144
Pro Gly Arg Ser Leu Arg Leu Ser Cys Ala Ala Ser Gly Phe Thr Phe
        35                  40                  45 gat gat tat gcc atg cac tgg gtc cgg caa gct cca ggg aag ggc ctg     192
Asp Asp Tyr Ala Met His Trp Val Arg Gln Ala Pro Gly Lys Gly Leu
```

```
                        Asp Asp Tyr Ala Met His Trp Val Arg Gln Ala Pro Gly Lys Gly Leu
                            50                  55                  60 gaa tgg gtc tca gct atc act tgg aat agt ggt cac ata gac tat gcg        240
Glu Trp Val Ser Ala Ile Thr Trp Asn Ser Gly His Ile Asp Tyr Ala
 65                  70                  75                  80 gac tct gtg gag ggc cga ttc acc atc tcc aga gac aac gcc aag aac        288
Asp Ser Val Glu Gly Arg Phe Thr Ile Ser Arg Asp Asn Ala Lys Asn
                 85                  90                  95 tcc ctg tat ctg caa atg aac agt ctg aga gct gag gat acg gcc gta        336
Ser Leu Tyr Leu Gln Met Asn Ser Leu Arg Ala Glu Asp Thr Ala Val
            100                 105                 110 tat tac tgt gcg aaa gtc tcg tac ctt agc acc gcg tcc tcc ctt gac        384
Tyr Tyr Cys Ala Lys Val Ser Tyr Leu Ser Thr Ala Ser Ser Leu Asp
        115                 120                 125 tat tgg ggc caa ggt acc ctg gtc acc gtc tcg tca                        420
Tyr Trp Gly Gln Gly Thr Leu Val Thr Val Ser Ser
130                 135                 140

<210> SEQ ID NO 25
<211> LENGTH: 140
<212> TYPE: PRT
<213> ORGANISM: Artificial Sequence
<220> FEATURE:
<223> OTHER INFORMATION: Synthetic Construct

<400> SEQUENCE: 25

Met Glu Leu Gly Leu Ser Trp Ile Phe Leu Leu Ala Ile Leu Lys Gly
 1               5                  10                  15

Val Gln Cys Glu Val Gln Leu Val Glu Ser Gly Gly Gly Leu Val Gln
                20                  25                  30

Pro Gly Arg Ser Leu Arg Leu Ser Cys Ala Ala Ser Gly Phe Thr Phe
            35                  40                  45

Asp Asp Tyr Ala Met His Trp Val Arg Gln Ala Pro Gly Lys Gly Leu
    50                  55                  60

Glu Trp Val Ser Ala Ile Thr Trp Asn Ser Gly His Ile Asp Tyr Ala
 65                  70                  75                  80

Asp Ser Val Glu Gly Arg Phe Thr Ile Ser Arg Asp Asn Ala Lys Asn
                 85                  90                  95

Ser Leu Tyr Leu Gln Met Asn Ser Leu Arg Ala Glu Asp Thr Ala Val
            100                 105                 110

Tyr Tyr Cys Ala Lys Val Ser Tyr Leu Ser Thr Ala Ser Ser Leu Asp
        115                 120                 125

Tyr Trp Gly Gln Gly Thr Leu Val Thr Val Ser Ser
    130                 135                 140

<210> SEQ ID NO 26
<211> LENGTH: 121
<212> TYPE: PRT
<213> ORGANISM: Artificial Sequence
<220> FEATURE:
<223> OTHER INFORMATION: Synthetic VH region of anti-TNF alpha antibody

<400> SEQUENCE: 26

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45
```

```
Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
                100                 105                 110

Gln Gly Thr Leu Val Thr Val Ser Ser
        115                 120

<210> SEQ ID NO 27
<211> LENGTH: 387
<212> TYPE: DNA
<213> ORGANISM: Artificial Sequence
<220> FEATURE:
<223> OTHER INFORMATION: Synthetic VL region of anti-TNF alpha antibody
<220> FEATURE:
<221> NAME/KEY: CDS
<222> LOCATION: (1)..(387)

<400> SEQUENCE: 27 atg gac atg agg gtc ccc gct cag ctc ctg ggg ctt ctg ctg ctc tgg    48
Met Asp Met Arg Val Pro Ala Gln Leu Leu Gly Leu Leu Leu Leu Trp
1               5                   10                  15 ctc cca ggt gcc aga tgt gac atc cag atg acc cag tct cca tcc tcc    96
Leu Pro Gly Ala Arg Cys Asp Ile Gln Met Thr Gln Ser Pro Ser Ser
            20                  25                  30 ctg tct gca tct gta ggg gac aga gtc acc atc act tgt cgg gca agt   144
Leu Ser Ala Ser Val Gly Asp Arg Val Thr Ile Thr Cys Arg Ala Ser
        35                  40                  45 cag ggc atc aga aat tac tta gcc tgg tat cag caa aaa cca ggg aaa   192
Gln Gly Ile Arg Asn Tyr Leu Ala Trp Tyr Gln Gln Lys Pro Gly Lys
    50                  55                  60 gcc cct aag ctc ctg atc tat gct gca tcc act ttg caa tca ggg gtc   240
Ala Pro Lys Leu Leu Ile Tyr Ala Ala Ser Thr Leu Gln Ser Gly Val
65                  70                  75                  80 cca tct cgg ttc agt ggc agt gga tct ggg aca gat ttc act ctc acc   288
Pro Ser Arg Phe Ser Gly Ser Gly Ser Gly Thr Asp Phe Thr Leu Thr
                85                  90                  95 atc agc agc cta cag cct gaa gat gtt gca act tat tac tgt caa agg   336
Ile Ser Ser Leu Gln Pro Glu Asp Val Ala Thr Tyr Tyr Cys Gln Arg
            100                 105                 110 tat aac cgt gca ccg tat act ttt ggc cag ggg acc aaa gtg gag atc   384
Tyr Asn Arg Ala Pro Tyr Thr Phe Gly Gln Gly Thr Lys Val Glu Ile
        115                 120                 125 aaa                                                                387
Lys

<210> SEQ ID NO 28
<211> LENGTH: 129
<212> TYPE: PRT
<213> ORGANISM: Artificial Sequence
<220> FEATURE:
<223> OTHER INFORMATION: Synthetic Construct

<400> SEQUENCE: 28

Met Asp Met Arg Val Pro Ala Gln Leu Leu Gly Leu Leu Leu Leu Trp
1               5                   10                  15

Leu Pro Gly Ala Arg Cys Asp Ile Gln Met Thr Gln Ser Pro Ser Ser
            20                  25                  30
```

```
Leu Ser Ala Ser Val Gly Asp Arg Val Thr Ile Thr Cys Arg Ala Ser
        35                  40                  45

Gln Gly Ile Arg Asn Tyr Leu Ala Trp Tyr Gln Gln Lys Pro Gly Lys
 50                  55                  60

Ala Pro Lys Leu Leu Ile Tyr Ala Ala Ser Thr Leu Gln Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Val Ala Thr Tyr Tyr Cys Gln Arg
            100                 105                 110

Tyr Asn Arg Ala Pro Tyr Thr Phe Gly Gln Gly Thr Lys Val Glu Ile
        115                 120                 125

Lys

<210> SEQ ID NO 29
<211> LENGTH: 107
<212> TYPE: PRT
<213> ORGANISM: Artificial Sequence
<220> FEATURE:
<223> OTHER INFORMATION: Synthetic VL region of anti-TNF alpha antibody

<400> SEQUENCE: 29

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
             20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu Ile Lys
            100                 105

<210> SEQ ID NO 30
<211> LENGTH: 420
<212> TYPE: DNA
<213> ORGANISM: Artificial Sequence
<220> FEATURE:
<223> OTHER INFORMATION: Synthetic VH region of anti-CD20 antibody
<220> FEATURE:
<221> NAME/KEY: CDS
<222> LOCATION: (1)..(420)

<400> SEQUENCE: 30 atg ggt tgg agc ctc atc ttg ctc ttc ctt gtc gct gtt gct acg cgt      48
Met Gly Trp Ser Leu Ile Leu Leu Phe Leu Val Ala Val Ala Thr Arg
 1               5                  10                  15 gtc ctg tcc cag gta caa ctg cag cag cct ggg gct gag ctg gtg aag      96
Val Leu Ser Gln Val Gln Leu Gln Gln Pro Gly Ala Glu Leu Val Lys
             20                  25                  30 cct ggg gcc tca gtg aag atg tcc tgc aag gct tct ggc tac aca ttt     144
Pro Gly Ala Ser Val Lys Met Ser Cys Lys Ala Ser Gly Tyr Thr Phe
         35                  40                  45 acc agt tac aat atg cac tgg gta aaa cag aca cct ggt cgg ggc ctg     192
Thr Ser Tyr Asn Met His Trp Val Lys Gln Thr Pro Gly Arg Gly Leu
 50                  55                  60
```

```
gaa tgg att gga gct att tat ccc gga aat ggt gat act tcc tac aat      240
Glu Trp Ile Gly Ala Ile Tyr Pro Gly Asn Gly Asp Thr Ser Tyr Asn
65              70                  75                  80 cag aag ttc aaa ggc aag gcc aca ttg act gca gac aaa tcc tcc agc      288
Gln Lys Phe Lys Gly Lys Ala Thr Leu Thr Ala Asp Lys Ser Ser Ser
            85                  90                  95 aca gcc tac atg cag ctc agc agc ctg aca tct gag gac tct gcg gtc      336
Thr Ala Tyr Met Gln Leu Ser Ser Leu Thr Ser Glu Asp Ser Ala Val
            100                 105                 110 tat tac tgt gca aga tcg act tac tac ggc ggt gac tgg tac ttc aat      384
Tyr Tyr Cys Ala Arg Ser Thr Tyr Tyr Gly Gly Asp Trp Tyr Phe Asn
            115                 120                 125 gtc tgg ggc gca ggg acc acg gtc acc gtc tct gca                      420
Val Trp Gly Ala Gly Thr Thr Val Thr Val Ser Ala
130             135                 140

<210> SEQ ID NO 31
<211> LENGTH: 140
<212> TYPE: PRT
<213> ORGANISM: Artificial Sequence
<220> FEATURE:
<223> OTHER INFORMATION: Synthetic Construct

<400> SEQUENCE: 31

Met Gly Trp Ser Leu Ile Leu Leu Phe Leu Val Ala Val Ala Thr Arg
1               5                   10                  15

Val Leu Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65              70                  75                  80

Gln Lys Phe Lys Gly Lys Ala Thr Leu Thr Ala Asp Lys Ser Ser Ser
            85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
            115                 120                 125

Val Trp Gly Ala Gly Thr Thr Val Thr Val Ser Ala
130             135                 140

<210> SEQ ID NO 32
<211> LENGTH: 121
<212> TYPE: PRT
<213> ORGANISM: Artificial Sequence
<220> FEATURE:
<223> OTHER INFORMATION: Synthetic VH region of anti-CD20 antibody

<400> SEQUENCE: 32

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60
```

```
Lys Gly Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser Thr Tyr Tyr Gly Asp Trp Tyr Phe Asn Val Trp Gly
            100                 105                 110

Ala Gly Thr Thr Val Thr Val Ser Ala
        115                 120

<210> SEQ ID NO 33
<211> LENGTH: 384
<212> TYPE: DNA
<213> ORGANISM: Artificial Sequence
<220> FEATURE:
<223> OTHER INFORMATION: Synthetic VL region of anti-CD20 antibody
<220> FEATURE:
<221> NAME/KEY: CDS
<222> LOCATION: (1)..(384)

<400> SEQUENCE: 33
```

| atg gat ttt cag gtg cag att atc agc ttc ctg cta atc agt gct tca | 48 |
|---|---|
| Met Asp Phe Gln Val Gln Ile Ile Ser Phe Leu Leu Ile Ser Ala Ser | |
| 1               5                   10                  15 | |

| gtc ata atg tcc aga gga caa att gtt ctc tcc cag tct cca gca atc | 96 |
|---|---|
| Val Ile Met Ser Arg Gly Gln Ile Val Leu Ser Gln Ser Pro Ala Ile | |
|             20                  25                  30 | |

| ctg tct gca tct cca ggg gag aag gtc aca atg act tgc agg gcc agc | 144 |
|---|---|
| Leu Ser Ala Ser Pro Gly Glu Lys Val Thr Met Thr Cys Arg Ala Ser | |
|         35                  40                  45 | |

| tca agt gta agt tac atc cac tgg ttc cag cag aag cca gga tcc tcc | 192 |
|---|---|
| Ser Ser Val Ser Tyr Ile His Trp Phe Gln Gln Lys Pro Gly Ser Ser | |
|     50                  55                  60 | |

| ccc aaa ccc tgg att tat gcc aca tcc aac ctg gct tct gga gtc cct | 240 |
|---|---|
| Pro Lys Pro Trp Ile Tyr Ala Thr Ser Asn Leu Ala Ser Gly Val Pro | |
| 65                  70                  75                  80 | |

| gtt cgc ttc agt ggc agt ggg tct ggg act tct tac tct ctc aca atc | 288 |
|---|---|
| Val Arg Phe Ser Gly Ser Gly Ser Gly Thr Ser Tyr Ser Leu Thr Ile | |
|                 85                  90                  95 | |

| agc aga gtg gag gct gaa gat gct gcc act tat tac tgc cag cag tgg | 336 |
|---|---|
| Ser Arg Val Glu Ala Glu Asp Ala Ala Thr Tyr Tyr Cys Gln Gln Trp | |
|             100                 105                 110 | |

| act agt aac cca ccc acg ttc gga ggg ggg acc aag ctg gaa atc aaa | 384 |
|---|---|
| Thr Ser Asn Pro Pro Thr Phe Gly Gly Gly Thr Lys Leu Glu Ile Lys | |
|         115                 120                 125 | |

```
<210> SEQ ID NO 34
<211> LENGTH: 128
<212> TYPE: PRT
<213> ORGANISM: Artificial Sequence
<220> FEATURE:
<223> OTHER INFORMATION: Synthetic Construct

<400> SEQUENCE: 34

Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Ile His Trp Phe Gln Gln Lys Pro Gly Ser Ser
    50                  55                  60
```

```
Pro Lys Pro Trp Ile Tyr Ala Thr Ser Asn Leu Ala Ser Gly Val Pro
 65                  70                  75                  80

Val Arg Phe Ser Gly Ser Gly Ser Gly Thr Ser Tyr Ser Leu Thr Ile
                 85                  90                  95

Ser Arg Val Glu Ala Glu Asp Ala Ala Thr Tyr Tyr Cys Gln Gln Trp
            100                 105                 110

Thr Ser Asn Pro Pro Thr Phe Gly Gly Gly Thr Lys Leu Glu Ile Lys
        115                 120                 125

<210> SEQ ID NO 35
<211> LENGTH: 106
<212> TYPE: PRT
<213> ORGANISM: Artificial Sequence
<220> FEATURE:
<223> OTHER INFORMATION: Synthetic VL region of anti-CD20 antibody

<400> SEQUENCE: 35

Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 36
<211> LENGTH: 795
<212> TYPE: DNA
<213> ORGANISM: unknown
<220> FEATURE:
<223> OTHER INFORMATION: wild type neomycin resistant gene
<220> FEATURE:
<221> NAME/KEY: CDS
<222> LOCATION: (1)..(795)

<400> SEQUENCE: 36 atg att gaa caa gat gga ttg cac gca ggt tct ccg gcc gct tgg gtg     48
Met Ile Glu Gln Asp Gly Leu His Ala Gly Ser Pro Ala Ala Trp Val
 1               5                  10                  15 gag agg cta ttc ggc tat gac tgg gca caa cag aca atc ggc tgc tct     96
Glu Arg Leu Phe Gly Tyr Asp Trp Ala Gln Gln Thr Ile Gly Cys Ser
                20                  25                  30 gat gcc gcc gtg ttc cgg ctg tca gcg cag ggg cgc ccg gtt ctt ttt    144
Asp Ala Ala Val Phe Arg Leu Ser Ala Gln Gly Arg Pro Val Leu Phe
            35                  40                  45 gtc aag acc gac ctg tcc ggt gcc ctg aat gaa ctg cag gac gag gca    192
Val Lys Thr Asp Leu Ser Gly Ala Leu Asn Glu Leu Gln Asp Glu Ala
        50                  55                  60 gcg cgg cta tcg tgg ctg gcc acg acg ggc gtt cct tgc gca gct gtg    240
Ala Arg Leu Ser Trp Leu Ala Thr Thr Gly Val Pro Cys Ala Ala Val
 65                  70                  75                  80 ctc gac gtt gtc act gaa gcg gga agg gac tgg ctg cta ttg ggc gaa    288
Leu Asp Val Val Thr Glu Ala Gly Arg Asp Trp Leu Leu Leu Gly Glu
```

```
gtg ccg ggg cag gat ctc ctg tca tct cac ctt gct cct gcc gag aaa     336
Val Pro Gly Gln Asp Leu Leu Ser Ser His Leu Ala Pro Ala Glu Lys
            100                 105                 110 gta tcc atc atg gct gat gca atg cgg cgg ctg cat acg ctt gat ccg     384
Val Ser Ile Met Ala Asp Ala Met Arg Arg Leu His Thr Leu Asp Pro
            115                 120                 125 gct acc tgc cca ttc gac cac caa gcg aaa cat cgc atc gag cga gca     432
Ala Thr Cys Pro Phe Asp His Gln Ala Lys His Arg Ile Glu Arg Ala
        130                 135                 140 cgt act cgg atg gaa gcc ggt ctt gtc gat cag gat gat ctg gac gaa     480
Arg Thr Arg Met Glu Ala Gly Leu Val Asp Gln Asp Asp Leu Asp Glu
145                 150                 155                 160 gag cat cag ggg ctc gcg cca gcc gaa ctg ttc gcc agg ctc aag gcg     528
Glu His Gln Gly Leu Ala Pro Ala Glu Leu Phe Ala Arg Leu Lys Ala
                165                 170                 175 cgc atg ccc gac ggc gag gat ctc gtc gtg acc cat ggc gat gcc tgc     576
Arg Met Pro Asp Gly Glu Asp Leu Val Val Thr His Gly Asp Ala Cys
            180                 185                 190 ttg ccg aat atc atg gtg gaa aat ggc cgc ttt tct gga ttc atc gac     624
Leu Pro Asn Ile Met Val Glu Asn Gly Arg Phe Ser Gly Phe Ile Asp
        195                 200                 205 tgt ggc cgg ctg ggt gtg gcg gac cgc tat cag gac ata gcg ttg gct     672
Cys Gly Arg Leu Gly Val Ala Asp Arg Tyr Gln Asp Ile Ala Leu Ala
210                 215                 220 acc cgt gat att gct gaa gag ctt ggc ggc gaa tgg gct gac cgc ttc     720
Thr Arg Asp Ile Ala Glu Glu Leu Gly Gly Glu Trp Ala Asp Arg Phe
225                 230                 235                 240 ctc gtg ctt tac ggt atc gcc gct ccc gat tcg cag cgc atc gcc ttc     768
Leu Val Leu Tyr Gly Ile Ala Ala Pro Asp Ser Gln Arg Ile Ala Phe
                245                 250                 255 tat cgc ctt ctt gac gag ttc ttc tga                                 795
Tyr Arg Leu Leu Asp Glu Phe Phe
            260

<210> SEQ ID NO 37
<211> LENGTH: 795
<212> TYPE: DNA
<213> ORGANISM: Artificial Sequence
<220> FEATURE:
<223> OTHER INFORMATION: Synthetic modified neomycin resistant gene
<220> FEATURE:
<221> NAME/KEY: CDS
<222> LOCATION: (1)..(795)

<400> SEQUENCE: 37 atg att gaa caa gat gga ttg cac gca ggt tct ccg gcc gct tgg gtg      48
Met Ile Glu Gln Asp Gly Leu His Ala Gly Ser Pro Ala Ala Trp Val
1               5                   10                  15 gag agg cta ttc ggc tat gac tgg gca caa cag aca atc ggc tgc tct      96
Glu Arg Leu Phe Gly Tyr Asp Trp Ala Gln Gln Thr Ile Gly Cys Ser
            20                  25                  30 gat gcc gcc gtg ttc cgg ctg tca gcg cag ggg cgc ccg gtt ctt ttt     144
Asp Ala Ala Val Phe Arg Leu Ser Ala Gln Gly Arg Pro Val Leu Phe
        35                  40                  45 gtc aag acc gac ctg tcc ggt gcc ctg aat gaa ctg caa gat gaa gcg     192
Val Lys Thr Asp Leu Ser Gly Ala Leu Asn Glu Leu Gln Asp Glu Ala
    50                  55                  60 gcg cga tta tcg tgg tta gcg acg acg ggg gta ccg tgt gcg gcg gta     240
Ala Arg Leu Ser Trp Leu Ala Thr Thr Gly Val Pro Cys Ala Ala Val
65                  70                  75                  80
```

-continued

| | | |
|---|---|---|
| tta gat gta gta acg gaa gcg ggg cga gat tgg tta tta ggg gaa<br>Leu Asp Val Val Thr Glu Ala Gly Arg Asp Trp Leu Leu Leu Gly Glu<br>                          85                        90                        95 | 288 | |
| gta ccg ggg caa gat tta tta tcg tcg cat tta gcg ccg gcg gaa aaa<br>Val Pro Gly Gln Asp Leu Leu Ser Ser His Leu Ala Pro Ala Glu Lys<br>                     100                    105                   110 | 336 | |
| gta tcg ata atg gcg gat gcg atg cga cga tta cat acg tta gat ccg<br>Val Ser Ile Met Ala Asp Ala Met Arg Arg Leu His Thr Leu Asp Pro<br>                  115                    120                   125 | 384 | |
| gcg acg tgt ccg ttt gat cat caa gcg aaa cat cga ata gaa cga gcg<br>Ala Thr Cys Pro Phe Asp His Gln Ala Lys His Arg Ile Glu Arg Ala<br>130                          135                    140 | 432 | |
| cga acg cga atg gaa gcg ggg tta gta gat caa gat gat tta gat gaa<br>Arg Thr Arg Met Glu Ala Gly Leu Val Asp Gln Asp Asp Leu Asp Glu<br>145                        150                    155                   160 | 480 | |
| gaa cat caa ggg tta gcg ccg gcg gaa tta ttt gcg cga tta aaa gcg<br>Glu His Gln Gly Leu Ala Pro Ala Glu Leu Phe Ala Arg Leu Lys Ala<br>                     165                    170                   175 | 528 | |
| cga atg ccg gat ggg gaa gat tta gta gta acg cat ggg gat gcg tgt<br>Arg Met Pro Asp Gly Glu Asp Leu Val Val Thr His Gly Asp Ala Cys<br>                  180                    185                   190 | 576 | |
| tta ccg aat ata atg gta gaa aat ggg cga ttt tcg ggg ttt ata gat<br>Leu Pro Asn Ile Met Val Glu Asn Gly Arg Phe Ser Gly Phe Ile Asp<br>                  195                    200                   205 | 624 | |
| tgt ggg cga tta ggg gta gcg gat cgt tat caa gat ata gcg tta gcg<br>Cys Gly Arg Leu Gly Val Ala Asp Arg Tyr Gln Asp Ile Ala Leu Ala<br>            210                    215                   220 | 672 | |
| acg cga gat ata gcg gaa gaa tta ggg ggg gaa tgg gcg gat cga ttt<br>Thr Arg Asp Ile Ala Glu Glu Leu Gly Gly Glu Trp Ala Asp Arg Phe<br>225                        230                    235                   240 | 720 | |
| tta gta tta tat ggg ata gcg gcg ccg gat tcg caa cga ata gcg ttt<br>Leu Val Leu Tyr Gly Ile Ala Ala Pro Asp Ser Gln Arg Ile Ala Phe<br>                     245                    250                   255 | 768 | |
| tat cga tta tta gat gaa ttt ttt tga<br>Tyr Arg Leu Leu Asp Glu Phe Phe<br>            260 | 795 | |

<210> SEQ ID NO 38
<211> LENGTH: 795
<212> TYPE: DNA
<213> ORGANISM: Artificial Sequence
<220> FEATURE:
<223> OTHER INFORMATION: Synthetic modified neomycin resistant gene
<220> FEATURE:
<221> NAME/KEY: CDS
<222> LOCATION: (1)..(795)

<400> SEQUENCE: 38

| | | |
|---|---|---|
| atg att gaa caa gat gga ttg cac gca ggt tct ccg gcc gct tgg gtg<br>Met Ile Glu Gln Asp Gly Leu His Ala Gly Ser Pro Ala Ala Trp Val<br>1                      5                      10                      15 | 48 | |
| gag agg cta ttc ggc tat gac tgg gca caa cag aca atc ggc tgc tct<br>Glu Arg Leu Phe Gly Tyr Asp Trp Ala Gln Gln Thr Ile Gly Cys Ser<br>                   20                    25                    30 | 96 | |
| gat gcc gcc gtg ttc cgg ctg tca gcg cag ggg cgc ccg gtt ctt ttt<br>Asp Ala Ala Val Phe Arg Leu Ser Ala Gln Gly Arg Pro Val Leu Phe<br>              35                    40                    45 | 144 | |
| gta aaa acg gat tta tcg ggg gcg tta aat gaa tta caa gat gaa gcg<br>Val Lys Thr Asp Leu Ser Gly Ala Leu Asn Glu Leu Gln Asp Glu Ala<br>            50                    55                    60 | 192 | |
| gcg cga tta tcg tgg tta gcg acg acg ggg gta ccg tgt gcg gcg gta<br>Ala Arg Leu Ser Trp Leu Ala Thr Thr Gly Val Pro Cys Ala Ala Val | 240 | |

```
                65                  70                  75                  80
tta gat gta gta acg gaa gcg ggg cga gat tgg tta tta ggg gaa      288
Leu Asp Val Val Thr Glu Ala Gly Arg Asp Trp Leu Leu Gly Glu
                    85                  90                  95 gta ccg ggg caa gat tta tta tcg tcg cat tta gcg ccg gcg gaa aaa  336
Val Pro Gly Gln Asp Leu Leu Ser Ser His Leu Ala Pro Ala Glu Lys
            100                 105                 110 gta tcg ata atg gcg gat gcg atg cga cga tta cat acg tta gat ccg  384
Val Ser Ile Met Ala Asp Ala Met Arg Arg Leu His Thr Leu Asp Pro
        115                 120                 125 gcg acg tgt ccg ttt gat cat caa gcg aaa cat cga ata gaa cga gcg  432
Ala Thr Cys Pro Phe Asp His Gln Ala Lys His Arg Ile Glu Arg Ala
    130                 135                 140 cga acg cga atg gaa gcg ggg tta gta gat caa gat gat tta gat gaa  480
Arg Thr Arg Met Glu Ala Gly Leu Val Asp Gln Asp Asp Leu Asp Glu
145                 150                 155                 160 gaa cat caa ggg tta gcg ccg gcg gaa tta ttt gcg cga tta aaa gcg  528
Glu His Gln Gly Leu Ala Pro Ala Glu Leu Phe Ala Arg Leu Lys Ala
                    165                 170                 175 cga atg ccg gat ggg gaa gat tta gta gta acg cat ggg gat gcg tgt  576
Arg Met Pro Asp Gly Glu Asp Leu Val Val Thr His Gly Asp Ala Cys
            180                 185                 190 tta ccg aat ata atg gta gaa aat ggg cga ttt tcg ggg ttt ata gat  624
Leu Pro Asn Ile Met Val Glu Asn Gly Arg Phe Ser Gly Phe Ile Asp
        195                 200                 205 tgt ggg cga tta ggg gta gcg gat cgt tat caa gat ata gcg tta gcg  672
Cys Gly Arg Leu Gly Val Ala Asp Arg Tyr Gln Asp Ile Ala Leu Ala
    210                 215                 220 acg cga gat ata gcg gaa gaa tta ggg ggg gaa tgg gcg gat cga ttt  720
Thr Arg Asp Ile Ala Glu Glu Leu Gly Gly Glu Trp Ala Asp Arg Phe
225                 230                 235                 240 tta gta tta tat ggg ata gcg gcg ccg gat tcg caa cga ata gcg ttt  768
Leu Val Leu Tyr Gly Ile Ala Ala Pro Asp Ser Gln Arg Ile Ala Phe
                    245                 250                 255 tat cga tta tta gat gaa ttt ttt tga                              795
Tyr Arg Leu Leu Asp Glu Phe Phe
                    260

<210> SEQ ID NO 39
<211> LENGTH: 795
<212> TYPE: DNA
<213> ORGANISM: Artificial Sequence
<220> FEATURE:
<223> OTHER INFORMATION: Synthetic modified neomycin resistant gene
<220> FEATURE:
<221> NAME/KEY: CDS
<222> LOCATION: (1)..(795)

<400> SEQUENCE: 39 atg att gaa caa gat gga ttg cac gca ggt tct ccg gcc gct tgg gtg  48
Met Ile Glu Gln Asp Gly Leu His Ala Gly Ser Pro Ala Ala Trp Val
1               5                   10                  15 gag agg cta ttt ggg tat gat tgg gcg caa caa acg ata ggg tgt tcg  96
Glu Arg Leu Phe Gly Tyr Asp Trp Ala Gln Gln Thr Ile Gly Cys Ser
                20                  25                  30 gat gcg gcg gta ttt cga tta tcg gcg caa ggg cga ccg gta tta ttt  144
Asp Ala Ala Val Phe Arg Leu Ser Ala Gln Gly Arg Pro Val Leu Phe
            35                  40                  45 gta aaa acg gat tta tcg ggg gcg tta aat gaa tta caa gat gaa gcg  192
Val Lys Thr Asp Leu Ser Gly Ala Leu Asn Glu Leu Gln Asp Glu Ala
        50                  55                  60
```

```
gcg cga tta tcg tgg tta gcg acg acg ggg gta ccg tgt gcg gcg gta        240
Ala Arg Leu Ser Trp Leu Ala Thr Thr Gly Val Pro Cys Ala Ala Val
 65              70                  75                  80 tta gat gta gta acg gaa gcg ggg cga gat tgg tta tta ggg gaa            288
Leu Asp Val Val Thr Glu Ala Gly Arg Asp Trp Leu Leu Leu Gly Glu
                 85                  90                  95 gta ccg ggg caa gat tta tta tcg tcg cat tta gcg ccg gcg gaa aaa        336
Val Pro Gly Gln Asp Leu Leu Ser Ser His Leu Ala Pro Ala Glu Lys
            100                 105                 110 gta tcg ata atg gcg gat gcg atg cga cga tta cat acg tta gat ccg        384
Val Ser Ile Met Ala Asp Ala Met Arg Arg Leu His Thr Leu Asp Pro
        115                 120                 125 gcg acg tgt ccg ttt gat cat caa gcg aaa cat cga ata gaa cga gcg        432
Ala Thr Cys Pro Phe Asp His Gln Ala Lys His Arg Ile Glu Arg Ala
    130                 135                 140 cga acg cga atg gaa gcg ggg tta gta gat caa gat gat tta gat gaa        480
Arg Thr Arg Met Glu Ala Gly Leu Val Asp Gln Asp Asp Leu Asp Glu
145                 150                 155                 160 gaa cat caa ggg tta gcg ccg gcg gaa tta ttt gcg cga tta aaa gcg        528
Glu His Gln Gly Leu Ala Pro Ala Glu Leu Phe Ala Arg Leu Lys Ala
                165                 170                 175 cga atg ccg gat ggg gaa gat tta gta gta acg cat ggg gat gcg tgt        576
Arg Met Pro Asp Gly Glu Asp Leu Val Val Thr His Gly Asp Ala Cys
            180                 185                 190 tta ccg aat ata atg gta gaa aat ggg cga ttt tcg ggg ttt ata gat        624
Leu Pro Asn Ile Met Val Glu Asn Gly Arg Phe Ser Gly Phe Ile Asp
        195                 200                 205 tgt ggg cga tta ggg gta gcg gat cgt tat caa gat ata gcg tta gcg        672
Cys Gly Arg Leu Gly Val Ala Asp Arg Tyr Gln Asp Ile Ala Leu Ala
    210                 215                 220 acg cga gat ata gcg gaa gaa tta ggg ggg gaa tgg gcg gat cga ttt        720
Thr Arg Asp Ile Ala Glu Glu Leu Gly Gly Glu Trp Ala Asp Arg Phe
225                 230                 235                 240 tta gta tta tat ggg ata gcg gcg ccg gat tcg caa cga ata gcg ttt        768
Leu Val Leu Tyr Gly Ile Ala Ala Pro Asp Ser Gln Arg Ile Ala Phe
                245                 250                 255 tat cga tta tta gat gaa ttt ttt tga                                    795
Tyr Arg Leu Leu Asp Glu Phe Phe
            260

<210> SEQ ID NO 40
<211> LENGTH: 649
<212> TYPE: PRT
<213> ORGANISM: Oryzias latipes

<400> SEQUENCE: 40

Met Glu Glu Val Cys Asp Ser Ser Ala Ala Ser Ser Thr Val Gln
1               5                  10                  15

Asn Gln Pro Gln Asp Gln Glu His Pro Trp Pro Tyr Leu Arg Glu Phe
            20                  25                  30

Phe Ser Leu Ser Gly Val Asn Lys Asp Ser Phe Lys Met Lys Cys Val
        35                  40                  45

Leu Cys Leu Pro Leu Asn Lys Glu Ile Ser Ala Phe Lys Ser Ser Pro
    50                  55                  60

Ser Asn Leu Arg Lys His Ile Glu Arg Met His Pro Asn Tyr Leu Lys
65                  70                  75                  80

Asn Tyr Ser Lys Leu Thr Ala Gln Lys Arg Lys Ile Gly Thr Ser Thr
                85                  90                  95

His Ala Ser Ser Ser Lys Gln Leu Lys Val Asp Ser Val Phe Pro Val
```

```
                100                 105                 110
Lys His Val Ser Pro Val Thr Val Asn Lys Ala Ile Leu Arg Tyr Ile
            115                 120                 125

Ile Gln Gly Leu His Pro Phe Ser Thr Val Asp Leu Pro Ser Phe Lys
        130                 135                 140

Glu Leu Ile Ser Thr Leu Gln Pro Gly Ile Ser Val Ile Thr Arg Pro
145                 150                 155                 160

Thr Leu Arg Ser Lys Ile Ala Glu Ala Leu Ile Met Lys Gln Lys
                165                 170                 175

Val Thr Ala Ala Met Ser Glu Val Glu Trp Ile Ala Thr Thr Thr Asp
            180                 185                 190

Cys Trp Thr Ala Arg Arg Lys Ser Phe Ile Gly Val Thr Ala His Trp
        195                 200                 205

Ile Asn Pro Gly Ser Leu Glu Arg His Ser Ala Ala Leu Ala Cys Lys
    210                 215                 220

Arg Leu Met Gly Ser His Thr Phe Glu Val Leu Ala Ser Ala Met Asn
225                 230                 235                 240

Asp Ile His Ser Glu Tyr Glu Ile Arg Asp Lys Val Val Cys Thr Thr
                245                 250                 255

Thr Asp Ser Gly Ser Asn Phe Met Lys Ala Phe Arg Val Phe Gly Val
            260                 265                 270

Glu Asn Asn Asp Ile Glu Thr Glu Ala Arg Arg Cys Glu Ser Asp Asp
        275                 280                 285

Thr Asp Ser Glu Gly Cys Gly Glu Gly Ser Asp Gly Val Glu Phe Gln
    290                 295                 300

Asp Ala Ser Arg Val Leu Asp Gln Asp Asp Gly Phe Glu Phe Gln Leu
305                 310                 315                 320

Pro Lys His Gln Lys Cys Ala Cys His Leu Leu Asn Leu Val Ser Ser
                325                 330                 335

Val Asp Ala Gln Lys Ala Leu Ser Asn Glu His Tyr Lys Lys Leu Tyr
            340                 345                 350

Arg Ser Val Phe Gly Lys Cys Gln Ala Leu Trp Asn Lys Ser Ser Arg
        355                 360                 365

Ser Ala Leu Ala Ala Glu Ala Val Glu Ser Glu Ser Arg Leu Gln Leu
    370                 375                 380

Leu Arg Pro Asn Gln Thr Arg Trp Asn Ser Thr Phe Met Ala Val Asp
385                 390                 395                 400

Arg Ile Leu Gln Ile Cys Lys Glu Ala Gly Glu Gly Ala Leu Arg Asn
                405                 410                 415

Ile Cys Thr Ser Leu Glu Val Pro Met Phe Asn Pro Ala Glu Met Leu
            420                 425                 430

Phe Leu Thr Glu Trp Ala Asn Thr Met Arg Pro Val Ala Lys Val Leu
        435                 440                 445

Asp Ile Leu Gln Ala Glu Thr Asn Thr Gln Leu Gly Trp Leu Leu Pro
    450                 455                 460

Ser Val His Gln Leu Ser Leu Lys Leu Gln Arg Leu His His Ser Leu
465                 470                 475                 480

Arg Tyr Cys Asp Pro Leu Val Asp Ala Leu Gln Gln Gly Ile Gln Thr
                485                 490                 495

Arg Phe Lys His Met Phe Glu Asp Pro Glu Ile Ile Ala Ala Ala Ile
            500                 505                 510

Leu Leu Pro Lys Phe Arg Thr Ser Trp Thr Asn Asp Glu Thr Ile Ile
        515                 520                 525
```

```
Lys Arg Gly Met Asp Tyr Ile Arg Val His Leu Glu Pro Leu Asp His
        530                 535                 540

Lys Lys Glu Leu Ala Asn Ser Ser Asp Asp Glu Asp Phe Phe Ala
545                 550                 555                 560

Ser Leu Lys Pro Thr Thr His Glu Ala Ser Lys Glu Leu Asp Gly Tyr
            565                 570                 575

Leu Ala Cys Val Ser Asp Thr Arg Glu Ser Leu Leu Thr Phe Pro Ala
        580                 585                 590

Ile Cys Ser Leu Ser Ile Lys Thr Asn Thr Pro Leu Pro Ala Ser Ala
    595                 600                 605

Ala Cys Glu Arg Leu Phe Ser Thr Ala Gly Leu Leu Phe Ser Pro Lys
610                 615                 620

Arg Ala Arg Leu Asp Thr Asn Asn Phe Glu Asn Gln Leu Leu Leu Lys
625                 630                 635                 640

Leu Asn Leu Arg Phe Tyr Asn Phe Glu
                645

<210> SEQ ID NO 41
<211> LENGTH: 600
<212> TYPE: DNA
<213> ORGANISM: Artificial Sequence
<220> FEATURE:
<223> OTHER INFORMATION: Synthetic modified puromycin resistant gene
<220> FEATURE:
<221> NAME/KEY: CDS
<222> LOCATION: (1)..(600)

<400> SEQUENCE: 41 atg acg gaa tat aaa ccg acg gta cgt tta gcg acg cgt gat gat gta      48
Met Thr Glu Tyr Lys Pro Thr Val Arg Leu Ala Thr Arg Asp Asp Val
1               5                   10                  15 ccg cgt gcg gta cgt acg tta gcg gcg gcg ttt gcg gat tat ccg gcg     96
Pro Arg Ala Val Arg Thr Leu Ala Ala Ala Phe Ala Asp Tyr Pro Ala
            20                  25                  30 acg cgt cat acg gta gat ccg gat cgt cat ata gaa cgt gta acg gaa    144
Thr Arg His Thr Val Asp Pro Asp Arg His Ile Glu Arg Val Thr Glu
        35                  40                  45 tta caa gaa tta ttt tta acg cgt gta ggt tta gat ata ggt aaa gta    192
Leu Gln Glu Leu Phe Leu Thr Arg Val Gly Leu Asp Ile Gly Lys Val
    50                  55                  60 tgg gta gcg gat gat ggt gcg gcg gta gcg gta tgg acg acg ccg gaa    240
Trp Val Ala Asp Asp Gly Ala Ala Val Ala Val Trp Thr Thr Pro Glu
65                  70                  75                  80 tcg gta gaa gcg ggt gcg gta ttt gcg gaa ata ggt ccg cgt atg gcg    288
Ser Val Glu Ala Gly Ala Val Phe Ala Glu Ile Gly Pro Arg Met Ala
                85                  90                  95 gaa tta tcg ggt tcg cgt tta gcg gcg caa caa caa atg gaa ggt tta    336
Glu Leu Ser Gly Ser Arg Leu Ala Ala Gln Gln Gln Met Glu Gly Leu
            100                 105                 110 tta gcg ccg cat cgt ccg aaa gaa ccg gcg tgg ttt tta gcg acg gta    384
Leu Ala Pro His Arg Pro Lys Glu Pro Ala Trp Phe Leu Ala Thr Val
        115                 120                 125 ggt gta tcg ccg gat cat caa ggt aaa ggt tta ggt tcg gcg gta gta    432
Gly Val Ser Pro Asp His Gln Gly Lys Gly Leu Gly Ser Ala Val Val
    130                 135                 140 tta ccg ggt gta gaa gcg gcg gaa cgt gcg ggt gta ccg gcg ttt tta    480
Leu Pro Gly Val Glu Ala Ala Glu Arg Ala Gly Val Pro Ala Phe Leu
145                 150                 155                 160 gaa acg tcg gcg ccg cgt aat tta ccg ttt tat gaa cgt tta ggt ttt    528
```

```
Glu Thr Ser Ala Pro Arg Asn Leu Pro Phe Tyr Glu Arg Leu Gly Phe
            165                 170                 175 acg gta acg gcg gat gta gaa gta ccg gaa ggt ccg cgt acg tgg tgt      576
Thr Val Thr Ala Asp Val Glu Val Pro Glu Gly Pro Arg Thr Trp Cys
        180                 185                 190 atg acg cgt aaa ccg ggt gcg tga                                      600
Met Thr Arg Lys Pro Gly Ala
            195

<210> SEQ ID NO 42
<211> LENGTH: 600
<212> TYPE: DNA
<213> ORGANISM: unknown
<220> FEATURE:
<223> OTHER INFORMATION: wild type puromycin resistant gene
<220> FEATURE:
<221> NAME/KEY: CDS
<222> LOCATION: (1)..(600)

<400> SEQUENCE: 42 atg acc gag tac aag ccc acg gtg cgc ctc gcc acc cgc gac gac gtc       48
Met Thr Glu Tyr Lys Pro Thr Val Arg Leu Ala Thr Arg Asp Asp Val
1               5                   10                  15 ccc cgg gcc gta cgc acc ctc gcc gcc gcg ttc gcc gac tac ccc gcc       96
Pro Arg Ala Val Arg Thr Leu Ala Ala Ala Phe Ala Asp Tyr Pro Ala
                20                  25                  30 acg cgc cac acc gtc gac ccg gac cgc cac atc gag cgg gtc acc gag      144
Thr Arg His Thr Val Asp Pro Asp Arg His Ile Glu Arg Val Thr Glu
            35                  40                  45 ctg caa gaa ctc ttc ctc acg cgc gtc ggg ctc gac atc ggc aag gtg      192
Leu Gln Glu Leu Phe Leu Thr Arg Val Gly Leu Asp Ile Gly Lys Val
    50                  55                  60 tgg gtc gcg gac gac ggc gcc gcg gtg gcg gtc tgg acc acg ccg gag      240
Trp Val Ala Asp Asp Gly Ala Ala Val Ala Val Trp Thr Thr Pro Glu
65                  70                  75                  80 agc gtc gaa gcg ggg gcg gtg ttc gcc gag atc ggc ccg cgc atg gcc      288
Ser Val Glu Ala Gly Ala Val Phe Ala Glu Ile Gly Pro Arg Met Ala
                85                  90                  95 gag ttg agc ggt tcc cgg ctg gcc gcg cag caa cag atg gaa ggc ctc      336
Glu Leu Ser Gly Ser Arg Leu Ala Ala Gln Gln Gln Met Glu Gly Leu
            100                 105                 110 ctg gcg ccg cac cgg ccc aag gag ccc gcg tgg ttc ctg gcc acc gtc      384
Leu Ala Pro His Arg Pro Lys Glu Pro Ala Trp Phe Leu Ala Thr Val
        115                 120                 125 ggc gtc tcg ccc gac cac cag ggc aag ggt ctg ggc agc gcc gtc gtg      432
Gly Val Ser Pro Asp His Gln Gly Lys Gly Leu Gly Ser Ala Val Val
    130                 135                 140 ctc ccc gga gtg gag gcg gcc gag cgc gcc ggg gtg ccc gcc ttc ctg      480
Leu Pro Gly Val Glu Ala Ala Glu Arg Ala Gly Val Pro Ala Phe Leu
145                 150                 155                 160 gag acc tcc gcg ccc cgc aac ctc ccc ttc tac gag cgg ctc ggc ttc      528
Glu Thr Ser Ala Pro Arg Asn Leu Pro Phe Tyr Glu Arg Leu Gly Phe
                165                 170                 175 acc gtc acc gcc gac gtc gag gtg ccc gaa gga ccg cgc acc tgg tgc      576
Thr Val Thr Ala Asp Val Glu Val Pro Glu Gly Pro Arg Thr Trp Cys
            180                 185                 190 atg acc cgc aag ccc ggt gcc tga                                      600
Met Thr Arg Lys Pro Gly Ala
            195

<210> SEQ ID NO 43
<211> LENGTH: 600
```

<212> TYPE: DNA
<213> ORGANISM: Artificial Sequence
<220> FEATURE:
<223> OTHER INFORMATION: Synthetic modified puromycin resistant gene
<220> FEATURE:
<221> NAME/KEY: CDS
<222> LOCATION: (1)..(600)

<400> SEQUENCE: 43

```
atg acc gag tac aag ccc acg gta cgc tta gcg acc cgc gac gac gta        48
Met Thr Glu Tyr Lys Pro Thr Val Arg Leu Ala Thr Arg Asp Asp Val
1               5                   10                  15 ccc cgg gcg gta cgc acc tta gcg gcg gcg ttc gcg gac tac ccc gcg        96
Pro Arg Ala Val Arg Thr Leu Ala Ala Ala Phe Ala Asp Tyr Pro Ala
            20                  25                  30 acg cgc cac acc gta gac ccg gac cgc cac atc gag cgg gta acc gag       144
Thr Arg His Thr Val Asp Pro Asp Arg His Ile Glu Arg Val Thr Glu
        35                  40                  45 tta caa gaa tta ttc tta acg cgc gta ggg tta gac atc ggc aag gta       192
Leu Gln Glu Leu Phe Leu Thr Arg Val Gly Leu Asp Ile Gly Lys Val
    50                  55                  60 tgg gta gcg gac gac ggc gcg gcg gta gcg gta tgg acc acg ccg gag       240
Trp Val Ala Asp Asp Gly Ala Ala Val Ala Val Trp Thr Thr Pro Glu
65                  70                  75                  80 tcg gta gaa gcg ggg gcg gta ttc gcg gag atc ggc ccg cgc atg gcg       288
Ser Val Glu Ala Gly Ala Val Phe Ala Glu Ile Gly Pro Arg Met Ala
                85                  90                  95 gag tta tcg ggt tcg cgg tta gcg gcg cag caa cag atg gaa ggc tta       336
Glu Leu Ser Gly Ser Arg Leu Ala Ala Gln Gln Gln Met Glu Gly Leu
            100                 105                 110 tta gcg ccg cac cgg ccc aag gag ccc gcg tgg ttc tta gcg acc gta       384
Leu Ala Pro His Arg Pro Lys Glu Pro Ala Trp Phe Leu Ala Thr Val
        115                 120                 125 ggc gta tcg ccc gac cac cag ggc aag ggt tta ggc tcg gcg gta gta       432
Gly Val Ser Pro Asp His Gln Gly Lys Gly Leu Gly Ser Ala Val Val
    130                 135                 140 tta ccc gga gta gag gcg gcg gag cgc gcg ggg gta ccc gcg ttc tta       480
Leu Pro Gly Val Glu Ala Ala Glu Arg Ala Gly Val Pro Ala Phe Leu
145                 150                 155                 160 gag acc tcg gcg ccc cgc aac tta ccc ttc tac gag cgg tta ggc ttc       528
Glu Thr Ser Ala Pro Arg Asn Leu Pro Phe Tyr Glu Arg Leu Gly Phe
                165                 170                 175 acc gta acc gcg gac gta gag gta ccc gaa gga ccg cgc acc tgg tgc       576
Thr Val Thr Ala Asp Val Glu Val Pro Glu Gly Pro Arg Thr Trp Cys
            180                 185                 190 atg acc cgc aag ccc ggt gcg tga                                       600
Met Thr Arg Lys Pro Gly Ala
        195
```

<210> SEQ ID NO 44
<211> LENGTH: 600
<212> TYPE: DNA
<213> ORGANISM: Artificial Sequence
<220> FEATURE:
<223> OTHER INFORMATION: Synthetic modified puromycin resistant gene
<220> FEATURE:
<221> NAME/KEY: CDS
<222> LOCATION: (1)..(600)

<400> SEQUENCE: 44

```
atg acg gaa tat aaa ccg acg gta cgt tta gcg acg cgt gat gat gta        48
Met Thr Glu Tyr Lys Pro Thr Val Arg Leu Ala Thr Arg Asp Asp Val
1               5                   10                  15
```

```
ccg cgt gcg gta cgt acg tta gcg gcg gcg ttt gcg gat tat ccg gcg      96
Pro Arg Ala Val Arg Thr Leu Ala Ala Ala Phe Ala Asp Tyr Pro Ala
        20                  25                  30 acg cgt cat acg gta gat ccg gat cgt cat ata gaa cgt gta acg gaa     144
Thr Arg His Thr Val Asp Pro Asp Arg His Ile Glu Arg Val Thr Glu
            35                  40                  45 tta caa gaa tta ttt tta acg cgt gta ggt tta gat ata ggt aaa gta     192
Leu Gln Glu Leu Phe Leu Thr Arg Val Gly Leu Asp Ile Gly Lys Val
 50                  55                  60 tgg gta gcg gat gat ggt gcg gcg gcg gta tgg acg acg ccg gaa         240
Trp Val Ala Asp Asp Gly Ala Ala Ala Val Trp Thr Thr Pro Glu
 65                  70                  75                  80 tcg gta gaa gcg ggt gcg gta ttt gcg gaa ata ggt ccg cgt atg gcg     288
Ser Val Glu Ala Gly Ala Val Phe Ala Glu Ile Gly Pro Arg Met Ala
                 85                  90                  95 gaa tta tcg ggt tcg cgt tta gcg gcg caa caa caa atg gaa ggt tta     336
Glu Leu Ser Gly Ser Arg Leu Ala Ala Gln Gln Gln Met Glu Gly Leu
            100                 105                 110 tta gcg ccg cat cgt ccg aaa gaa ccg gcg tgg ttt tta gcg acg gta     384
Leu Ala Pro His Arg Pro Lys Glu Pro Ala Trp Phe Leu Ala Thr Val
        115                 120                 125 ggt gta tcg ccg gat cat caa ggt aaa ggt tta ggt tcg gcg gta gta     432
Gly Val Ser Pro Asp His Gln Gly Lys Gly Leu Gly Ser Ala Val Val
130                 135                 140 tta ccg ggt gta gaa gcg gcg gaa cgt gcg ggt gta ccg gcg ttt tta     480
Leu Pro Gly Val Glu Ala Ala Glu Arg Ala Gly Val Pro Ala Phe Leu
145                 150                 155                 160 gaa acg tcg gcg ccg cgt aat tta ccg ttt tat gaa cgt tta ggt ttt     528
Glu Thr Ser Ala Pro Arg Asn Leu Pro Phe Tyr Glu Arg Leu Gly Phe
                165                 170                 175 acg gta acg gcg gat gta gaa gta ccg gaa ggt ccg cgt acg tgg tgt     576
Thr Val Thr Ala Asp Val Glu Val Pro Glu Gly Pro Arg Thr Trp Cys
            180                 185                 190 atg acg cgt aaa ccg ggt gcg tga                                     600
Met Thr Arg Lys Pro Gly Ala
        195

<210> SEQ ID NO 45
<211> LENGTH: 375
<212> TYPE: DNA
<213> ORGANISM: Artificial Sequence
<220> FEATURE:
<223> OTHER INFORMATION: Synthetic modified zeocin resistant gene
<220> FEATURE:
<221> NAME/KEY: CDS
<222> LOCATION: (1)..(375)

<400> SEQUENCE: 45 atg gcg aag tta acc tcg gcg gtt ccg gta tta acc gcg cgc gac gtc      48
Met Ala Lys Leu Thr Ser Ala Val Pro Val Leu Thr Ala Arg Asp Val
 1               5                  10                  15 gcg gga gcg gtc gag ttc tgg acc gac cgg tta ggg ttc tcg cgg gac     96
Ala Gly Ala Val Glu Phe Trp Thr Asp Arg Leu Gly Phe Ser Arg Asp
            20                  25                  30 ttc gta gag gac gac ttc gcg ggt gta gtc cgg gac gac gta acc tta    144
Phe Val Glu Asp Asp Phe Ala Gly Val Val Arg Asp Asp Val Thr Leu
        35                  40                  45 ttc atc tcg gcg gtc cag gac cag gta gta ccg gac aac acc tta gcg    192
Phe Ile Ser Ala Val Gln Asp Gln Val Val Pro Asp Asn Thr Leu Ala
 50                  55                  60 tgg gta tgg gta cgc ggc tta gac gag tta tac gcg gag tgg tcg gag    240
Trp Val Trp Val Arg Gly Leu Asp Glu Leu Tyr Ala Glu Trp Ser Glu
```

```
                65                  70                  75                  80
gtc gta tcg acg aac ttc cgg gac gcc tcg ggg ccg gcg atg acc gag        288
Val Val Ser Thr Asn Phe Arg Asp Ala Ser Gly Pro Ala Met Thr Glu
                    85                  90                  95 atc ggc gag cag ccg tgg ggg cgg gag ttc gcg tta cgc gac ccg gcg        336
Ile Gly Glu Gln Pro Trp Gly Arg Glu Phe Ala Leu Arg Asp Pro Ala
            100                 105                 110 ggc aac tgc gta cac ttc gta gcg gag gag cag gac tga                    375
Gly Asn Cys Val His Phe Val Ala Glu Glu Gln Asp
        115                 120

<210> SEQ ID NO 46
<211> LENGTH: 375
<212> TYPE: DNA
<213> ORGANISM: Artificial Sequence
<220> FEATURE:
<223> OTHER INFORMATION: Synthetic modified zeocin resistant gene
<220> FEATURE:
<221> NAME/KEY: CDS
<222> LOCATION: (1)..(375)

<400> SEQUENCE: 46 atg gcg aaa tta acg tcg gcg gta ccg gta tta acg gcg cgt gat gta        48
Met Ala Lys Leu Thr Ser Ala Val Pro Val Leu Thr Ala Arg Asp Val
1               5                   10                  15 gcg ggt gcg gta gaa ttt tgg acg gat cgt tta ggt ttt tcg cgt gat        96
Ala Gly Ala Val Glu Phe Trp Thr Asp Arg Leu Gly Phe Ser Arg Asp
                20                  25                  30 ttt gta gaa gat gat ttt gcg ggt gta gta cgt gat gat gta acg tta        144
Phe Val Glu Asp Asp Phe Ala Gly Val Val Arg Asp Asp Val Thr Leu
            35                  40                  45 ttt ata tcg gcg gta caa gat caa gta gta ccg gat aat acg tta gcg        192
Phe Ile Ser Ala Val Gln Asp Gln Val Val Pro Asp Asn Thr Leu Ala
        50                  55                  60 tgg gta tgg gta cgt ggt tta gat gaa tta tat gcg gaa tgg tcg gaa        240
Trp Val Trp Val Arg Gly Leu Asp Glu Leu Tyr Ala Glu Trp Ser Glu
65                  70                  75                  80 gta gta tcg acg aat ttt cgt gat gcg tcg ggt ccg gcg atg acg gaa        288
Val Val Ser Thr Asn Phe Arg Asp Ala Ser Gly Pro Ala Met Thr Glu
                    85                  90                  95 ata ggt gaa caa ccg tgg ggt cgt gaa ttt gcg tta cgt gat ccg gcg        336
Ile Gly Glu Gln Pro Trp Gly Arg Glu Phe Ala Leu Arg Asp Pro Ala
            100                 105                 110 ggt aat tgt gta cat ttt gta gcg gaa gaa caa gat tga                    375
Gly Asn Cys Val His Phe Val Ala Glu Glu Gln Asp
        115                 120

<210> SEQ ID NO 47
<211> LENGTH: 1026
<212> TYPE: DNA
<213> ORGANISM: Artificial Sequence
<220> FEATURE:
<223> OTHER INFORMATION: Synthetic modified hygromycin resistant gene
<220> FEATURE:
<221> NAME/KEY: CDS
<222> LOCATION: (1)..(1026)

<400> SEQUENCE: 47 atg aaa aag cct gaa tta acc gcg acg tcg gta gag aag ttt tta atc        48
Met Lys Lys Pro Glu Leu Thr Ala Thr Ser Val Glu Lys Phe Leu Ile
1               5                   10                  15 gaa aag ttc gac tcg gta tcg gac tta atg cag tta tcg gag ggc gaa        96
Glu Lys Phe Asp Ser Val Ser Asp Leu Met Gln Leu Ser Glu Gly Glu
                20                  25                  30
```

```
gaa tcg cgt gcg ttc tcg ttc gat gta gga ggg cgt gga tat gta tta      144
Glu Ser Arg Ala Phe Ser Phe Asp Val Gly Gly Arg Gly Tyr Val Leu
        35              40                  45 cgt gta aat tcg tgc gcg gat ggt ttc tac aaa gat cgt tat gta tat      192
Arg Val Asn Ser Cys Ala Asp Gly Phe Tyr Lys Asp Arg Tyr Val Tyr
50                  55                  60 cgt cac ttt gcg tcg gcg gcg tta ccg att ccg gaa gta tta gac att      240
Arg His Phe Ala Ser Ala Ala Leu Pro Ile Pro Glu Val Leu Asp Ile
65              70                  75                  80 ggg gaa ttc tcg gag tcg tta acc tat tgc atc tcg cgc cgt gcg cag      288
Gly Glu Phe Ser Glu Ser Leu Thr Tyr Cys Ile Ser Arg Arg Ala Gln
                    85                  90                  95 ggt gta acg ttg caa gac tta cct gaa acc gaa tta ccc gcg gta tta      336
Gly Val Thr Leu Gln Asp Leu Pro Glu Thr Glu Leu Pro Ala Val Leu
        100                 105                 110 cag ccg gta gcg gag gcg atg gat gcg atc gcg gcg gcg gat tta tcg      384
Gln Pro Val Ala Glu Ala Met Asp Ala Ile Ala Ala Ala Asp Leu Ser
            115                 120                 125 cag acg tcg ggg ttc ggc cca ttc gga ccg caa gga atc ggt caa tac      432
Gln Thr Ser Gly Phe Gly Pro Phe Gly Pro Gln Gly Ile Gly Gln Tyr
130                 135                 140 act aca tgg cgt gat ttc ata tgc gcg att gcg gat ccc cat gta tat      480
Thr Thr Trp Arg Asp Phe Ile Cys Ala Ile Ala Asp Pro His Val Tyr
145                 150                 155                 160 cac tgg caa act gta atg gac gac acc gta tcg gcg tcg gta gcg cag      528
His Trp Gln Thr Val Met Asp Asp Thr Val Ser Ala Ser Val Ala Gln
                    165                 170                 175 gcg tta gat gag tta atg tta tgg gcg gag gac tgc ccc gaa gta cgt      576
Ala Leu Asp Glu Leu Met Leu Trp Ala Glu Asp Cys Pro Glu Val Arg
                180                 185                 190 cac tta gta cac gcg gat ttc ggc tcg aac aat gta tta acg gac aat      624
His Leu Val His Ala Asp Phe Gly Ser Asn Asn Val Leu Thr Asp Asn
            195                 200                 205 ggc cgc ata aca gcg gta att gac tgg tcg gag gcg atg ttc ggg gat      672
Gly Arg Ile Thr Ala Val Ile Asp Trp Ser Glu Ala Met Phe Gly Asp
210                 215                 220 tcg caa tac gag gta gcg aac atc ttc ttc tgg cgt ccg tgg ttg gcg      720
Ser Gln Tyr Glu Val Ala Asn Ile Phe Phe Trp Arg Pro Trp Leu Ala
225                 230                 235                 240 tgt atg gag cag cag acg cgc tac ttc gag cgt cgt cat ccg gag tta      768
Cys Met Glu Gln Gln Thr Arg Tyr Phe Glu Arg Arg His Pro Glu Leu
                    245                 250                 255 gcg gga tcg ccg cgt tta cgt gcg tat atg tta cgc att ggt ctt gac      816
Ala Gly Ser Pro Arg Leu Arg Ala Tyr Met Leu Arg Ile Gly Leu Asp
                260                 265                 270 caa tta tat cag tcg ttg gta gac ggc aat ttc gat gat gcg gcg tgg      864
Gln Leu Tyr Gln Ser Leu Val Asp Gly Asn Phe Asp Asp Ala Ala Trp
            275                 280                 285 gcg cag ggt cga tgc gac gcg atc gta cga tcg gga gcg ggg act gta      912
Ala Gln Gly Arg Cys Asp Ala Ile Val Arg Ser Gly Ala Gly Thr Val
290                 295                 300 ggg cgt aca caa atc gcg cgc cgt tcg gcg gcg gta tgg acc gat ggc      960
Gly Arg Thr Gln Ile Ala Arg Arg Ser Ala Ala Val Trp Thr Asp Gly
305                 310                 315                 320 tgt gta gaa gta tta gcg gat tcg gga aac cga cgc ccc tcg act cgt     1008
Cys Val Glu Val Leu Ala Asp Ser Gly Asn Arg Arg Pro Ser Thr Arg
                    325                 330                 335 ccg cgt gcg aag gaa tag                                             1026
Pro Arg Ala Lys Glu
```

<210> SEQ ID NO 48
<211> LENGTH: 1026
<212> TYPE: DNA
<213> ORGANISM: Artificial Sequence
<220> FEATURE:
<223> OTHER INFORMATION: Synthetic modified hygromycin resistant gene
<220> FEATURE:
<221> NAME/KEY: CDS
<222> LOCATION: (1)..(1026)

<400> SEQUENCE: 48

```
atg aaa aaa ccg gaa tta acg gcg acg tcg gta gaa aaa ttt tta ata      48
Met Lys Lys Pro Glu Leu Thr Ala Thr Ser Val Glu Lys Phe Leu Ile
1               5                   10                  15 gaa aaa ttt gat tcg gta tcg gat tta atg caa tta tcg gaa ggt gaa      96
Glu Lys Phe Asp Ser Val Ser Asp Leu Met Gln Leu Ser Glu Gly Glu
                20                  25                  30 gaa tcg cgt gcg ttt tcg ttt gat gta ggt ggt cgt ggt tat gta tta     144
Glu Ser Arg Ala Phe Ser Phe Asp Val Gly Gly Arg Gly Tyr Val Leu
            35                  40                  45 cgt gta aat tcg tgt gcg gat ggt ttt tat aaa gat cgt tat gta tat     192
Arg Val Asn Ser Cys Ala Asp Gly Phe Tyr Lys Asp Arg Tyr Val Tyr
        50                  55                  60 cgt cat ttt gcg tcg gcg gcg tta ccg ata ccg gaa gta tta gat ata     240
Arg His Phe Ala Ser Ala Ala Leu Pro Ile Pro Glu Val Leu Asp Ile
65                  70                  75                  80 ggt gaa ttt tcg gaa tcg tta acg tat tgt ata tcg cgt cgt gcg caa     288
Gly Glu Phe Ser Glu Ser Leu Thr Tyr Cys Ile Ser Arg Arg Ala Gln
                85                  90                  95 ggt gta acg tta caa gat tta ccg gaa acg gaa tta ccg gcg gta tta     336
Gly Val Thr Leu Gln Asp Leu Pro Glu Thr Glu Leu Pro Ala Val Leu
            100                 105                 110 caa ccg gta gcg gaa gcg atg gat gcg ata gcg gcg gcg gat tta tcg     384
Gln Pro Val Ala Glu Ala Met Asp Ala Ile Ala Ala Ala Asp Leu Ser
        115                 120                 125 caa acg tcg ggt ttt ggt ccg ttt ggt ccg caa ggt ata ggt caa tat     432
Gln Thr Ser Gly Phe Gly Pro Phe Gly Pro Gln Gly Ile Gly Gln Tyr
    130                 135                 140 acg acg tgg cgt gat ttt ata tgt gcg ata gcg gat ccg cat gta tat     480
Thr Thr Trp Arg Asp Phe Ile Cys Ala Ile Ala Asp Pro His Val Tyr
145                 150                 155                 160 cat tgg caa acg gta atg gat gat acg gta tcg gcg tcg gta gcg caa     528
His Trp Gln Thr Val Met Asp Asp Thr Val Ser Ala Ser Val Ala Gln
                165                 170                 175 gcg tta gat gaa tta atg tta tgg gcg gaa gat tgt ccg gaa gta cgt     576
Ala Leu Asp Glu Leu Met Leu Trp Ala Glu Asp Cys Pro Glu Val Arg
            180                 185                 190 cat tta gta cat gcg gat ttt ggt tcg aat aat gta tta acg gat aat     624
His Leu Val His Ala Asp Phe Gly Ser Asn Asn Val Leu Thr Asp Asn
        195                 200                 205 ggt cgt ata acg gcg gta ata gat tgg tcg gaa gcg atg ttt ggt gat     672
Gly Arg Ile Thr Ala Val Ile Asp Trp Ser Glu Ala Met Phe Gly Asp
    210                 215                 220 tcg caa tat gaa gta gcg aat ata ttt ttt tgg cgt ccg tgg tta gcg     720
Ser Gln Tyr Glu Val Ala Asn Ile Phe Phe Trp Arg Pro Trp Leu Ala
225                 230                 235                 240 tgt atg gaa caa caa acg cgt tat ttt gaa cgt cgt cat ccg gaa tta     768
Cys Met Glu Gln Gln Thr Arg Tyr Phe Glu Arg Arg His Pro Glu Leu
                245                 250                 255
```

```
gcg ggt tcg ccg cgt tta cgt gcg tat atg tta cgt ata ggt tta gat      816
Ala Gly Ser Pro Arg Leu Arg Ala Tyr Met Leu Arg Ile Gly Leu Asp
            260                 265                 270 caa tta tat caa tcg tta gta gat ggt aat ttt gat gat gcg gcg tgg      864
Gln Leu Tyr Gln Ser Leu Val Asp Gly Asn Phe Asp Asp Ala Ala Trp
        275                 280                 285 gcg caa ggt cgt tgt gat gcg ata gta cgt tcg ggt gcg ggt acg gta      912
Ala Gln Gly Arg Cys Asp Ala Ile Val Arg Ser Gly Ala Gly Thr Val
    290                 295                 300 ggt cgt acg caa ata gcg cgt cgt tcg gcg gcg gta tgg acg gat ggt      960
Gly Arg Thr Gln Ile Ala Arg Arg Ser Ala Ala Val Trp Thr Asp Gly
305                 310                 315                 320 tgt gta gaa gta tta gcg gat tcg ggt aat cgt cgt ccg tcg acg cgt     1008
Cys Val Glu Val Leu Ala Asp Ser Gly Asn Arg Arg Pro Ser Thr Arg
                325                 330                 335 ccg cgt gcg aaa gaa tga                                              1026
Pro Arg Ala Lys Glu
            340
```

<210> SEQ ID NO 49
<211> LENGTH: 264
<212> TYPE: PRT
<213> ORGANISM: Artificial Sequence
<220> FEATURE:
<223> OTHER INFORMATION: Synthetic Construct

<400> SEQUENCE: 49

```
Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240
```

Leu Val Leu Tyr Gly Ile Ala Ala Pro Asp Ser Gln Arg Ile Ala Phe
            245                 250                 255

Tyr Arg Leu Leu Asp Glu Phe Phe
            260

<210> SEQ ID NO 50
<211> LENGTH: 264
<212> TYPE: PRT
<213> ORGANISM: Artificial Sequence
<220> FEATURE:
<223> OTHER INFORMATION: Synthetic Construct

<400> SEQUENCE: 50

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260

<210> SEQ ID NO 51
<211> LENGTH: 264
<212> TYPE: PRT
<213> ORGANISM: Artificial Sequence
<220> FEATURE:
<223> OTHER INFORMATION: Synthetic Construct

<400> SEQUENCE: 51

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
            35                  40                  45

Val Lys Thr Asp Leu Ser Gly Ala Leu Asn Glu Leu Gln Asp Glu Ala
 50                  55                  60

Ala Arg Leu Ser Trp Leu Ala Thr Thr Gly Val Pro Cys Ala Ala Val
 65                  70                  75                  80

Leu Asp Val Val Thr Glu Ala Gly Arg Asp Trp Leu Leu Gly Glu
                85                  90                  95

Val Pro Gly Gln Asp Leu Leu Ser Ser His Leu Ala Pro Ala Glu Lys
                100                 105                 110

Val Ser Ile Met Ala Asp Ala Met Arg Arg Leu His Thr Leu Asp Pro
            115                 120                 125

Ala Thr Cys Pro Phe Asp His Gln Ala Lys His Arg Ile Glu Arg Ala
130                 135                 140

Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
            195                 200                 205

Cys Gly Arg Leu Gly Val Ala Asp Arg Tyr Gln Asp Ile Ala Leu Ala
210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
                260

<210> SEQ ID NO 52
<211> LENGTH: 264
<212> TYPE: PRT
<213> ORGANISM: Artificial Sequence
<220> FEATURE:
<223> OTHER INFORMATION: Synthetic Construct

<400> SEQUENCE: 52

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
            35                  40                  45

Val Lys Thr Asp Leu Ser Gly Ala Leu Asn Glu Leu Gln Asp Glu Ala
 50                  55                  60

Ala Arg Leu Ser Trp Leu Ala Thr Thr Gly Val Pro Cys Ala Ala Val
 65                  70                  75                  80

Leu Asp Val Val Thr Glu Ala Gly Arg Asp Trp Leu Leu Gly Glu
                85                  90                  95

Val Pro Gly Gln Asp Leu Leu Ser Ser His Leu Ala Pro Ala Glu Lys
                100                 105                 110

```
Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260

<210> SEQ ID NO 53
<211> LENGTH: 199
<212> TYPE: PRT
<213> ORGANISM: Artificial Sequence
<220> FEATURE:
<223> OTHER INFORMATION: Synthetic Construct

<400> SEQUENCE: 53

Met Thr Glu Tyr Lys Pro Thr Val Arg Leu Ala Thr Arg Asp Asp Val
1               5                   10                  15

Pro Arg Ala Val Arg Thr Leu Ala Ala Ala Phe Ala Asp Tyr Pro Ala
            20                  25                  30

Thr Arg His Thr Val Asp Pro Asp Arg His Ile Glu Arg Val Thr Glu
        35                  40                  45

Leu Gln Glu Leu Phe Leu Thr Arg Val Gly Leu Asp Ile Gly Lys Val
    50                  55                  60

Trp Val Ala Asp Asp Gly Ala Val Ala Val Trp Thr Thr Pro Glu
65                  70                  75                  80

Ser Val Glu Ala Gly Ala Val Phe Ala Glu Ile Gly Pro Arg Met Ala
                85                  90                  95

Glu Leu Ser Gly Ser Arg Leu Ala Ala Gln Gln Gln Met Glu Gly Leu
            100                 105                 110

Leu Ala Pro His Arg Pro Lys Glu Pro Ala Trp Phe Leu Ala Thr Val
        115                 120                 125

Gly Val Ser Pro Asp His Gln Gly Lys Gly Leu Gly Ser Ala Val Val
    130                 135                 140

Leu Pro Gly Val Glu Ala Ala Glu Arg Ala Gly Val Pro Ala Phe Leu
145                 150                 155                 160

Glu Thr Ser Ala Pro Arg Asn Leu Pro Phe Tyr Glu Arg Leu Gly Phe
                165                 170                 175

Thr Val Thr Ala Asp Val Glu Val Pro Glu Gly Pro Arg Thr Trp Cys
            180                 185                 190

Met Thr Arg Lys Pro Gly Ala
        195
```

```
<210> SEQ ID NO 54
<211> LENGTH: 199
<212> TYPE: PRT
<213> ORGANISM: Artificial Sequence
<220> FEATURE:
<223> OTHER INFORMATION: Synthetic Construct

<400> SEQUENCE: 54
```

Met Thr Glu Tyr Lys Pro Thr Val Arg Leu Ala Thr Arg Asp Asp Val
1               5                   10                  15

Pro Arg Ala Val Arg Thr Leu Ala Ala Ala Phe Ala Asp Tyr Pro Ala
            20                  25                  30

Thr Arg His Thr Val Asp Pro Asp Arg His Ile Glu Arg Val Thr Glu
        35                  40                  45

Leu Gln Glu Leu Phe Leu Thr Arg Val Gly Leu Asp Ile Gly Lys Val
    50                  55                  60

Trp Val Ala Asp Asp Gly Ala Ala Val Ala Val Trp Thr Thr Pro Glu
65                  70                  75                  80

Ser Val Glu Ala Gly Ala Val Phe Ala Glu Ile Gly Pro Arg Met Ala
                85                  90                  95

Glu Leu Ser Gly Ser Arg Leu Ala Ala Gln Gln Gln Met Glu Gly Leu
            100                 105                 110

Leu Ala Pro His Arg Pro Lys Glu Pro Ala Trp Phe Leu Ala Thr Val
        115                 120                 125

Gly Val Ser Pro Asp His Gln Gly Lys Gly Leu Gly Ser Ala Val Val
    130                 135                 140

Leu Pro Gly Val Glu Ala Ala Glu Arg Ala Gly Val Pro Ala Phe Leu
145                 150                 155                 160

Glu Thr Ser Ala Pro Arg Asn Leu Pro Phe Tyr Glu Arg Leu Gly Phe
                165                 170                 175

Thr Val Thr Ala Asp Val Glu Val Pro Glu Gly Pro Arg Thr Trp Cys
            180                 185                 190

Met Thr Arg Lys Pro Gly Ala
        195

```
<210> SEQ ID NO 55
<211> LENGTH: 199
<212> TYPE: PRT
<213> ORGANISM: Artificial Sequence
<220> FEATURE:
<223> OTHER INFORMATION: Synthetic Construct

<400> SEQUENCE: 55
```

Met Thr Glu Tyr Lys Pro Thr Val Arg Leu Ala Thr Arg Asp Asp Val
1               5                   10                  15

Pro Arg Ala Val Arg Thr Leu Ala Ala Ala Phe Ala Asp Tyr Pro Ala
            20                  25                  30

Thr Arg His Thr Val Asp Pro Asp Arg His Ile Glu Arg Val Thr Glu
        35                  40                  45

Leu Gln Glu Leu Phe Leu Thr Arg Val Gly Leu Asp Ile Gly Lys Val
    50                  55                  60

Trp Val Ala Asp Asp Gly Ala Ala Val Ala Val Trp Thr Thr Pro Glu
65                  70                  75                  80

Ser Val Glu Ala Gly Ala Val Phe Ala Glu Ile Gly Pro Arg Met Ala
                85                  90                  95

Glu Leu Ser Gly Ser Arg Leu Ala Ala Gln Gln Gln Met Glu Gly Leu

```
                100              105                 110
Leu Ala Pro His Arg Pro Lys Glu Pro Ala Trp Phe Leu Ala Thr Val
            115                 120                 125

Gly Val Ser Pro Asp His Gln Gly Lys Gly Leu Gly Ser Ala Val Val
        130                 135             140

Leu Pro Gly Val Glu Ala Ala Glu Arg Ala Gly Val Pro Ala Phe Leu
145                 150                 155                 160

Glu Thr Ser Ala Pro Arg Asn Leu Pro Phe Tyr Glu Arg Leu Gly Phe
                165                 170                 175

Thr Val Thr Ala Asp Val Glu Val Pro Glu Gly Pro Arg Thr Trp Cys
            180                 185                 190

Met Thr Arg Lys Pro Gly Ala
            195

<210> SEQ ID NO 56
<211> LENGTH: 199
<212> TYPE: PRT
<213> ORGANISM: Artificial Sequence
<220> FEATURE:
<223> OTHER INFORMATION: Synthetic Construct

<400> SEQUENCE: 56

Met Thr Glu Tyr Lys Pro Thr Val Arg Leu Ala Thr Arg Asp Asp Val
1               5                   10                  15

Pro Arg Ala Val Arg Thr Leu Ala Ala Ala Phe Ala Asp Tyr Pro Ala
            20                  25                  30

Thr Arg His Thr Val Asp Pro Asp Arg His Ile Glu Arg Val Thr Glu
        35                  40                  45

Leu Gln Glu Leu Phe Leu Thr Arg Val Gly Leu Asp Ile Gly Lys Val
    50                  55                  60

Trp Val Ala Asp Asp Gly Ala Ala Val Ala Val Trp Thr Thr Pro Glu
65                  70                  75                  80

Ser Val Glu Ala Gly Ala Val Phe Ala Glu Ile Gly Pro Arg Met Ala
                85                  90                  95

Glu Leu Ser Gly Ser Arg Leu Ala Ala Gln Gln Gln Met Glu Gly Leu
            100                 105                 110

Leu Ala Pro His Arg Pro Lys Glu Pro Ala Trp Phe Leu Ala Thr Val
        115                 120                 125

Gly Val Ser Pro Asp His Gln Gly Lys Gly Leu Gly Ser Ala Val Val
    130                 135                 140

Leu Pro Gly Val Glu Ala Ala Glu Arg Ala Gly Val Pro Ala Phe Leu
145                 150                 155                 160

Glu Thr Ser Ala Pro Arg Asn Leu Pro Phe Tyr Glu Arg Leu Gly Phe
                165                 170                 175

Thr Val Thr Ala Asp Val Glu Val Pro Glu Gly Pro Arg Thr Trp Cys
            180                 185                 190

Met Thr Arg Lys Pro Gly Ala
            195

<210> SEQ ID NO 57
<211> LENGTH: 124
<212> TYPE: PRT
<213> ORGANISM: Artificial Sequence
<220> FEATURE:
<223> OTHER INFORMATION: Synthetic Construct

<400> SEQUENCE: 57
```

-continued

```
Met Ala Lys Leu Thr Ser Ala Val Pro Val Leu Thr Ala Arg Asp Val
1               5                   10                  15

Ala Gly Ala Val Glu Phe Trp Thr Asp Arg Leu Gly Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
            115                 120
```

<210> SEQ ID NO 58
<211> LENGTH: 124
<212> TYPE: PRT
<213> ORGANISM: Artificial Sequence
<220> FEATURE:
<223> OTHER INFORMATION: Synthetic Construct

<400> SEQUENCE: 58

```
Met Ala Lys Leu Thr Ser Ala Val Pro Val Leu Thr Ala Arg Asp Val
1               5                   10                  15

Ala Gly Ala Val Glu Phe Trp Thr Asp Arg Leu Gly Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
            115                 120
```

<210> SEQ ID NO 59
<211> LENGTH: 341
<212> TYPE: PRT
<213> ORGANISM: Artificial Sequence
<220> FEATURE:
<223> OTHER INFORMATION: Synthetic Construct

<400> SEQUENCE: 59

```
Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60
```

```
Arg His Phe Ala Ser Ala Ala Leu Pro Ile Pro Glu Val Leu Asp Ile
 65                  70                  75                  80

Gly Glu Phe Ser Glu Ser Leu Thr Tyr Cys Ile Ser Arg Arg Ala Gln
             85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Asp Leu Ser
        115                 120                 125

Gln Thr Ser Gly Phe Gly Pro Phe Gly Pro Gln Gly Ile Gly Gln Tyr
130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Arg Ala Lys Glu
            340

<210> SEQ ID NO 60
<211> LENGTH: 341
<212> TYPE: PRT
<213> ORGANISM: Artificial Sequence
<220> FEATURE:
<223> OTHER INFORMATION: Synthetic Construct

<400> SEQUENCE: 60

Met Lys Lys Pro Glu Leu Thr Ala Thr Ser Val Glu Lys Phe Leu Ile
  1               5                  10                  15

Glu Lys Phe Asp Ser Val Ser Asp Leu Met Gln Leu Ser Glu Gly Glu
                 20                  25                  30

Glu Ser Arg Ala Phe Ser Phe Asp Val Gly Gly Arg Gly Tyr Val Leu
             35                  40                  45

Arg Val Asn Ser Cys Ala Asp Gly Phe Tyr Lys Asp Arg Tyr Val Tyr
         50                  55                  60

Arg His Phe Ala Ser Ala Ala Leu Pro Ile Pro Glu Val Leu Asp Ile
 65                  70                  75                  80
```

-continued

```
Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
                180                 185                 190

His Leu Val His Ala Asp Phe Gly Ser Asn Asn Val Leu Thr Asp Asn
            195                 200                 205

Gly Arg Ile Thr Ala Val Ile Asp Trp Ser Glu Ala Met Phe Gly Asp
        210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
                260                 265                 270

Gln Leu Tyr Gln Ser Leu Val Asp Gly Asn Phe Asp Asp Ala Ala Trp
            275                 280                 285

Ala Gln Gly Arg Cys Asp Ala Ile Val Arg Ser Gly Ala Gly Thr Val
        290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Arg Ala Lys Glu
            340
```

PROCESS FOR PRODUCTION OF PROTEIN

BACKGROUND OF THE INVENTION

1. Field of the Invention

This invention relates to a method for integrating a gene fragment inserted between a pair of transposon sequences into a chromosome of a mammalian cell, comprising introducing at least one expression vector which comprises a gene fragment comprising a DNA encoding a protein of interest and also comprises a pair of transposon sequences at both terminals of the gene fragment, into a suspension mammalian cell; and a method for producing the protein comprising suspension-culturing a suspension mammalian cell which produces the protein, a suspension mammalian cell which expresses the protein; and an expression vector which comprises a gene fragment comprising a DNA encoding a protein of interest and also comprises a pair of transposon sequences at both terminals of the gene fragment.

2. Brief Description of the Background Art

Production of exogenous proteins by recombinant DNA techniques is used in various industries such as pharmaceutical industry and food industry. In most cases, production of recombinant proteins is carried out by introducing an expression vector comprising a nucleotide sequence encoding a protein of interest into a host, such as *Escherichia coli*, yeast, insect cell, plant cell, and animal cell, selecting a transformant in which the expression vector is integrated into the chromosome, and further culturing the transformed cell line under appropriate culture conditions.

However, in order to develop a host which can produce an exogenous protein efficiently, it is necessary to select a host cell having good productivity for each protein of interest, so that a further technical innovation is desired on the exogenous protein production techniques for each host.

In the bacteria systems, such as *Escherichia coli*, and yeast systems, different from animal cells, post-translational modifications, such as sugar chain modification, are difficult to attain in many cases and thus cause a problem in producing a protein having its activity.

Since the produced protein is subject to a post-translational modification such as phosphorylation and addition of sugar chains in the insect system, this system has a merit that the protein having its original physiological activity can be expressed. However, since the sugar chain structure of the secreted protein is different from that of mammalians-derived cells, antigenicity and the like become a problem when the protein is applied to pharmaceutical use.

In addition, since a recombinant virus is used in the insect cell system when an exogenous gene is introduced, there is a problem that its inactivation and containment of the virus are required from the viewpoint of safety.

In the animal cell system, post-translational modifications, such as phosphorylation, sugar chain addition, and folding, can be conducted to proteins derived from higher animals including human, in more similar manner to those produced in the living body. Such accurate post-translational modifications are necessary for recreating the physiological activity originally possessed by a protein in its recombinant protein, and a protein production system in which a mammalian cell is used as a host is usually applied to pharmaceutical products and the like that requires such physiological activity.

However, a protein expression system in which a mammalian cell is used as the host is generally low in productivity, and also causes a problem of the stability of introduced genes in many cases. Improvement of productivity of a protein using a mammalian culture cell as a host is not only very important in producing medicaments for treatment, diagnostic agents and the like, but also greatly contributes to research and development of them. Thus, it is urgent to develop a gene expression system which easily makes it possible to obtain a cell line of a high productivity using a mammalian culture cell, particularly Chinese hamster ovary cell (CHO cell), as the host.

A transposon is a transposable genetic element which can move from one locus to other locus on the chromosome. A transposon is a strong tool for the study on molecular biology and genetics and used for a purpose, such as mutagenesis, gene trapping, and preparation of transgenic individuals, in insects or nematode (e.g., *Drosophila melanogaster* or *Caenorhabditis elegans*) and plants. However, development of such a technique has been delayed for vertebral animals including mammalian cells.

In recent years, however, transposons which have activities also in vertebral animals have been reported, and some of them were shown to have an activity in mammalian cells, such as cell derived from mouse and human. Typical examples include transposons Tol1 (Patent Reference 1) and Tol2 (Non-patent Reference 1) which are cloned from a medaka (killifish), Sleeping Beauty reconstructed from a non-autonomous transposon existed in *Onchorhynchus* fish genome (Non-patent Reference 2), an artificial transposon Frog prince (Non-patent Reference 3) which is derived from frog and a transposon piggyBac (Non-patent Reference 4) which is derived from insect.

These DNA transposons have been used for mutagenesis, gene trapping, preparation of transgenic individuals, expression of drug-resistant proteins, and the like, as a gene introduction tool for bringing a new phenotype in a genome of a mammalian cell (Non-patent References 5 to 12).

In the case of insects, a method in which an exogenous gene is introduced into silkworm chromosome using the transposon piggyBac derived from a Lepidoptera insect to express the protein encoded by said exogenous gene has been studied, and a protein production method using the above techniques was disclosed (Patent Reference 2).

However, since protein of interest is not expressed at sufficient levels and is produced in the whole body of silkworm, it causes an economical problem due to the necessity of an advanced purification technique for recovering the expressed exogenous protein in a highly purified form from the body fluid including a large amount of contaminated proteins.

In addition, an example in which a protein relating to G418 resistance is expressed in a mammalian cell using the medaka-derived transposon Tol2 (Non-patent References 12 and 13) is known.

In the case of producing a protein drug for medical use using a mammal-derived cultured cell, it is important that an animal-derived component is not contained during its production process in order to prevent unexpected contamination of an unknown virus or pathogenic polypeptide. CHO cell is most frequently used as an animal cell for producing a protein drug, and due to the studies of recent years, a suspension CHO cell line capable of culturing in a safe medium which does not use a serum or animal-derived component has also be established. However, productivity of a cell line into which a gene was introduced under a serum-free or protein-free condition is limited to half that of the cell line into which a gene was introduced under a serum-used condition (Non Patent Literature 14). It is shown that gene transduction under a serum-free or protein-free condition is technically difficult.

It is general that a selectable marker for screening a cell expressing a protein of interest is arranged on the same gene expression vector. This is based on a hypothesis that there are a region where a gene existing in the genome is easily expressed and a region where a gene existing in the genome is hardly expressed (called as position effects, Non Patent Literature 15), and that the protein of interest is also expressed when the selectable marker is expressed.

On the other hand, when a protein of interest, is comprised of two or more polypeptides such as an antibody and the like, it is also known that each polypeptide is expressed using different vectors. In the case of an antibody, it has been shown that the productivity is higher when expression of heavy chain of the antibody is higher than the expression of light chain (Non Patent Literature 16). Since it is predicted that expressions of heavy chain and light chain become constant on the same vector. It becomes possible to obtain a cell line which expresses the heavy chain and light chain at an optimum ratio by intentionally expressing the heavy chain and light chain using different vectors for the purpose of obtaining high productivity. However, when a protein is expressed using two or more different vectors, two or more selectable marker genes are also necessary.

As a way for overcoming this, it was reported a case in which a dhfr gene originally consisting of one polypeptide chain was divided into two polypeptide chains and one of them was arranged on a heavy chain expression vector, and the other was arranged on a light chain expression vector (Non Patent Literature 17).

However, the cell described in the Non Patent Literature 17 is a CHO cell in which the cell is dependent on the protein component added to the medium, and as described in the above, there is a possibility that the gene introduction efficiency is high different from the case of the gene introduction under a serum-free or protein-free condition. It is predicted that selecting a cell of high productivity is still difficult when a gene is introduced under a serum-free or protein-free condition having high safety and free from the danger of viral infection and the like.

CITATION LIST

Patent Literature

[Patent Literature 1] WO2008/072540
[Patent Literature 2] Japanese Published Unexamined Patent Application No. 2001-532188

Non Patent Literature

[Non Patent Literature 1] *Nature* 383, 30 (1996)
[Non Patent Literature 2] *Cell* 91, 501-510 (1997)
[Non Patent Literature 3] *Nucleic Acids Res,* 31, 6873-6881 (2003)
[Non Patent Literature 4] *Insect Mol. Biol.* 5, 141-151 (1996)
[Non Patent Literature 5] *Genetics.* 166, 895-899 (2004)
[Non Patent Literature 6] *PLoS Genet,* 2, e169 (2006)
[Non Patent Literature 7] *Proc. Natl. Acad. Sci. USA* 95, 10769-10773 (1998)
[Non Patent Literature 8] *Proc. Natl. Acad. Sci. USA* 98:6759-6764 (2001)
[Non Patent Literature 9] *Nature* 436, 221-226 (2005)
[Non Patent Literature 10] *Nucleic Acids Res.,* 31, 6873-6881 (2003)
[Non Patent Literature 11] *Nucleic Acids Res.,* 35, e87 (2007)
[Non Patent Literature 12] *Proc Natl. Acad. Sci. USA,* 103, 15008-15013 (2006)
[Non Patent Literature 13] *Plos Genetics,* 2, 1715-1724 (2006)
[Non Patent Literature 14] *Biotech. Bioeng.* 96, 1118-1126 (2007)
[Non Patent Literature 15] *Nature Biotech.* 22, 1393-1398 (2004)
[Non Patent Literature 16] *Biotech. Bioeng.* 96, 337-348 (2007)
[Non Patent Literature 17] *Biotech. Bioeng.* 84, 439-444 (2003)

SUMMARY OF THE INVENTION

In order to produce and analyze a protein of interest, it is necessary to select a cell line which stably and highly expresses a protein of interest, using a mammalian-derived culture cell. However, preparing and culturing the cell that produces the protein of interest require considerable effort and time.

In addition, though it is known that a protein of interest is expressed in a mammalian cell using a transposon sequence, preparation of a cell which can highly express a protein of interest and thus can be used as a protein production system by using a transposon sequence; a preparation method of a mammalian cell which can highly produce a protein of interest by using a transposon sequence; and a production method of a protein using the cell are not known.

As described in the above, the expression of a protein of interest in a large amount by establishing a protein production system which can highly produce a protein of interest using a mammalian culture cell efficiently and within a short period has been required. In addition, establishment of a producing cell which does not require any components derived from an animal from the gene introduction to establishment of a producing cell has been desired.

Thus, the objects of the invention are to provide a cell capable of highly expressing a protein of interest which can be efficiently established, and a method for producing the protein of interest using the cell.

To solve the above-mentioned problems, the present inventors have conducted intensive studies and found as a result that a protein of interest can be efficiently produced by introducing at least one expression vector which comprises a gene fragment comprising a DNA encoding the protein of interest and also comprises a pair of transposon sequences at both terminals of the gene fragment, into a suspension mammalian cell; and integrating the gene fragment inserted between a pair (two) of the transposon sequences into a chromosome of the mammalian cell. In addition, it was found that the protein of interest can be produced efficiently by using the cell, and thereby the invention was accomplished.

According to the protein production method of the invention, a protein of interest can be efficiently produced by using a suspension mammalian cell. In addition, the cell of the present invention can be used as a production cell for producing a recombinant protein or a recombinant polypeptide with a high efficiency.

BRIEF DESCRIPTION OF THE DRAWINGS

FIG. 4A represents a result of a suspension CHO-K1 cell and FIG. 4B represents a result of an adhesive CHO-K1 cell. In the both figures, the ordinate shows the amount of antibody production (μg/ml), and the abscissa shows the number of transgenic clones of each cell.

In FIG. 13, Tol2-L represents a DNA fragment comprising the Tol2-L sequence (SEQ ID NO:2), and Tol2-R represents a DNA fragment comprising the Tol2-R sequence (SEQ ID NO:3), CMV represents a CMV promoter, poly A represents a polyadenylation site, Hc represents a heavy chain gene of CD98 antibody, Lc represents an anti-human CD98 antibody light chain gene, SO represents an SV40 promoter, SV represents an SV40 polyadenylation site, and Neo-r represents a neomycin resistance gene.

DETAILED DESCRIPTION OF THE INVENTION

Figure 1:
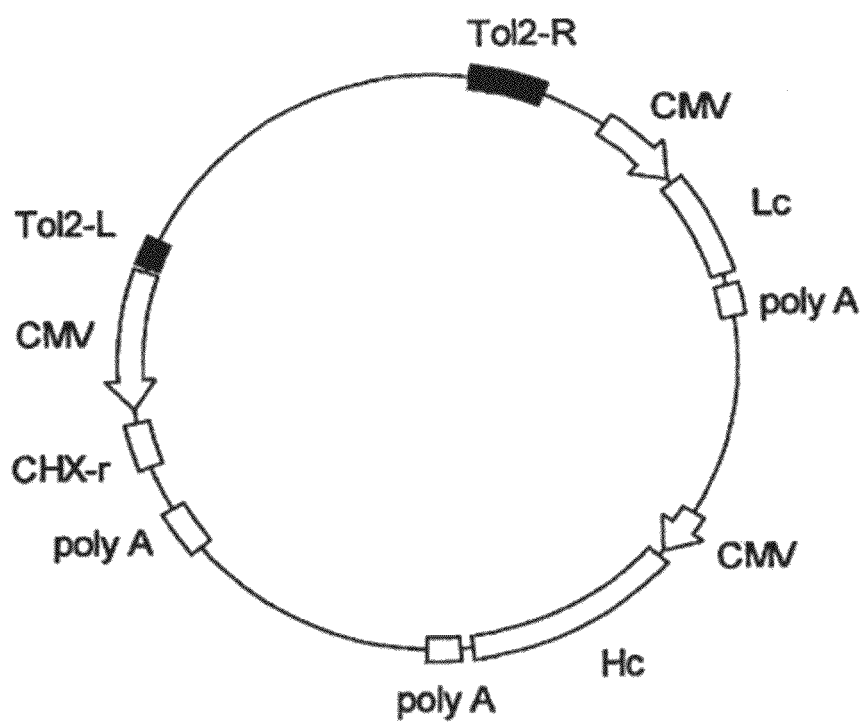
FIG. 1 shows a schematic illustration of a transposon vector for expressing an anti-human influenza M2 antibody. Tol2-L represents a left end Tol2 transposon (SEQ ID NO:2), Tol2-R represents a right end Tol2 transposon (SEQ ID NO:3), CMV represents a CMV promoter, poly A represents a polyadenylation site, Hc represents a human antibody H chain cDNA, Lc represents a human antibody L chain cDNA, and CHX-r represents a cycloheximide resistance gene.

Specifically, the invention relates to the followings:

1. A method for producing a protein of interest, comprising introducing at least one expression vector which comprises a gene fragment comprising a DNA encoding a protein of interest and also comprises a pair of transposon sequences at both terminals of the gene fragment, into a suspension mammalian cell; integrating the gene fragment comprising the DNA encoding the protein of interest inserted between a pair of the transposon sequences into a chromosome of the mammalian cell to obtain a mammalian cell which expresses the protein of interest; and suspension-culturing the mammalian cell;

2. A method for producing a protein of interest, comprising the following steps (A) to (C):

(A) a step of simultaneously introducing the following expression vectors (a) and (b) into a suspension mammalian cell:

(a) at least one expression vector which comprises a gene fragment comprising a DNA encoding a protein of interest and also comprises a pair of transposon sequences at both terminals of the gene fragment, (b) an expression vector which comprises a DNA encoding a transposase which recognizes the transposon sequences and has activity of transferring a gene fragment inserted between a pair of the transposon sequences into a chromosome, (B) a step of obtaining a suspension mammalian cell which expresses the protein of interest by expressing transiently the transposase from the expression vector which is introduced into the suspension mammalian cell in the step (A) to integrate the gene fragment inserted between a pair of the transposon sequences into a chromosome of the mammalian cell, and (C) a step of suspension-culturing the suspension mammalian cell which expresses the protein of interest obtained in the step (B) to produce the protein of interest;

3. A method for obtaining a suspension mammalian cell which expresses a protein of interest, comprising introducing at least one expression vector which comprises a gene fragment comprising a DNA encoding a protein of interest and also comprises transposon sequences at both terminals of the gene fragment into a suspension mammalian cell, and integrating the gene fragment inserted between a pair of the transposon sequences, into a chromosome of the mammalian cell;

4. The method described in any one of the above items 1 to 3, wherein at least one of the expression vectors which comprises a gene fragment comprising a DNA encoding the protein of interest and also comprises a pair of transposon sequences at both terminals of the gene fragment is an expression vector which comprises a gene fragment comprising a DNA encoding the protein of interest and a selectable marker gene and also comprises a pair of transposon sequences at both terminals of the gene fragment;

5. The method described in any one of the above items 1 to 4, comprising introducing an expression vector which comprises a gene fragment comprising a selectable marker and comprises a pair of transposon sequences at both terminals of the gene fragment into a mammalian cell in addition to the expression vector which comprises a gene fragment comprising a DNA encoding the protein of interest and also comprises a pair of transposon sequences at both terminals of the gene fragment;

6. The method described in any one of the above items 1 to 5, wherein the DNA encoding the protein of interest is a DNA encoding an antibody.

7. The method described in any one of the above item 6, wherein the DNA encoding an antibody is at least one of a DNA encoding a H chain of the antibody and a DNA encoding a L chain of the antibody;

8. The method described in any one of the above items 4 to 7, wherein an expression vector selected from the following (a) to (d) is introduced into a suspension mammalian cell:

(a) an expression vector which comprises a gene fragment comprising a DNA encoding a H chain of an antibody and also comprises a pair of transposon sequences at both terminals of the gene fragment, an expression vector which comprises a gene fragment comprising a DNA encoding a L chain of an antibody and also comprises a pair of transposon sequences at both terminals of the gene fragment and an expression vector which comprises a gene fragment comprising a selectable marker gene and also comprises a pair of transposon sequences at both terminals of the gene fragment (b) an expression vector which comprises a gene fragment comprising a DNA encoding a H chain of an antibody and a selectable marker gene and also comprises a pair of transposon sequences at both terminals of the gene fragment and an expression vector which comprises a gene fragment comprising a DNA encoding a L chain of an antibody and also comprises a pair of transposon sequences at both terminals of the gene fragment, (c) an expression vector which comprises a gene fragment comprising a DNA encoding a L chain of an antibody and a selectable marker gene and also comprises a pair of transposon sequences at both terminals of the gene fragment and an expression vector which comprises a gene fragment comprising a DNA encoding a H chain of an antibody and also comprises a pair of transposon sequences at both terminals of the gene fragment, and (d) an expression vector which comprises a gene fragment comprising a DNA encoding a H chain and a L chain of an antibody and a selectable marker gene and also comprises a pair of transposon sequences at both terminals of the gene fragment;

9. The method described in any one of the above items 1 to 8, wherein the suspension mammalian cell is a cell capable of surviving and proliferating in a serum-free medium;

10. The method described in any one of the above items 1 to 9, wherein the suspension mammalian cell is at least one selected from a suspension CHO cell in which a CHO cell is adapted to suspension culture, a PER.C6 cell, a rat myeloma cell YB2/3HL.P2.G11.16Ag.20 (or also called YB2/0) and a suspension mouse myeloma cell NS0 adapted to suspension culture;

11. The method described in the above item 10, wherein the CHO cell is at least one selected from CHO-K1, CHO-K1SV, DUKXB11, CHO/DG44, Pro-3 and CHO-S;

12. The method described in any one of the above items 4 to 11, wherein the selectable marker gene is a cycloheximide resistance gene;

13. The method described in any one of the above item 12, wherein the cycloheximide resistance gene is a ribosome protein;

14. The method described in any one of the above items 1 to 13, wherein a pair of the transposon sequences are nucleotide sequences derived from a pair of DNA-type transposons which function in a mammalian cell;

15. The method described in the above item 14, wherein the nucleotide sequences derived from a pair of DNA type transposons are nucleotide sequences derived from a pair of Tol1 transposons or nucleotide sequences derived from a pair of Tol2 transposons;

16. The method described in the above item 15, wherein the nucleotide sequences derived from a pair of Tol2 transposons are a nucleotide sequence comprising the nucleotide sequence shown in SEQ ID NO:2 and the nucleotide sequence shown in SEQ ID NO:3;

17. The method described in the above item 15, wherein the nucleotide sequences derived from a pair of Tol1 transposons are the nucleotide sequences shown in SEQ ID NO:14 and the nucleotide sequence shown in SEQ ID NO:15.

18. A suspension mammalian cell, which has a chromosome into which a gene fragment inserted between a pair of the transposons is integrated and which produces a protein of interest obtainable by simultaneously introducing at least one of expression vector (a) which comprises the gene fragment comprising a DNA encoding a protein of interest and also comprises the pair of transposon sequences at both terminals of the gene fragment and an expression vector (b) which comprises a DNA encoding a transposase (transferase) capable of recognizing the transposon sequences and having the activity to transfer the gene fragment inserted between the pair of transposon sequences to the chromosome.

19. The mammalian cell described in the above item 18, wherein the at least one of expression vector (a) which comprises a gene fragment comprising a DNA encoding a protein of interest and also comprises a pair of transposon sequences at both terminals of the gene fragment is an expression vector which comprises a gene fragment comprising a DNA encoding a protein of interest and a selectable marker gene and also comprises a pair of transposon sequences at both terminals of the gene fragment.

20. The mammalian cell described in the above item 18 or 19, which is a cell prepared by further introducing an expression vector (c) which comprises a gene fragment comprising a selectable marker gene and also comprises a pair of transposon sequences at both terminals of the gene fragment in addition to the expression vectors (a) and (b).

21. The mammalian cell described in any one of the above items 18 to 20, wherein the DNA encoding the protein of interest is a DNA which encodes an antibody.

22. The mammalian cell described in the above item 21, wherein the DNA which encodes an antibody is at least one of a DNA encoding an antibody H chain and a DNA encoding an antibody L chain.

23. The mammalian cell described in any one of the above items 18 to 22, into which an expression vector selected from the following (a) to (d) is introduced:

(a) an expression vector which comprises a gene fragment comprising a DNA encoding a H chain of an antibody and also comprises a pair of transposon sequences at both terminals of the gene fragment, an expression vector which comprises a gene fragment comprising a DNA encoding a L chain of an antibody and also comprises a pair of transposon sequences at both terminals of the gene fragment and an expression vector which comprises a gene fragment comprising a selectable marker gene and also comprises a pair of transposon sequences at both terminals of the gene fragment (b) an expression vector which comprises a gene fragment comprising a DNA encoding a H chain of an antibody and a selectable marker gene and also comprises a pair of transposon sequences at both terminals of the gene fragment and an expression vector which comprises a gene fragment comprising a DNA encoding a L chain of an antibody and also comprises a pair of transposon sequences at both terminals of the gene fragment, (c) an expression vector which comprises a gene fragment comprising a DNA encoding a L chain of an antibody and a selectable marker gene and also comprises a pair of transposon sequences at both terminals of the gene fragment and an expression vector which comprises a gene fragment comprising a DNA encoding a H chain of an antibody and also comprises a pair of transposon sequences at both terminals of the gene fragment, and (d) an expression vector which comprises a gene fragment comprising a DNA encoding a H chain and a L chain of an antibody and a selectable marker gene and also comprises a pair of transposon sequences at both terminals of the gene fragment.

24. The mammalian cell described in any one of the above item 18 to 23, wherein the cell is a cell capable of surviving and proliferating in a serum-free medium;

25. The mammalian cell described in any one of the above items 18 to 24, wherein the cell is any one suspension mammalian cell selected from a suspension CHO cell in which a CHO cell is adapted to suspension culture, a PER.C6 cell, a rat myeloma cell YB2/3HL.P2.G11.16Ag.20 (or also called YB2/0) and a suspension mouse myeloma cell NS0 adapted to suspension culture;

26. The mammalian cell described in the above item 25, wherein the CHO cell is any one selected from CHO-K1, CHO-K1SV, DUKXB11, CHO/DG44, Pro-3 and CHO-S;

27. The mammalian cell described in any one of the above items 19 to 26, wherein the selectable marker gene is a cycloheximide resistance gene;

28. The mammalian cell described in the above item 27, wherein the cycloheximide resistance gene is a gene encoding a mutant of human ribosomal protein L36a;

29. The mammalian cell described in any one of the above items 19 to 28, wherein a pair of the transposon sequences are nucleotide sequences derived from a pair of DNA-type transposons which function in a mammalian cell;

30. The mammalian cell described in the above item 29, wherein the nucleotide sequences derived from a pair of the DNA-type transposons are nucleotide sequences derived from a pair of Tol1 transposons or nucleotide sequences derived from a pair of Tol2 transposons;

31. The mammalian cell described in the above item 30, wherein the nucleotide sequences derived from a pair of the Tol2 transposons are the nucleotide sequence shown in SEQ ID NO:2 and the nucleotide sequence shown in SEQ ID NO:3;

32. The mammalian cell described in the above item 30, wherein the nucleotide sequences derived from a pair of the Tol1 transposons are the nucleotide sequence shown in SEQ ID NO:14 and the nucleotide sequence shown in SEQ ID NO:15;

33. An expression vector, which comprises a gene fragment comprising a DNA encoding a protein of interest, and also comprises a pair of transposon sequences at both terminals of the gene fragment;

34. The expression vector described in the above item 33, wherein a pair of the transposon sequences are nucleotide sequences derived from a pair of Tol1 transposons or nucleotide sequences derived from a pair of Tol2 transposons.

35. The protein expression vector described in the above item 34, wherein the nucleotide sequences derived from a pair of the Tol2 transposons are the nucleotide sequence shown in SEQ ID NO:2 and the nucleotide sequence shown in SEQ ID NO:3; and 36. The expression vector described in the above item 34, wherein the nucleotide sequences derived from a pair of the Tol1 transposons are the nucleotide sequence shown in SEQ ID NO:14 and the nucleotide sequence shown in SEQ ID NO:15.

This invention relates to a method for producing a protein of interest, comprising introducing at least one expression vector which comprises a gene fragment comprising a DNA encoding a protein of interest and also comprises transposon sequences at both terminals of the gene fragment, into a suspension mammalian cell; integrating the gene fragment inserted between a pair (two) of the transposon sequences, into a chromosome of the mammalian cell to obtain a suspension mammalian cell which expresses said protein of interest; and suspension-culturing the mammalian cell.

Examples of the method for producing a protein of interest in the present invention (hereinafter referred to as the method of the present invention) comprise a method for producing a protein of interest, which comprises the following steps (A) to (C).

(A) a step of simultaneously introducing the following expression vectors (a) and (b) into a suspension mammalian cell:

(a) at least one expression vector which comprises a gene fragment comprising a DNA encoding a protein of interest and also comprises transposon sequences at both terminals of the gene fragment, (b) a vector which comprises a DNA encoding a transposase which recognizes the transposon sequences and has activity of transferring a gene fragment inserted between a pair of the transposon sequences into a chromosome, (B) a step of expressing transiently the transposase from the expression vector (b) which is introduced into the suspension mammalian cell in the step (A) to integrate the gene fragment inserted between a pair of the transposon sequences into a chromosome of the mammalian cell to obtain a suspension mammalian cell which expresses the protein of interest, and (C) a step of suspension-culturing the suspension mammalian cell which expresses the protein of interest obtained in the step (B) to produce the protein of interest.

In addition, the present invention relates to a suspension mammalian cell, into which at least one of expression vector which comprises a gene fragment comprising a DNA encoding a protein of interest and also comprises a pair of transposon sequences at both terminals of the gene fragment and an expression vector is introduced to integrate the gene fragment inserted between the pair of transposon sequences into chromosome, and which produces the protein of interest.

In the present invention, the protein of interest is a protein comprised of one or more polypeptides, and according to the method of the invention, it can carry out any of the expression of at least one of the protein of interest and/or expression of at least one polypeptide.

The at least one of expression vectors which comprises a gene fragment comprising a DNA encoding a protein of interest and also comprises a pair of transposon sequences at both terminals of the gene fragment means one or two or more species of the expression vector. Particularly, in order to express a protein of interest comprised of two or more polypeptides, it is necessary to use two or more expression vectors which comprise a gene fragment including a DNA encoding respective polypeptides and also comprise a pair of transposon sequences at both terminals of the gene fragment.

More particularly, for example, when the above-mentioned protein of interest comprised of two or more polypeptides is an antibody, a H chain and a L chain of an antibody may be expressed using one expression vector or may be expressed using two expression vectors of a vector which expresses the H chain and a vector which expresses the L chain, respectively.

According to the method of the present invention, it can produce a protein of interest using a suspension mammalian cell which produces the protein of interest, in which a gene fragment inserted between a pair of transposon sequences is integrated into chromosome, by introducing the expression vector which comprises a gene fragment including a DNA encoding the protein of interest and also comprises a pair of transposon sequences at both terminals of the gene fragment.

The selectable marker gene to be used as an index of gene insertion may be integrated into the same vector as the expression vector which comprises the DNA encoding the protein of interest or may be integrated into a different vector.

That is, at least one of the expression vectors which comprise a gene fragment including a DNA encoding a the protein of interest and also comprise a pair of transposon sequences at both terminals of the gene fragment may be used as the expression vector which comprises a gene fragment including a DNA encoding a protein of interest and a selectable marker gene and also comprises a pair of transposon sequences at both terminals of the gene fragment.

Also, in addition to the expression vector which comprises a gene fragment including a DNA encoding a the protein of interest and also comprises a pair of transposon sequences at both terminals of the gene fragment, an expression vector which comprises a gene fragment including a selectable marker gene and also comprises a pair of transposon sequences at both terminals of the gene fragment may be further introduced into a mammalian cell.

Specifically, examples of the method for producing a protein of interest of the present invention include a method, comprising the following steps (A) to (C):
(A) a step of simultaneously introducing the following expression vectors (a) and (b) into a suspension mammalian cell:
  (a) an expression vector which comprises a gene fragment comprising a DNA encoding a protein of interest and also comprises a pair of transposon sequences at both terminals of the gene fragment,
  (b) a vector which comprises a DNA encoding a transposase which recognizes the transposon sequences and has activity of transferring the gene fragment inserted between a pair of the transposon sequences into a chromosome,
(B) a step of expressing the transposase transiently from the expression vector (b) which is introduced into the suspension mammalian cell in the step (A) to integrate the gene fragment inserted between a pair of the transposon sequences into a chromosome of the mammalian cell and obtaining a suspension mammalian cell which expresses the protein of interest, and
(C) a step of suspension-culturing the suspension mammalian cell which expresses the protein of interest obtained in the step (B) to produce the protein of interest.

In addition, examples of the method for producing a protein of interest of the present invention include a method, comprising the following steps (A) to (C):
(A) a step of simultaneously introducing the following expression vectors (a), (b) and (c) into a suspension mammalian cell:
  (a) at least one expression vector which comprises a gene fragment comprising a DNA encoding a protein of interest and also comprises a pair of transposon sequences at both terminals of the gene fragment,
  (b) an expression vector which comprises a selectable marker and a pair of transposon sequences at both terminals of the selectable marker,
  (c) a vector which comprises a DNA encoding a transposase which recognizes the transposon sequences and has activity of transferring the gene fragment inserted between a pair of the transposon sequences into a chromosome,
(B) a step of expressing transiently the transposase transiently from the expression vector (c) which is introduced into the suspension mammalian cell in the step (A) to integrate the gene fragment inserted between a pair of the transposon sequences into a chromosome of the mammalian cell and obtaining a suspension mammalian cell which expresses the protein of interest, and
(C) a step of suspension-culturing the suspension mammalian cell which expresses the protein of interest obtained in the step (B) to produce the protein of interest.

The present invention relates to a suspension mammalian cell, into which at least one expression vector which comprises a gene fragment comprising a DNA encoding a protein of interest and also comprises a pair of transposon sequences at both terminals of the gene fragment and an expression vector which comprises a selectable marker and a pair of transposon sequences at both terminals of the selectable marker are introduced to integrate the gene fragment and the selectable marker inserted between a pair of the transposon sequences into a chromosome, and which produces a protein of interest.

In addition, the present invention relates to a suspension mammalian cell into which a protein expression vector which comprises a gene fragment which comprising a DNA encoding a protein of interest and a selectable marker, and also comprises a pair of transposon sequences at both terminals of the gene fragment is introduced, to integrate the gene fragment inserted between a pair of the transposon sequences into a chromosome, and which produces a protein of interest.

Furthermore, examples of the suspension mammalian cell which produces a protein of interest of the present invention include a suspension mammalian cell into which an expression vector (a) comprising a gene fragment comprising a DNA encoding a protein of interest and a selectable marker gene and also comprising transposon sequences at both terminals of the gene fragment, and a vector (b) comprising a DNA encoding a transposase (a transferase) which recognizes the transposon sequences and has activity of transferring the gene fragment inserted between a pair of the transposon sequences into a chromosome to integrate the gene fragment inserted between a pair of the transposon sequences into the chromosome are simultaneously introduced and which produces the protein of interest.

According to the present invention, the number of expression vectors which comprise a gene fragment including a DNA encoding the protein of interest and also comprise a pair of transposon sequences at both terminals of the gene fragment, to be introduced into a suspension mammalian cell, is not particularly limited as long as expression and production of the protein of interest can be carried out by the mammalian cell, and examples include preferably 1 to 20 species of expression vectors, more preferably 2 to 10 species of expression vectors, can be mentioned, and for example, 3 to 8 species of expression vectors, 4 to 7 species of expression vectors, 1 to 6 species of expression vectors, 1 to 5 species of expression vectors, 1 to 4 species of expression vectors and 1 to 3 species of expression vectors are preferable.

In addition, examples of the embodiment of the present invention include a method for increasing integration of a gene fragment inserted between a pair of transposon sequences into chromosome of the mammalian cell, by simultaneously introducing into the suspension mammalian cell (a) at least one of expression vector which comprises a gene fragment comprising a DNA encoding a protein of interest and also comprises a pair of transposon sequences at both terminals of the gene fragment and (b) a vector which comprises a DNA encoding transposase capable of recognizing the transposon sequences and having the activity to introduce the gene fragment inserted between the pair of transposon sequences to chromosome, a method for integrating a DNA encoding a protein of interest into chromosome of the mammalian cell at a high frequency and a suspension mammalian cell which is obtained by the methods and can produce a protein of interest.

The term "transposon" in the present specification is a transposable genetic element and means a gene unit which moves on a chromosome or from a chromosome to another chromosome (transposition) while keeping a certain structure.

The transposon comprises a repeating transposon sequences (also called inverted repeat sequence (IR sequence) or terminal inverted repeat sequence (TIR sequence)) which positions in the same direction or the reverse direction at both terminals of a gene unit and a nucleotide sequence encoding a transposase which recognizes the transposon sequence to introduce a gene existing between the transposon sequences.

The transposase translated from the transposon can introduce a DNA by recognizing transposon sequences of both terminals of the transposon, cleaving out the DNA fragment inserted between a pair of the transposon sequences and inserting the fragment into the site to be introduced.

The term "transposon sequence" in the present specification means the nucleotide sequence of a transposon recognized by a transposase and has the same meaning as the IR sequence or TIR sequence. A DNA comprising the nucleotide sequence may comprise an imperfect repeating moiety as long as it can be introduced (inserted into other position in the genome) by the activity of a transposase, and there is a transposon sequence specific to a transposase.

As the transposon sequence to be used in the invention, a nucleotide sequence derived from a DNA-type transposon is preferable, and a nucleotide sequence derived from a pair of natural or artificial DNA-type transposons, which can be recognized by a transposase and be transposed in mammalian cells, is more preferable.

Examples of the nucleotide sequence derived from a DNA-type transposon include the nucleotide sequences derived from the medaka fish-derived Tol1 transposon and Tol2 transposon, the Sleeping Beauty reconstructed from a non-autonomous transposon existed in an *Onchorhynchus* fish genome, the frog-derived artificial transposon Frog Prince and the insect-derived transposon PiggyBac.

Particularly, among them, the nucleotide sequences derived from the medaka fish-derived Tol2 transposon comprising the nucleotide sequence shown in SEQ ID NO:6 and the medaka fish-derived Tol2 transposon comprising the nucleotide sequence shown in SEQ ID NO:13 are preferable.

Examples of the nucleotide sequence derived from a pair of Tol2 transposons include the nucleotide sequence at positions 1 to 2229 and the nucleotide sequence at positions 4148 to 4682 in the Tol2 transposon nucleotide sequence shown in SEQ ID NO:6 of Sequence Listing.

As the nucleotide sequence derived from a pair of Tol2 transposons, the nucleotide sequence at positions 1 to 200 (SEQ ID NO:2) (hereinafter referred to as "Tol2-L sequence") and the nucleotide sequence at positions 2285 to 2788 (SEQ ID NO:3) (hereinafter referred to as "Tol2-R sequence") in the Tol2 transposon nucleotide sequence shown in SEQ ID NO:1 of Sequence Listing are more preferable.

As the transposon sequence derived from a pair of Tol1 transposons, example include the nucleotide sequence comprising a nucleotide sequence at positions 1 to 157 and the nucleotide sequence at positions the 1748 to 1855 in the Tol1 transposon nucleotide sequence shown in SEQ ID NO:13 of Sequence Listing.

As the transposon sequence derived from a pair of Tol1 transposons, the nucleotide sequence at positions 1 to 200 (SEQ ID NO:14) (hereinafter referred to as "Tol1-L sequence") and the nucleotide sequence at positions 1351 to 1855 (SEQ ID NO:15) (hereinafter referred to as "Tol1-R sequence") in the Tol1 transposon nucleotide sequence shown in SEQ ID NO:13 of Sequence Listing are more preferable.

Examples of the transposon sequence to be used in the invention include transposon sequences of which transposition reactions are controlled by using a partial sequence of a transposon sequence derived from the above-mentioned transposon, by adjusting the length of the nucleotide sequence and by modifying the nucleotide sequence due to addition, deletion or substitution.

As the method for producing the protein of the interest of the present invention, examples also include a method in which at least one of the protein of interest is produced using at least two of transposon sequence and at least two of transposase.

Specifically, examples include a protein production method which comprises the steps of introducing a vector comprising a DNA encoding a first protein of interest inserted into two Tol1 transposon sequences, a vector comprising a DNA encoding a second protein of interest inserted into two Tol2 transposon sequences, a Tol1 transposase expression vector and a Tol2 transposon expression vector, simultaneously or in order into chromosome of the mammalian cell and thereby obtaining a mammalian cell which produces the two proteins of interest.

In addition, the first protein of interest and the second protein of interest may be the same, and productivity of the protein of interest can also be improved by increasing the number of copies of the gene to be introduced into the cell.

Regarding the control of the transposition reaction of a transposon, the transposition reaction can be accelerated or suppressed by accelerating or suppressing recognition of the transposon sequence by a transposase, respectively. In addition, with regard to the transposition reaction of transposon, the transposition reaction can be enhanced by shortening the length of the nucleotide sequence inserted between a pair (two) of the transposon sequences and the transposition reaction can be lowered by elongating the length. Therefore, when a protein of interest comprising plural proteins is expressed and prepared, the proteins of interest can be prepared by inserting DNA encoding each protein into a different expression vector, integrating the DNA in its chromosome of a host cell and can preparing a suspension mammalian cell which is able to prepare the protein of interest to produce the protein of interest by using the cell.

The term "transposase" in the present specification means an enzyme which recognizes nucleotide sequences having transposon sequences and transfers a gene fragment existing between the nucleotide sequences on a chromosome or from the chromosome to another chromosome.

Examples of the transposase include enzymes derived from Tol1 and Tol2 which are derived from medaka fish, the Sleeping Beauty (SB) reconstructed from a non-autonomous transposon existed in an *Onchorhynchus* fish genome, Sleeping Beauty 11 (SB11), the artificial transposon Frog prince (FP) which is derived from frog and the transposon PiggyBac (PB) which is derived from insect.

As the transposase, a native enzyme may be used, and any transposase in which a part of its amino acids are substituted, deleted, inserted and/or added may be used as long as the same transposition activity as the transposase is maintained. By controlling the enzyme activity of the transposase, the transposition reaction of the DNA existing between the transposon sequences can be controlled.

In order to analyze whether or not it possesses a transposition activity similar to that of transposase, it can be measured by the 2-components analyzing system disclosed in Japanese Published Unexamined Patent Application No. 235575/2003.

Particularly, whether or not a non-autonomous Tol2 element can be transferred and inserted into a mammalian cell chromosome by the activity of a transposase can be analyzed by separately using a plasmid comprising a Tol2 transposase-deleted Tol2 transposon (Tol2-derived non-autonomous transposon) and a plasmid comprising Tol2 transposase.

The term "non-autonomous transposon" in the present specification means a transposon which is lost a transposase existed inside the transposon and can not therefore perform its autonomous transposition. The non-autonomous transposon can transfer the DNA inserted between transposon sequences of the non-autonomous transposon into the host cell chromosome, by allowing a transposase protein, an mRNA encoding the transposase protein or a DNA encoding the transposase protein to simultaneously present in the cell.

The transposase gene means a gene encoding a transposase. In order to improve its expression efficiency in a mammalian cell, a sequence which adjusts a space between the Kozak's consensus sequence (Kozak M., *Nucleic Acids Res.*, 12, 857-872 (1984)) or a ribosome binding sequence, Shine-Dalgarno sequence and the initiation codon, to an appropriate distance (e.g., from 6 to 18 bases) may be connected to an upstream site of the translation initiation codon ATG of the gene.

According to the method of the invention, in order to integrate a gene fragment comprising a DNA encoding the protein of interest in at least one expression vector into the chromosome of a host cell, an expression vector which comprises the gene fragment comprising a DNA encoding the protein of interest and also comprises a pair of transposon sequences at both terminals of the gene fragment is introduced into the host cell, and a transposase is allowed to act upon the transposon sequences comprised in the expression vector which is introduced into the cell.

In order to allow a transposase to act upon the transposon sequences comprised in the expression vector which is introduced into the cell, the transposase may be injected into the cell, or an expression vector comprising a DNA encoding at least one protein of interest or a DNA encoding a protein of interest may be introduced into the host cell together with an expression vector comprising a DNA encoding the protein of interest and a selectable marker gene. In addition, by introducing an RNA encoding a transposase gene into the host cell, the transposase may be expressed in the cell.

The expression vector is not particularly limited. Any expression vector can be used by optionally selecting from the expression vectors known to those skilled in the art, depending on a host cell into which an expression vector comprising a transposase gene is introduced; the use; and the like.

In the case where a protein of interest comprised of two or more polypeptides or two or more proteins of interest is produced by the method of the invention, a protein producing cell in which a DNA encoding each protein is integrated in to a chromosome of a host cell can be prepared by inserting the DNA encoding each of protein on the same expression vector or inserting the DNA into respective different expression vector and introducing the expression vector into a host cell.

The transposase may be inserted into an expression vector to express together with the protein of interest or may be inserted into a vector different from the expression vector. The transposase may be allowed to act transiently or may be allowed to act continuously, but it is preferably to allow the transposase to act transiently in order to prepare a cell for stable production.

As the method for allowing the transposase to act transiently, examples include a method comprising preparing an expression vector which comprises a DNA encoding the transposase and an expression vector comprising a DNA encoding a protein of interest and then introducing both of the expression plasmids simultaneously into a host cell.

The term "expression vector" in the present specification means an expression vector to be used for introducing a mammalian cell and expressing a protein of interest. The expression vector used in the invention has a structure in which at least a pair of transposon sequences is present at both sides of an expression cassette.

The term "expression cassette" in the present specification means a nucleotide sequence which has a gene expression controlling region necessary for expressing a protein of interest and a sequence encoding the protein of interest. Examples of the gene expression controlling region include an enhancer, a promoter, and a terminator. The expression cassette may include a selectable marker gene.

Any promoter can be used, so long as it can function in an animal cell. Examples include a promoter of IE (immediate early) gene of cytomegalovirus (CMV), SV40 early promoter, a promoter of retrovirus, a metallothionein promoter, a heat shock promoter, SRα promoter, moloney murine leukemia virus, an enhancer and the like. Also, the enhancer of the IE gene of human CMV can be used together with the promoter.

The "selectable marker gene" means an optional other marker gene which can be used for distinguishing a cell to which a plasmid vector is introduced from a cell lacking of the vector.

Examples of the selectable marker gene include a drug resistance gene (a neomycin resistance gene, a dihydrofolate reductase (DHFR) gene, a puromycin resistance gene, a blasticidin resistance gene, a zeocin resistance gene, a hygromycin resistance gene, and a cycloheximide resistance gene (Japanese Published Unexamined Patent Application No. 262879/2002)), fluorescence and bio-luminescence marker genes (such as green fluorescent protein GFP) and the like.

In the invention, the preferable selectable marker is a drug resistance gene and particularly preferable selectable marker is a cycloheximide resistance gene. Further, drug resistance property and luminescence property of the selectable marker protein can also be changed by preparing an amino acid modified variant by genetically modifying the selectable maker gene or by controlling transcription or translation of the selectable marker gene (e.g., modification of a promoter, modification of an amino acid codon and the like). In addition, a selectable marker gene introduced cells having different drug resistance strengths can also be selected by adjusting the drug concentration.

For controlling drug resistance property and luminescence property of the selectable marker protein, it is preferable to use an as the attenuated selectable marker gene. The attenuated selectable marker gene is a selectable marker gene which is modified in such a manner that activity of the protein encoded by the selectable marker gene inside the cell is lowered.

Examples of the selectable marker gene which is modified in such a manner that the activity in the cell becomes low include (A) an selectable marker gene in which an amino acid sequence of a protein encoded by a selectable marker gene is modified so that activity of the protein in the cell is lowered and (B) an selectable marker gene in which a nucleotide sequence which controls expression of a selectable marker gene is modified or a nucleotide sequence inside of ORF (open reading frame) is modified so that the expression of the selectable marker gene is lowered.

Examples of the selectable marker gene in which an amino acid sequence of a protein encoded by a selectable marker gene is modified so that activity of the protein in the cell is lowered include the neomycin resistance gene described by Sauter et al. [*Biotech. Bioeng.*, 89, 530-538 (2005)] or Chen et al. [*Journal of Immunological Methods*, 295, 49-56 (2004)].

Examples of the method for lowering expression level of a protein in the cell by modifying a nucleotide sequence which controls expression of the selectable marker gene include a method for modifying the sequence of promoter sequence, terminator sequence, enhancer sequence, kozak's consensus sequence or Shine-Dalgarno sequence, which controls expression of the selectable marker gene. More specifically, examples include a method in which a promoter sequence which controls expression of a selectable marker gene is replaced by a weaker promoter sequence.

Examples of the method for lowering expression level of the protein in the cell by modifying a nucleotide sequence in the ORF of a selectable marker gene include a method in which a codon in the ORF is replaced by a synonymous codon having further lower frequency of codon usage in the cell.

Examples of the attenuated selectable marker gene of the invention include a selectable marker in which the above codon in the ORF of the gene is replaced by a synonymous codon having further lower frequency of codon usage in the cell.

In the cells of various biological species, the synonymous codon having further lower frequency of usage among each synonymous codon can be selected based on known literatures, data bases and the like.

As such a replacement by a synonymous codon having lower frequency of usage, specifically in the case of CHO cell, examples include replacement of the codon of leucine with TTA, replacement of the codon of arginine with CGA or CGT, replacement of the codon of alanine with GCG, replacement of the codon of valine with GTA, replacement of the codon of serine with TCG, replacement of the codon of isoleucine with ATA, replacement of the codon of threonine with ACG, replacement of the codon of proline with CCG, replacement of the codon of glutamic acid with GAA, replacement of the codon of tyrosine with TAT, replacement of the codon of lysine with AAA, replacement of the codon of phenylalanine with TTT, replacement of the codon of histidine with CAT, replacement of the codon of glutamine with CAA, replacement of the codon of asparagine with AAT, replacement of the codon of aspartic acid with GAT, replacement of the codon of cysteine with TGT and replacement of the codon of glycine with GGT.

In an attenuated selectable marker gene, the number of codons to be placed compared to the selectable marker gene before the modification is not particularly limited as long as a protein producing cell can be efficiently obtained, but it is preferable to replace codons corresponding to 20 or more amino acid residues.

In an attenuated selectable marker gene, the number of bases to be modified compared to the selectable marker gene before modification is not particularly limited, but it is preferable to modify 10% or more of the nucleotide sequence encoding the selectable marker gene.

In addition, in an attenuated selectable marker gene, the amino acid residues encoded by the codons to be replaced is not particularly limited, but preferable examples include leucine, alanine, serine and valine.

In the case of an attenuated selectable marker gene, in the case where the codons corresponding to leucine are replaced not particularly limited, but it is preferable to replace the codons corresponding to 70% or more of leucine residues among the codons corresponding to the total of the leucine residues contained in the selectable marker gene.

Also, in the case of an attenuated selectable marker gene, when the codons corresponding to alanine are replaced not particularly limited, but it is preferable to replace the codons corresponding to 70% or more of alanine residues among the codons corresponding to the total of the alanine residues contained in the selectable marker gene.

Specific examples of the attenuated selectable marker gene obtained by such as a modification in which codons are replaced with synonymous codons having lower frequency of usage include a neomycin resistance gene comprising the nucleotide sequence represented by SEQ ID NO:37, 38 or 39, a puromycin resistance gene comprising the nucleotide sequence represented by SEQ ID NO:41, 43 or 44, a Zeocin resistance gene consisting of the nucleotide sequence represented by SEQ ID NO:45 or 46 and a hygromycin resistance gene comprising the nucleotide sequence represented by SEQ ID NO:47 or 48.

In addition, it is possible to attenuate a selectable marker gene also by considerably increasing concentration of a drug in comparison with the conventionally used concentration when a drug-resistant cell is selected in preparing an antibody producing cell or by carrying out additional administration before the drug resistance gene metabolizes and degrades the drug.

Cycloheximide (hereinafter, referred sometimes to as CHX) is a protein synthesis inhibitor, and examples of using a CHX resistance gene as the selectable marker gene include known cases of yeast [Kondo K., *J. Bacteriol.*, 177, 24, 7171-7177 (1995)] and animal cells (JP-A-2002-262879).

In the case of animal cells, it has been revealed that a transformant expressing a protein encoded by the nucleotide sequence represented by SEQ ID NO:7 of SEQUENCE LISTING in which the 54-position proline of a human ribosomal protein subunit L36a encoded by the nucleotide sequence represented by SEQ ID NO:5 of SEQUENCE LISTING is replaced by glutamine provides resistance to cycloheximide. In addition, examples of the cycloheximide resistance marker include a mutant human ribosomal protein subunit L44 in which proline at position 54 of a human ribosomal protein subunit L44 is replaced by glutamine.

The method for introducing the above-mentioned protein expression vector comprising a transposon sequence, a plasmid vector for expressing a transposase or RNA is not particularly limited. Examples include calcium phosphate transfection, electroporation, a liposome method, a gene gun method, lipofection and the like.

Examples of the method for directly introducing a transposase in the form of a protein include a microinjection technique or supply into a cell by endocytosis. The gene introduction can be carried out by the method described in *Shin Idenshi Kogaku Handbook* (New Genetic Engineering Handbook), edited by Masami Muramatsu and Tadashi Yamamoto, published by Yodo-sha, ISBN 9784897063737.

The host cell may be any mammalian cell as long as it can be subcultured and stably express a protein of interest. Examples of the host cell include PER.C6 cell, human leukemia cell Namalwa cell, monkey cell COS cell, rat myeloma cell YB2/3HL.P2.G11.16Ag.20 (also referred to as YB2/0), mouse myeloma cell NS0, mouse myeloma cell SP2/0-Ag14, Syrian hamster cell BHK, HBT5637 (Japanese Unexamined Patent Application Publication No. 1998-000299), Chinese hamster ovarian cell CHO cell (*Journal of Experimental Medicine*, 108, 945 (1958); *Proc. Natl. Acad. Sci. USA.*, 601275 (1968); *Genetics*, 55, 513 (1968); *Chromosoma*, 41, 129 (1973); *Methods in Cell Science*, 18, 115 (1996); *Radiation Research*, 148, 260 (1997); *Proc. Natl. Acad. Sci. USA.*, 77, 4216 (1980); *Proc. Natl. Acad. Sci.*, 60, 1275 (1968); *Cell*, 6, 121 (1975); *Molecular Cell Genetics, Appendix I, II* (pp. 883-900)), CHO/DG44, CHO-K1 (ATCC CCL-61), DUKXB11 (ATCC CCL-9096), Pro-5 (ATCC CCL-1781), CHO-S (Life Technologies, Cat #11619), Pro-3 and subclonal cell line of CHO cell.

In addition, the above-mentioned host cell can also be used in the protein production method of the invention by modifying the cell so as to be suitable for the protein production, due to modification of chromosomal DNA, introduction of an exogenous gene, and the like.

Further, in order to control the sugar chain structure bound to a protein of interest to be produced, Lec13 which acquired lectin resistance [*Somatic Cell and Molecular Genetics*, 12, 55 (1986)] and a CHO cell from which α1,6-fucosyltransferase gene is deleted (WO2005/35586, WO2002/31140), a cell deficient in GDP-mannose 4,6-dehydratase (GMD) and a cell deficient in Fx protein can also be used as the host cell.

In the present invention, the protein of interest also includes any one of a protein consisting of at least one polypeptide and a complex protein consisting of two or more polypeptides of protein. In addition, a protein and a polypeptide are synonymous in the invention, but a protein molecule having a relatively low molecular weight or a protein constituting a complex protein may be defined sometimes as a polypeptide.

The protein of interest in the invention may be any protein or polypeptide as long as it can be expressed by the method of the invention. Particularly, examples of the protein of interest include a human serum protein, an albumin binding protein, a peptide hormone, a growth factor, a cytokine, a blood coagulation factor, a fibrinolytic protein, an antibody, a selectable marker protein, a membrane protein, partial fragments of various proteins and the like. Particularly, examples of the protein of interest include human vein immunoglobulin (IVIG), erythropoietin (EPO), albumin, growth hormone (GH), follicle-stimulating hormone (FSH), hepatocyte growth factor (HGF), insulin, insulin-like growth factor-I (IGF-I), interferon (INF), Fas ligand, blood coagulation factors (II, VII, VIII, IX, X), prothrombin, fibrinogen, protein C, protein S, antithrombin III (ATIII), the tissue plasminogen activator (tPA), a monoclonal antibody, a polyclonal antibody and the like.

The antibody is a molecule comprising of an antibody heavy chain (H chain) polypeptide and two antibody light chain (L chain) polypeptides, and as a subclass, IgA, IgD, IgE, IgG and IgM subclasses are known. Further, the IgG is classified into IgG1, IgG2, IgG3 and IgG4.

The IgG antibody is a heterotetrameric molecule consisting of two H chain polypeptides and two L chain polypeptides. Each of the H chain and L chain consists of a variable region (V) which relates to the antigen binding and a constant region (C) and each of them is called VH, CH, VL or CL, respectively. The CH region is further classified into CH1, CH2 and CH3 regions, and the CH2 and CH3 regions are called in combination as Fc region or simply as Fc.

The antibody includes a monoclonal antibody which reacts with a single epitope, a polyclonal antibody which reacts with two or more epitopes and a recombinant antibody.

The monoclonal antibody is an antibody which is secreted by a single clonal antibody producing cell and recognizes only one epitope (also called an antigenic determinant), and the amino acid sequence (primary structure) constituting a monoclonal antibody is uniform.

The polyclonal antibody is a mixture of monoclonal antibodies and can react with two or more epitopes.

Examples of the recombinant antibody include a chimeric antibody, a humanized antibody, a human antibody, a Fc fusion protein, Fc amino acid modified antibody, and a multivalent antibody and a partial fragment thereof. An amino acid modified antibody may have an amino acid modification in either a variable region or a constant region and antibody activity is controlled.

The multivalent antibody includes a multivalent antibody which reacts with two or more different epitopes on one antigen, a multivalent antibody which react with two or more different antigens and the like, but it may include any multivalent antibody. In addition, the multivalent antibody may be any multivalent antibody having any structure as long as it retains the binding activity to the antigen (WO2001/77342, U.S. Pat. No. 7,612,181 and WO2009/131239).

According to the producing method of the present invention, any of the above protein of interest and/or the peptide of interest can be expressed and produced.

Examples of the cell into which a DNA encoding at least one protein of interest of the present invention include an antibody producing cell prepared by the following steps (A) and (B).

Step (A) a step of simultaneously introducing both of one combination of expression vector selected from the following (a) to (c) or expression vector (d) and expression vector (e) into a suspension mammalian cell:

(a) an expression vector which comprises a gene fragment comprising a DNA encoding a H chain of an antibody and also comprises a pair of transposon sequences at both terminals of the gene fragment, an expression vector which comprises a gene fragment comprising a DNA encoding a L chain of an antibody and also comprises a pair of transposon sequences at both terminals of the gene fragment and an expression vector which comprises a gene fragment comprising a selectable marker gene and also comprises a pair of transposon sequences at both terminals of the gene fragment (b) an expression vector which comprises a gene fragment comprising a DNA encoding a H chain of an antibody and a selectable marker gene and also comprises a pair of transposon sequences at both terminals of the gene fragment and an expression vector which comprises a gene fragment comprising a DNA encoding a L chain of an antibody and also comprises a pair of transposon sequences at both terminals of the gene fragment, (c) an expression vector which comprises a gene fragment comprising a DNA encoding a L chain of an antibody and a selectable marker gene and also comprises a pair of transposon sequences at both terminals of the gene fragment and an expression vector which comprises a gene fragment comprising a DNA encoding a H chain antibody of an antibody and also comprises a pair of transposon sequences at both terminals of the gene fragment, and (d) an expression vector which comprises a gene fragment comprising a DNA encoding a H chain and a L chain of an antibody and a selectable marker gene and also comprises a pair of transposon sequences at both terminals of the gene fragment;

(e) a vector comprising a DNA encoding a transposase which recognizes the transposon sequences and has activity of transferring a gene fragment inserted between a pair of the transposon sequences into a chromosome; and Step (B) a step of selecting a suspension mammalian cell which expresses an antibody in which the genes of the above H chain, L chain and selectable marker which are inserted between a pair of the transposon sequence are integrated into a chromosome of the above mammalian cell by transiently expressing the transposase from the expression vector (e) which is introduced into the suspension mammalian cell in the step (A).

Examples of the method for producing an antibody of the present invention include a method for producing a protein of interest comprising the following steps (A) to (C).

Step (A) a step of simultaneously introducing one combination of expression vector selected from the following (a) to (c) or expression vector (d), and expression vector (e) into a suspension mammalian cell:

(a) an expression vector which comprises a gene fragment comprising a DNA encoding a H chain of an antibody and also comprises a pair of transposon sequences at both terminals of the gene fragment, an expression vector which comprises a gene fragment comprising a DNA encoding a L chain of an antibody and also comprises a pair of transposon sequences at both terminals of the gene fragment and an expression vector which comprises a gene fragment comprising a selectable marker gene and also comprises a pair of transposon sequences at both terminals of the gene fragment (b) an expression vector which comprises a gene fragment comprising a DNA encoding a H chain of an antibody and a selectable marker gene and also comprises a pair of transposon sequences at both terminals of the gene fragment and an expression vector which comprises a gene fragment comprising a DNA encoding a L chain of an antibody and also comprises a pair of transposon sequences at both terminals of the gene fragment, (c) an expression vector which comprises a gene fragment comprising a DNA encoding a L chain of an antibody and a selectable marker gene and also comprises a pair of transposon sequences at both terminals of the gene fragment and an expression vector which comprises a gene fragment comprising a DNA encoding a H chain of an antibody and also comprises a pair of transposon sequences at both terminals of the gene fragment, and (d) an expression vector which comprises a gene fragment comprising a DNA encoding a H chain and a L chain of an antibody and a selectable marker gene and also comprises a pair of transposon sequences at both terminals of the gene fragment;

(e) a vector comprising a DNA encoding a transposase which recognizes the transposon sequences and has activity of transferring a gene fragment inserted between a pair of the transposon sequences into a chromosome;

Step (B) a step of obtaining a suspension mammalian cell which expresses an antibody in which the genes of the above H chain, L chain and selectable marker which are inserted between a pair of the transposon sequence are integrated into a chromosome of the above mammalian cell by transiently expressing the transposase from the expression vector (e) which is introduced into the suspension mammalian cell in the step (A); and Step (C) a step of producing the antibody by suspension-culturing a suspension mammalian cell obtained in the step (B) which expresses an antibody.

In addition, the present invention includes a method for producing a cell line which has a high antibody productivity and a method for screening the cell line comprising the following steps (A) and (B).

Step (A) a step of simultaneously introducing one combination of expression vector selected from the following (a) to (c) or expression vector (d), and expression vector (e) into a suspension mammalian cell:

(a) an expression vector which comprises a gene fragment comprising a DNA encoding a H chain of an antibody and also comprises a pair of transposon sequences at both terminals of the gene fragment, an expression vector which comprises a gene fragment comprising a DNA encoding a L chain of an antibody and also comprises a pair of transposon sequences at both terminals of the gene fragment and an expression vector which comprises a gene fragment comprising a selectable marker gene and also comprises a pair of transposon sequences at both terminals of the gene fragment (b) an expression vector which comprises a gene fragment comprising a DNA encoding a H chain of an antibody and a selectable marker gene and also comprises a pair of transposon sequences at both terminals of the gene fragment and an expression vector which comprises a gene fragment comprising a DNA encoding a L chain of an antibody and also comprises a pair of transposon sequences at both terminals of the gene fragment, (c) an expression vector which comprises a gene fragment comprising a DNA encoding a L chain of an antibody and a selectable marker gene and also comprises a pair of transposon sequences at both terminals of the gene fragment and an expression vector which comprises a gene fragment comprising a DNA encoding a H chain of an antibody and also comprises a pair of transposon sequences at both terminals of the gene fragment, and (d) an expression vector which comprises a gene fragment comprising a DNA encoding a H chain and a L chain of an antibody and a selectable marker gene and also comprises a pair of transposon sequences at both terminals of the gene fragment;

(e) a vector comprising a DNA encoding a transposase which recognizes the transposon sequences and has activity of transferring a gene fragment inserted between a pair of the transposon sequences into a chromosome; and Step (B) a step of selecting a suspension mammalian cell which highly expresses an antibody in which the genes of the above H chain, L chain and selectable marker which are inserted between a pair of the transposon sequence are integrated into a chromosome of the above mammalian cell by transiently express the transposase from the expression vector (e) which is introduced into the suspension mammalian cell in the step (A).

In addition, the present invention includes a method for producing an antibody comprising the following steps (A), (B) and (C).

Step (A) a step of simultaneously introducing one combination of expression vector selected from the following (a) to (c) or expression vector (d) and expression vector (e) into a suspension mammalian cell:

(a) an expression vector which comprises a gene fragment comprising a DNA encoding a H chain of an antibody and also comprises a pair of transposon sequences at both terminals of the gene fragment, an expression vector which comprises a gene fragment comprising a DNA encoding a L chain of an antibody and also comprises a pair of transposon sequences at both terminals of the gene fragment and an expression vector which comprises a gene fragment comprising a selectable marker gene and also comprises a pair of transposon sequences at both terminals of the gene fragment (b) an expression vector which comprises a gene fragment comprising a DNA encoding a H chain of an antibody and a selectable marker gene and also comprises a pair of transposon sequences at both terminals of the gene fragment and an expression vector which comprises a gene fragment comprising a DNA encoding a L chain of an antibody and also comprises a pair of transposon sequences at both terminals of the gene fragment, (c) an expression vector which comprises a gene fragment comprising a DNA encoding a L chain of an antibody and a selectable marker gene and also comprises a pair of transposon sequences at both terminals of the gene fragment and an expression vector which comprises a gene fragment comprising a DNA encoding a H chain of an antibody and also comprises a pair of transposon sequences at both terminals of the gene fragment, and (d) an expression vector which comprises a gene fragment comprising a DNA encoding a H chain and a L chain of an antibody and a selectable marker gene and also comprises a pair of transposon sequences at both terminals of the gene fragment;

(e) a vector comprising a DNA encoding a transposase which recognizes the transposon sequences and has activity of transferring a gene fragment inserted between a pair of the transposon sequences into a chromosome;

Step (B) a step of obtaining a suspension mammalian cell which expresses an antibody in which the genes of the above H chain, L chain and selectable marker which are inserted between a pair of the transposon sequence are integrated into a chromosome of the above mammalian cell by transiently expressing the transposase from the expression vector (e) which is introduced into the suspension mammalian cell in the step (A); and Step (C) a step of producing the antibody by suspension-culturing a suspension mammalian cell obtained in the step (B) which expresses an antibody.

Examples of the mammalian cell into which a DNA encoding at least one protein of interest of the present invention include a polyclonal antibody producing cell into which several different antibody genes are introduced, a complex molecule producing cell and the like.

Examples of a polyclonal antibody producing cell include a cell into which at least two or more different monoclonal antibody genes are introduced, a cell into which genes of several monoclonal antibodies against several antigens are introduced, a cell which is immunized by an antigen and into which a gene library of a non-human antibody is introduced, a cell into which a gene library of antibody derived from a patient is introduced and the like.

The complex molecule producing cell may be any cell as long as DNAs encoding respective proteins which are co-expressed in a cell to form a complex molecule is introduced. Specific examples include a cell into which FcγRIII (CD16) and common 7 chain are co-transfected, a cell into which neonatal Fc receptor (FcRn) and 132 macrogloblin are co-expressed, a cell into which CD98 and LAT1 are co-transfected (WO2007/114496) and the like The antibody which is produced by the antibody production method of the present invention can be any antibody and examples include an antibody which recognize a tumor-related antigen, an antibody which recognizes an allergy- or inflammation-related antigen, an antibody which recognizes an cardiovascular disease-related antigen, an antibody which recognizes an antigen which relating to autoimmune diseases, an antibody which recognizes virus- or bacterial infection-related antigen and the like.

Examples of the tumor-related antigen includes CD1a, CD2, CD3, CD4, CD5, CD6, CD7, CD9, CD10, CD13, CD19, CD20, CD21, CD22, CD25, CD28, CD30, CD32, CD33, CD38, CD40, CD40 ligand (CD40L), CD44, CD45, CD46, CD47, CD52, CD54, CD55, CD55, CD59, CD63, CD64, CD66b, CD69, CD70, CD74, CD80, CD89, CD95, CD98, CD105, CD134, CD137, CD138, CD147, CD158, CD160, CD162, CD164, CD200, CD227, adrenomedullin, angiopoietin related protein 4 (ARP4), aurora, B7-H1, B7-DC, integlin, bone marrow stromal antigen 2 (BST2), CA125, CA19.9, carbonic anhydrase 9 (CA9), cadherin, cc-chemokine receptor (CCR) 4, CCR7, carcinoembryonic antigen (CEA), cysteine-rich fibroblast growth factor receptor-1 (CFR-1), c-Met, c-Myc, collagen, CTA, connective tissue growth factor (CTGF), CTLA-4, cytokeratin-18, DF3, E-catherin, epidermal growth facter receptor (EGFR), EGFRvIII, EGFR2 (HER2), EGFR3 (HER3), EGFR4 (HER4), endoglin, epithelial cell adhesion molecule (Ep-CAM), endothelial protein C receptor (EPCR), ephrin, ephrin receptor (Eph), EphA2, endotheliase-2 (ET2), FAM3D, fibroblast activating protein (FAP), Fc receptor homolog 1 (FcRH1), ferritin, fibroblast growth factor-8 (FGF-8), FGF8 receptor, basic FGF (bFGF), bFGF receptor, FGF receptor (FGFR) 3, FGFR4, FLT1, FLT3, folate receptor, Frizzled homologue 10 (FZD10), frizzled receptor 4 (FZD-4), G250, G-CSF receptor, ganglioside (such as GD2, GD3, GM2 and GM3), globo H, gp75, gp88, GPR-9-6, heparanase I, hepatocyte growth factor (HGF), HGF receptor, HLA antigen (such as HLA-DR), HM1.24, human milk fat globule (HMFG), hRS7, heat shock protein 90 (hsp90), idiotype epitope, insulin-like growth factor (IGF), IGF receptor (IGFR), interleukin (such as IL-6 and IL-15), interleukin receptor (such as IL-6R and IL-15R), integrin, immune receptor translocation associated-4 (IRTA-4), kallikrein 1, KDR, KIR2DL1, KIR2DL2/3, KS1/4, lamp-1, lamp-2, laminin-5, Lewis y, sialyl Lewis x, lymphotoxin-beta receptor (LTBR), LUNX, melanoma-associated chondroitin sulfate proteoglycan (MCSP), mesothelin, MICA, Mullerian inhibiting substance type II receptor (MISIIR), mucin, neural cell adhesion molecule (NCAM), Nec1-5, Notch1, osteopontin, platelet-derived growth factor (PDGF), PDGF receptor, platelet factor-4 (PF-4), phosphatidylserine, Prostate Specific Antigen (PSA), prostate stem cell antigen (PSCA), prostate specific membrane antigen (PSMA), Parathyroid hormone related protein/peptide (PTHrP), receptor activator of NF-kappaB ligand (RANKL), receptor for hyaluronic acid mediated motility (RHAMM), ROBO1, SART3, semaphorin 4B (SEMA4B), secretory leukocyte protease inhibitor (SLPI), SM5-1, sphingosine-1-phosphate, tumor-associated glycoprotein-72 (TAG-72), transferrin receptor (TfR), TGF-beta, Thy-1, Tie-1, Tie2 receptor, T cell immunoglobulin domain and mucin domain 1 (TIM-1), human tissue factor (hTF), Tn antigen, tumor necrosis factor (TNF), Thomsen-Friedenreich antigen (TF antigen), TNF receptor, tumor necrosis factor-related apoptosis-inducing ligand (TRAIL), TRAIL receptor (such as DR4 and DR5), system ASC amino acid transporter 2 (ASCT2), trkC, TROP-2, TWEAK receptor Fn14, type IV collagenase, urokinase receptor, vascular endothelial growth factor (VEGF), VEGF receptor (such as VEGFR1, VEGFR2 and VEGFR3), vimentin, VLA-4 and the like, and antibodies against the above antigens.

Further, examples of the antibody which recognizes a tumor-related antigen include [AntiCancer Res., 13, 331 (1993)], anti-GD3 antibody [Cancer Immunol. Immunother., 36, 260 (1993)], anti-GM2 antibody [Cancer Res., 54, 1511 (1994)], anti-CD52 antibody [Proc. Natl. Acad. Sci. USA, 89, 4285 (1992)], anti-MAGE antibody [British J. Cancer, 83, 493 (2000)], anti-HM1.24 antibody [Molecular Immunol., 36, 387 (1999)], anti-parathyroid hormone related protein (PTHrP) antibody [Cancer, 88, 2909 (2000)], anti-bFGF antibody, anti-FGF-8 antibody [Proc. Natl. Acad. Sci. USA, 86, 9911 (1989)], anti-bFGFR antibody, anti-FGFR1 antibody (WO2005/037235), anti-FGF-8R antibody [J. Biol. Chem., 265, 16455 (1990)], anti-IGF antibody [J. Neurosci. Res., 40, 647 (1995)], anti-IGF-IR antibody [J. Neurosci. Res, 40, 647 (1995)], anti-PSMA antibody [J. Urology, 160, 2396 (1998)], anti-VEGF antibody [Cancer Res, 57, 4593 (1997), Avastin®], anti-VEGFR antibody [Oncogene, 19, 2138 (2000), WO96/30046], anti-CD20 antibody [Curr. Opin. Oncol., 10, 548 (1998), U.S. Pat. No. 5,736,137, Rituxan®, Ocrelizumab, Ofatumumab], anti-EGFR antibody (Erbitux®, Vectivix®), anti-HER2 antibody (Proc. Natl. Acad. Sci. USA, 89, 4285 (1992), U.S. Pat. No. 5,725,856, Herceptin®, Pertuzumab), anti-HER3 antibody (US2008/0124345), c-Met antibody (U.S. Pat. No. 6,468,529), anti-CD10 antibody, anti-EGFR antibody (WO96/402010), anti-Apo-2R antibody (WO98/51793), anti-ASCT2 antibody (WO2010/008075), anti-CEA antibody [Cancer Res., 55 (23 suppl): 5935s-5945s, (1995)], anti-CD38 antibody, anti-CD33 antibody, anti-CD22 antibody, anti-CD20 amino acid modified antibody (Immunology, 115, 4393, 2010.), anti-EpCAM antibody, anti-A33 antibody, anti-folate receptor antibody (MRAb-003) and the like.

Examples of the antibody which recognizes an allergy- or inflammation-related antigen include anti-interleukin 6 antibody [Immunol. Rev., 127, 5 (1992)], anti-interleukin 6 receptor antibody [Molecular Immunol., 31, 371 (1994)], anti-interleukin 5 antibody [Immunol. Rev., 127, 5 (1992)], anti-interleukin 5 receptor antibody, anti-interleukin 4 antibody [Cytokine, 3, 562 (1991)], anti-interleukin 4 receptor antibody [J. Immunol. Meth., 217, 41 (1998)], anti-tumor necrosis factor antibody [Hybridoma, 13, 183 (1994)], anti-tumor necrosis factor receptor antibody [Molecular Pharmacol., 58, 237 (2000)], anti-CCR4 antibody [Nature, 400, 776 (1999)], anti-chemokine antibody [Peri et al., J. Immuno. Meth., 174, 249-257 (1994)], anti-chemokine receptor antibody [J. Exp. Med., 186, 1373 (1997)] and the like. Examples of the antibody which recognizes a cardiovascular disease-related antigen include anti-GpIIb/IIIa antibody [J. Immunol., 152, 2968 (1994)], anti-platelet-derived growth factor antibody [Science, 253, 1129 (1991)], anti-platelet-derived growth factor receptor antibody [J. Biol. Chem., 272, 17400 (1997)], anti-blood coagulation factor antibody [Circulation, 101, 1158 (2000)], anti-IgE antibody, anti-αVβ3 antibody, anti-α4β7 antibody, and the like.

Examples of the antibody which recognizes virus- or bacterial infection-related antigen includes anti-gp120 antibody [Structure, 8, 385 (2000)], anti-CD4 antibody [J. Rheumatology, 25, 2065 (1998)], anti-CCR5 antibody, anti-verotoxin antibody [J. Clin. Microbiol., 37, 396 (1999)], anti-M2 antibody (JP2003-235575) and the like.

The effector activity of a monoclonal antibody produced by the method of the present invention can be controlled by various methods. Examples of the known methods include a method for controlling an amount of fucose (hereinafter, referred to also as "core fucose") which is bound N-acetylglucosamine (GlcNAc) through α-1,6 bond in a reducing end of a complex type N-linked sugar chain which is bound to asparagine (Asn) at position 297 of an Fc region of an antibody (WO2005/035586, WO2002/31140, and WO00/61739), a method for controlling an effector activity by modifying amino acid residue(s) of an Fc region of the antibody, and the like. The effector activity of the monoclonal antibody produced by the method of the present invention can be controlled by using any of the methods.

The "effector activity" means an antibody-dependent activity which is induced via an Fc region of an antibody. As the effector activity, an antibody-dependent cellular cytotoxicity (ADCC activity), a complement-dependent cytotoxicity (CDC activity), an antibody-dependent phagocytosis (ADP activity) by phagocytic cells such as macrophages or dendritic cells, and the like are known.

In addition, by controlling a content of core fucose of a complex type N-linked sugar chain of Fc region of a monoclonal antibody which is produce by the method of the present invention, an effector activity of the antibody can be increased or decreased.

As a method for lowering a content of fucose which is bound to a complex type N-linked sugar chain bound to Fc region of the antibody, an antibody to which fucose is not bound can be obtained by the expression of an antibody using a CHO cell which is deficient in a gene encoding α1,6-fucosyltransferase. The antibody to which fucose is not bound has a high ADCC activity.

On the other hand, as a method for increasing a content of fucose which is bound to a complex type N-linked sugar chain bound to Fc of an antibody, an antibody to which fucose is bound can be obtained by the expression of an antibody using a host cell into which a gene encoding α1,6-fucosyltransferase is introduced. The antibody to which fucose is bound has a lower ADCC activity than the antibody to which fucose is not bound.

Further, by modifying amino acid residue(s) in an Fc region of an antibody, the ADCC activity or CDC activity can be increased or decreased. For example, the CDC activity of an antibody can be increased by using the amino acid sequence of the Fc region of the antibody described in US2007/0148165.

Further, the ADCC activity or CDC activity of an antibody can be increased or decreased by carrying out amino acid modification described in U.S. Pat. No. 6,737,056, or 7,297,775 or 7,317,091.

The term "suspension mammalian cell" in the present invention means a cell which does not adhere to a cell culture anchorage coated for facilitating adhesion of culture cells, such as microbeads, a culture container for tissue culture (also referred to as a tissue culture or adhesion culture container and the like) and the like, and can survive and grow while suspending in the culture solution.

As long as the cell does not adhere to the cell culture anchorage, the cell may survive and grow in a state of a single cell in the culture solution or survive and grow in a state of a mass of cells formed by the agglutination of two or more cells.

In addition, as the suspension mammalian cell to be used in the present invention, a cell which can survive and grow in a serum-free medium that does not contain fetal calf serum (hereinafter referred to as FCS) and the like, while suspending in the culture solution without adhering to the cell culture anchorage, is preferable, and a mammalian cell which can survive and grow while suspending in a protein-free medium that does not contain protein is more preferable.

The culture container for tissue culture may be any one such as a flask, a Petri dish and the like as long as it is coated for adhesion culture is applied thereto. Particularly, for example, whether or not it is a suspension mammalian cell can be confirmed using commercially available tissue culture flask (manufactured by Greiner), adhesion culture flask (manufactured by Sumitomo Bakelite) and the like.

As the suspension mammalian cell to be used in the present invention, it may be either a cell prepared by further adapting a cell originally having a suspension property to suspension culture or a suspension mammalian cell prepared by adapting an adhesive mammalian cell to suspension culture conditions.

Examples of the cell originally having a suspension property include PER.C6 cell, a rat myeloma cell YB2/3HL.P2.G11.16Ag.20 (or also called YB2/0), CHO-S cell (manufactured by Invitrogen) and the like.

The above "suspension mammalian cell prepared by adapting an adhesive mammalian cell to suspension culture conditions" can be prepared by the method described in *Mol. Biotechnol.*, 2000, 15(3), 249-57 or by the method shown in the following, and can be prepared by establishing a cell which shows proliferation property and surviving property similar to those before adapting the suspension culture or superior to those before adapting to suspension culture (*J. Biotechnol.*, 2007, 130(3), 282-90).

The term "similar to those before the suspension culture adaptation" means that survival ratio, proliferation rate (doubling time) and the like of the cell adapted to the suspension culture are substantially the same as those of the cell before adapting suspension culture.

In the present invention, examples of the method for adapting an adhesive mammalian cell to suspension culture conditions include the following method. The serum content of a serum-containing medium is reduced to $1/10$ and sub-culturing is repeated at relatively high concentration of cell. When the mammalian cell comes to be able to survive and proliferate, the serum content is further reduced and the sub-culturing is repeated. By this method, a suspension mammalian cell which can survive and proliferate under serum-free conditions can be prepared.

In addition, a suspension mammalian cell can also be prepared by a method comprising culturing with the addition of an appropriate nonionic surfactant such as Pluronic-F68 or the like in the culture solution.

Examples of the adhesive mammalian cell which acquires suspension property by adapting to a suspension culture condition include a mouse myeloma cell NS0, a CHO cell and the like.

In the present invention, as a property possessed by the suspension mammalian cell, suspension culturing is carried out under the condition of $2\times10^5$ cells/ml, and then the cell concentration after culturing for 3 or 4 days is preferably $5\times10^5$ cells/ml or more, more preferably $8\times10^5$ cells/ml or more, particularly preferably $1\times10^6$ cells/ml or more, most preferably $1.5\times10^6$ cells/ml or more.

In addition, doubling time of the suspension mammalian cell of the present invention is preferably 48 hours or less, more preferably 24 hours or less, particularly preferably 18 hours or less, most preferably 11 hours or less.

Examples of the medium for suspension culturing include commercially available medium, such as CD-CHO medium (Invitrogen), EX-CELL 325-PF medium (SAFC Biosciences), SFM4-CHO medium (HyClone) and the like. In addition, it can also be obtained by mixing saccharides, amino acids and the like which are necessary for the culturing of mammalian cells.

The suspension mammalian cell can be cultured using a culture container which can be used for suspension culturing under a culture condition capable of suspension culturing. Examples of the culture container include a 96-well plate for suspension cell culture (manufactured by Corning), a T-flask (manufactured by Becton Dickinson), a conical flask (manufactured by Corning) and the like.

Regarding the culture conditions, for example, it can be statically cultured in an atmosphere of 5% $CO_2$ at a culture temperature of 37° C. A shaking culture equipment, such as culturing equipment for suspension culture exclusive use, e.g., Wave Bioreactor (manufactured by GE Healthcare Bioscience), can be also used.

Regarding the suspension culture conditions for a suspension mammalian cell using the Wave Bioreactor equipment, the cell can be cultured by the method described on the GE Healthcare Bioscience homepage www.gelifesciences.co.jp/tech_support/manual/pdf/cellcult/wave_03_16.pdf.

In addition to the shaking culture, culturing by a rotation agitation equipment such as a bioreactor, can also be used. Culturing using a bioreactor can be carried out by the method described in *Cytotechnology*, (2006) 52: 199-207, and the like.

In the present invention, when a cell line other than the suspension mammalian cells is used, any cell line can be used so long as it is a mammalian cell line adapted to the suspension culture by the above-mentioned method and is a cell line which can be used in the protein production method of the present invention.

Purification of the protein of interest produced by the suspension mammalian cell is carried out by separating the protein of interest from impurities other than the protein of interest in a culture solution or cell homogenate containing the protein of interest. Examples of the separation method include centrifugation, dialysis, ammonium sulfate precipitation, column chromatography, a filtering and the like. The separation can be carried out based on the difference in physicochemical properties of the protein of interest and impurities or the difference in their avidity for the column carrier itself.

As the method for purifying the protein of interest, the purification is carried out by the method described in *Protein Experimentation Note* (the first volume)—*Extraction, Separation and Expression of Recombinant Protein* (translation of a textbook written in Japanese) (edited by Masato Okada and Kaori Miyazaki, published by Yodo-sha, ISBN 9784897069180) and the like.

The entire contents of the references, such as the scientific documents, patents, patent applications cited herein are incorporated herein by reference to the same degree of those illustratively described, respectively.

By the method for producing the protein of the present invention, a protein of interest can be efficiently produced using a suspension mammalian cell. The cell of the present invention can be used as a protein producing cell for producing a recombinant protein.

The present invention has been described in the above by showing preferred embodiments thereof for the sake of easy understanding. Hereinafter, the present invention is further described specifically based on examples, but the above-mentioned explanations and the following examples are provided merely for the purpose of exemplifications and not provided for the purpose of limiting the invention. Accordingly, the scope of the invention is not limited to the embodiments and examples which are specifically described in the present specification, but is limited by the claims alone.

Various experimental techniques relating to recombination described in the followings, such as the cloning and the like were carried out in accordance with the genetic engineering techniques described in *Molecular Cloning 2$^{nd}$ edition* edited by J. Sambrook, E. F. Frisch and T. Maniatis, *Current Protocols in Molecular Biology* edited by Frederick M. Ausubel et al, published by Current Protocols, and the like.

EXAMPLES

Example 1

Preparation of Transposon Vector for Expressing Anti-Human Influenza M2 Antibody A plasmid which comprises a gene expression cassette for mammalian cells comprising an arbitrary human antibody gene and a drug resistance marker gene inserted between a pair of Tol2 transposon sequences was used as a plasmid vector for protein expression.

Each DNA of the used genes was chemically and artificially synthesized based on a known nucleotide sequence or obtained by preparing primers for its both terminal sequences and then carrying out PCR using an appropriate DNA source as a template. In order to carry out the gene manipulation later, a restriction site for a restriction enzyme was added to the terminal of the primer.

In the nucleotide sequence (SEQ ID NO:1) of the non-autonomous Tol2 transposon disclosed by Japanese Published Unexamined Patent Application No. 235575/2003, the nucleotide sequence at position 1 to 200 (Tol2-L sequence) (SEQ ID NO:2) and the nucleotide sequence at positions 2285 to 2788 (Tol2-R sequence) (SEQ ID NO:3) were used as the transposon sequences.

Each synthetic DNA fragments comprising a pair of transposon sequences (manufactured by TAKARA BIO INC.) was prepared by the following method. A DNA fragment comprising a nucleotide sequence in which a recognition sequence of a restriction enzyme NruI was attached to both of the 5'-terminal and 3'-terminal of the Tol2-R sequence was prepared. Then, a DNA fragment comprising a nucleotide sequence in which a recognition sequence of a restriction enzyme FseI was attached to the 5'-terminal of the Tol2-L sequence and a restriction enzyme AscI was attached to the 3'-terminal thereof was prepared.

Next, the thus prepared DNA fragments comprising Tol2-R sequence and Tol2-L sequence were inserted into an expression vector N5LG1_M2_Z3 vector (WO2006/061723) comprising a nucleotide sequence encoding an amino acid sequence of anti-human influenza M2 antibody Z3G1.

The N5LG1_M2_Z3 vector (WO2006/061723) into which a nucleotide sequence (SEQ ID NO:9) encoding the H chain (SEQ ID NO:10) and a nucleotide sequence (SEQ ID NO:11) encoding the L chain (SEQ ID NO:12) of the anti-human influenza M2 antibody Z3G1 (ATCC Deposit No. PTA-5968: deposited Mar. 13, 2004, American Type Culture Collection, Manassas, Va., USA) were inserted under the control of the CMV enhancer/promoter control was used as an antibody gene expression cassette.

The DNA fragment comprising the Tol2-R sequence was inserted into the restriction enzyme NruI site positioned at the 5'-terminal side of a gene fragment comprising the antibody gene expression cassette and a selectable marker gene on the N5LG1_M2_Z3 vector. Then, the DNA fragment comprising the Tol2-L sequence was inserted into the restriction enzyme FseI and AscI sites positioned at the 3'-terminal side.

In addition, a transposon vector for expressing an anti-human influenza M2 antibody was constructed (FIG. 1) by inserting a cycloheximide resistance gene expression cassette in which a nucleotide sequence (SEQ ID NO:5) encoding a resistance gene for cycloheximide (a gene in which proline at position 54 of the human ribosomal protein L36a was substituted with glutamine) is connected under the control of the CMV enhancer/promoter into the FseI recognition site of the N5LG1_M2_Z3 vector connected with the Tol2 transposon sequence.

Figure 2:
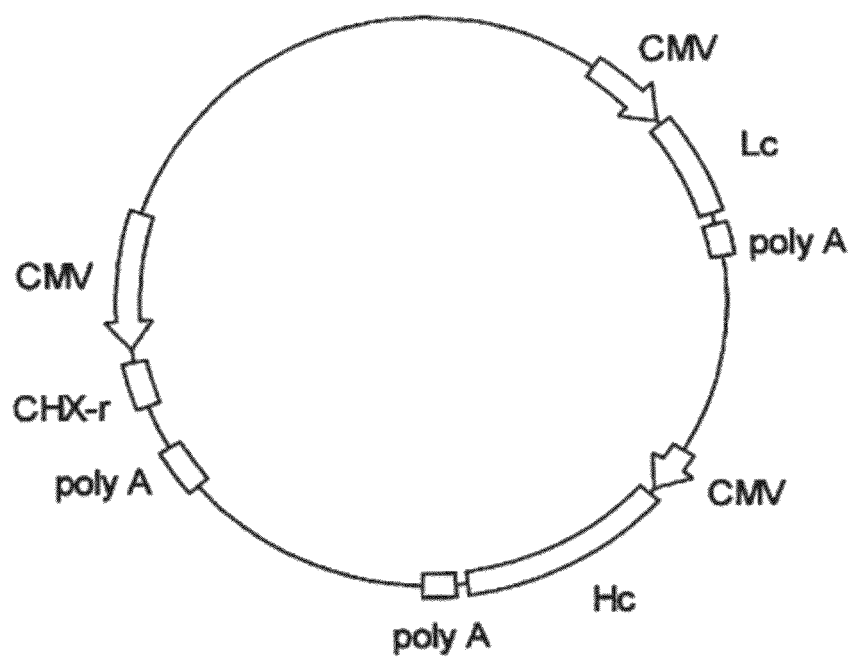
FIG. 2 shows a schematic illustration of an anti-human influenza M2 antibody expression vector. CMV represents a CMV promoter, poly A represents a polyadenylation site, Hc represents a human antibody H chain cDNA, Lc represents a human antibody L chain cDNA and CHX-r represents a cycloheximide resistance gene.

On the other hand, a vector comprising no transposon sequences was named anti-human influenza M2 antibody expression vector and used as the control vector (FIG. 2).

Example 2

Preparation of Transposase Expression Vector

Figure 3:
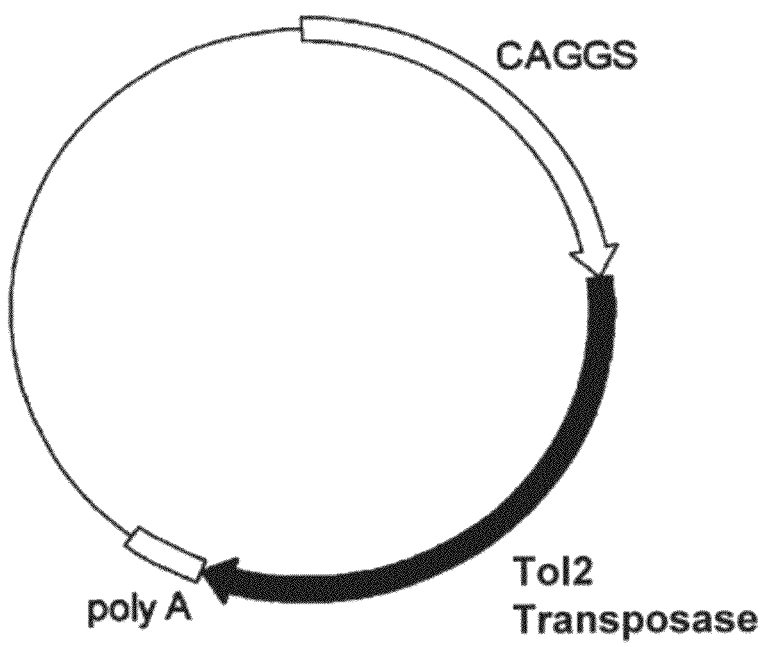
FIG. 3 shows a schematic illustration of a Tol2 transposase expression vector. CAGGS represents a CAGGS promoter, poly A represents a polyadenylation site, and TPase cDNA represents a Tol2 transposase cDNA.

The transposase was expressed using an expression vector independent of the expression vector of the antibody of interest. That is, a gene which is encoding a medaka fish-derived Tol2 transposase (SEQ ID NO:4) was inserted into a downstream of the CAGGS promoter of a pCAGGS vector (*Gene*, 108, 193-200, 1991) to prepare a Tol2 transposase expression vector (hereinafter referred to as Tol2 vector) (FIG. 3).

Example 3

Preparation of Transformant Using Mammal Animal Cell (1) Preparation of Suspension CHO Cell An adhesive CHO cell which had been cultured using α-MEM medium (Invitrogen) containing 10% serum (FCS) was peeled off by a trypsin treatment and then recovered, followed by shaking culture at 37° C. in a 5% $CO_2$ incubator using the fresh the α-MEM medium containing 10% FCS. Several days thereafter, growth of these cells was confirmed and then shaking culture was carried out by inoculating them into a α-MEM medium containing 5% FCS at a concentration of $2\times10^5$ cells/ml followed by shaking culture.

Further several days thereafter, the inoculation was similarly carried out using the α-MEM medium containing 5% FCS. Finally, a cell adapted to the suspension culture was prepared by repeating the sub-culture and shaking culture using the serum-free α-MEM medium and confirming that the cells have the same growing ability as the case of their culturing in the presence of serum.

(2) Preparation of CHO Cell which Produces Antibody

As the expression vector, the transposon vector for expressing the anti-human influenza M2 antibody prepared in Example 1 and Example 2 (hereinafter referred to as a transposon vector) and Tol2 vector pCAGGS-T2TP (FIG. 3, Kawakami K. & Noda T., *Genetics*, 166, 895-899 (2004)) were used. In addition, the anti-human influenza M2 antibody expression vector having no transposon sequences was used as the control.

By introducing the above expression vectors into the suspension culture-adapted CHO-K1 cell (American Type Culture Collection Cat. No. CCL-61) or HEK293 cell (Invitrogen, FreeStyle 293F cell), the frequencies of obtaining cycloheximide-resistant clones were compared.

Each cells ($4\times10^6$ cells) was suspended in 400 µl of PBS, and the transposon vector for expressing the anti-human influenza M2 antibody (10 µg) and Tol2 vector (25 µg) were co-transfected directly in the form of circular DNA by electroporation. In this connection, in order to express the Tol2 transposase transiently, the Tol2 vector was directly introduced in the form of circular DNA for the purpose of preventing from integrating into the host chromosome.

In addition, as the control, the anti-human influenza M2 antibody expression vector (10 µg) was linearized by a restriction enzyme and then introduced into each cells, in accordance with the standard gene introduction method by electroporation.

The electroporation was carried out using a cuvette of 4 mm in gap width (manufactured by Bio-Rad), using an electroporator (Gene Pulser Xcell System (manufactured by Bio-Rad)) under conditions of 300 V in voltage, 500 µF in electrostatic capacity and room temperature.

After the gene introduction by electroporation, each cell was seeded into three 96-well plates and cultured in a $CO_2$ incubator for 3 days using the EX-CELL 325-PF medium manufactured by SAFC Biosciences for the CHO cell, and the FreeStyle-293 medium (manufactured by Invitrogen) for the HEK293 cell.

Next, from the day of medium exchange on the 4th day of the gene introduction, 3 µg/ml of cycloheximide was added to the medium so that the cells were cultured in the presence of cycloheximide, followed by culturing for 3 weeks while carrying out the medium exchange in every week.

After culturing for 3 weeks, the number of wells in which cycloheximide-resistant colonies were found was counted. The results are shown in Table 1 and Table 2.

TABLE 1

Comparison of the numbers of cycloheximide-resistant cells (CHO cell)

|  | Transposon vector | Conventional vector |
|---|---|---|
| Test 1 | 155/288 | 0/288 |
| Test 2 | 100/288 | 0/288 |
| Test 3 | 94/288 | 0/288 |

TABLE 2

Comparison of the numbers of cycloheximide-resistant cells (NEK293 cell)

|  | Transposon vector | Conventional vector |
|---|---|---|
| Test 1 | 0/288 | 0/288 |
| Test 2 | 0/288 | 0/288 |
| Test 3 | 0/288 | 0/288 |

As shown in Table 1, each the anti-human influenza M2 antibody expression transposon vector or anti-human influenza M2 antibody expression vector was introduced into the suspension CHO-K1 cell. As a result, cycloheximide-resistant transformants were not obtained from the cells into which the anti-human influenza M2 antibody expression vector was introduced as in the other cell lines, but cycloheximide-resistant transformants were obtained from the cell into which the transposon vector for expressing anti-human influenza M2 antibody was introduced with a high frequency.

On the other hand, as shown in Table 2, cycloheximide-resistant transformants were not obtained when either of the transposon vector for expressing anti-human influenza M2 antibody and anti-human influenza M2 antibody expression vector was introduced into the HEK293 cells.

Based on these results, it was found that the gene encoding a protein of interest and cycloheximide resistance gene which were inserted between a pair of transposon sequences were efficiently introduced into the chromosome of the host cell in the suspension mammalian cell.

(3) Examination on the Antibody Production in Suspension CHO Cell and Adhesive CHO Cell In order to examine antibody production efficiency in a suspension CHO cell or an adhesive CHO cell, the amounts of antibodies produced by each cell line were examined. As the suspension CHO cell, a suspension CHO-K1 cell adapted to suspension culture was used. In addition, as the adhesive CHO cell, an adhesive CHO-K1 cell before adaptation to suspension culture was used.

The anti-human influenza M2 antibody expression transposon vector (10 µg) and Tol2 vector (25 µg) were introduced into the suspension CHO-K1 cell and the adhesive CHO-K1 cell by electroporation, respectively. Thereafter, the suspension CHO-K1 cell and the adhesive CHO-K1 cell were inoculated into three 96-well plates for each cell.

A medium for suspension cells (EX-CELL 325-PF, manufactured by SAFC Biosciences) was used for the suspension CHO-K1 cell, and the α-MEM medium containing 10% serum was used for the adhesive CHO-K1 cell. Each cell was cultured in a $CO_2$ incubator for 3 days. From the day of medium exchange of the 4th day of the electroporation, 3 µg/ml of cycloheximide was added to the medium so that the cells were cultured in the presence of cycloheximide and the cells were further cultured for 3 weeks. In this case, the medium exchange was carried out every week.

For the suspension CHO-K1 cell, $1\times10^6$ of the cells were seeded into a 6-well plate, followed by shaking-culture in a $CO_2$ incubator for 3 days, and the amount of the antibody protein was measured by HPLC using the culture supernatant.

For the adhesive CHO-K1 cell, medium exchange was carried out when the cell reached confluent on a 6-well plate ($2\times10^6$ cells), and after static culturing for 3 days, the amount of the antibody protein was measured by HPLC using the culture supernatant.

Figure 4:
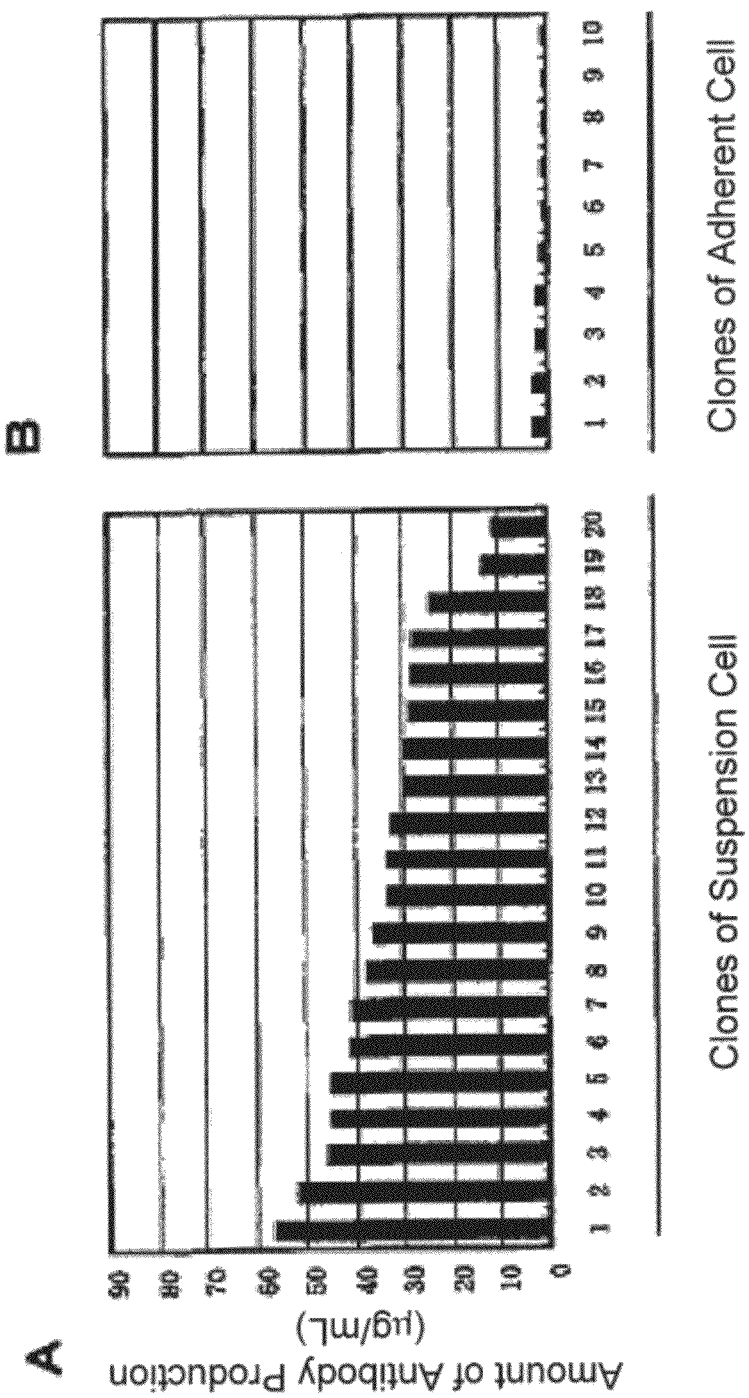
FIG. 4 shows a result of examining expression level of an anti-human influenza M2 antibody in a suspension CHO-K1 cell and an adhesive CHO-K1 cell when a Tol2 transposon vector for expressing an anti-human influenza M2 antibody was used.

The antibody concentration in the culture supernatant was measured in accordance with the method described in *Yeast Res.*, 7 (2007), 1307-1316. The results are shown in FIG. 4.

As shown in FIG. 4A, a large number of cells showing a markedly high antibody expression level were obtained when the CHO-K1 cell adapted to suspension culture was used. On the other hand, as shown in FIG. 4B, only the cells showing an expression level of the HPLC detection limit (5 µg/ml) or less were obtained when the adhesive CHO-K1 cell was used.

Based on these results, it was found that, in order to express a protein of interest using a transposon vector, the protein of interest could be expressed at a high level when a suspension mammalian cell is used.

In addition, it was found from the results of Examples 1 to 3 that the method of the invention could be used as a novel method for producing a protein of interest, by efficiently preparing a production cell which can highly express an exogenous gene using a suspension mammalian cell adapted to suspension culture.

Example 4

Preparation of Antibody Expression Cell Using Tol1 Transposon and Antibody Preparation (1)

Preparation of Tol1 Transposon Vector for Expressing Anti-Human Influenza M2 Antibody In the same manner as in Example 1, a plasmid which comprised a gene expression cassette for mammalian cells, comprising an arbitrary human antibody gene and a drug resistance marker gene inserted between a pair of Tol1 transposon sequences, was used as a protein expression plasmid vector.

Each DNA of the used genes was chemically synthesized in the artificial way based on the known sequence information or obtained by preparing primers of its both terminal sequences and carrying out PCR using an appropriate DNA source as the template. For the gene manipulation to be carried out later, a restriction enzyme digestion site was added to the end of the primer.

In the nucleotide sequence of the non-autonomous Tol1 transposon represented by SEQ ID NO:13 in Sequence Listing (WO2008/072540), the nucleotide sequence at positions 1 to 200 (Tol1-L sequence) (SEQ ID NO:14) and the nucleotide sequence at positions 1351 to 1855 (Tol1-R sequence) (SEQ ID NO:15) were used as the transposon sequences.

Each of the synthetic DNA fragments comprising each a pair of transposon sequences was prepared by the following method. A DNA fragment comprising a nucleotide sequence in which a recognition sequence of a restriction enzyme NruI was connected to both of the 5'-terminal and 3'-terminal of the Tol1-R sequence. Then, a DNA fragment comprising a nucleotide sequence in which a recognition sequence of a restriction enzyme FseI was connected to the 5'-terminal of the Tol1-L sequence and a restriction enzyme AscI was connected to the 3'-terminal thereof.

Next, the thus prepared DNA fragments comprising Tol1-R sequence and Tol1-L sequence were inserted into the expression vector N5LG1_M2_Z3 vector. The DNA fragment comprising the Tol1-R sequence was inserted into the restriction enzyme NruI site, existing on the 5'-terminal side of a gene fragment comprising the antibody gene expression cassette and a selectable marker gene on the N5LG1_M2_Z3 vector, and the DNA fragment comprising the Tol1-L sequence was inserted into the restriction enzyme FseI and AscI sites existing on the 3'-terminal side.

Figure 5:
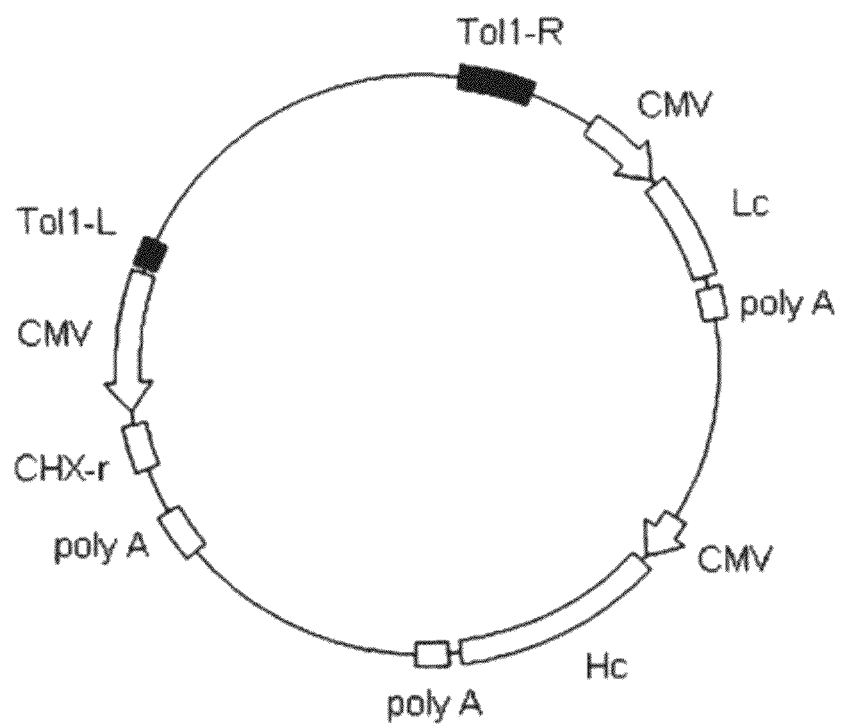
FIG. 5 shows a schematic illustration of a Tol1 transposon vector for expressing an anti-human influenza M2 antibody. Tol1-L represents a left end Tol1 transposon (SEQ ID NO:14), Tol1-R represents a right end Tol1 transposon (SEQ ID NO:15), CMV represents a CMV promoter, poly A represents a polyadenylation site, Hc represents a human antibody H chain cDNA, Lc represents a human antibody L chain cDNA, and CHX-r represents a cycloheximide resistance gene.

In addition, Tol1 transposon vector for expressing an anti-human influenza M2 antibody was constructed (FIG. 5) by inserting a cycloheximide resistance gene expression cassette in which a resistance gene for cycloheximide (a gene in which proline at position 54 in the human ribosomal protein L36a was mutated to glutamine) is connected under the control of the CMV enhancer/promoter into the FseI recognition site of the N5LG1_M2_Z3 vector connected with the Tol1 transposon sequence.

(2) Preparation of Tol1 Transposase Expression Vector

Figure 6:
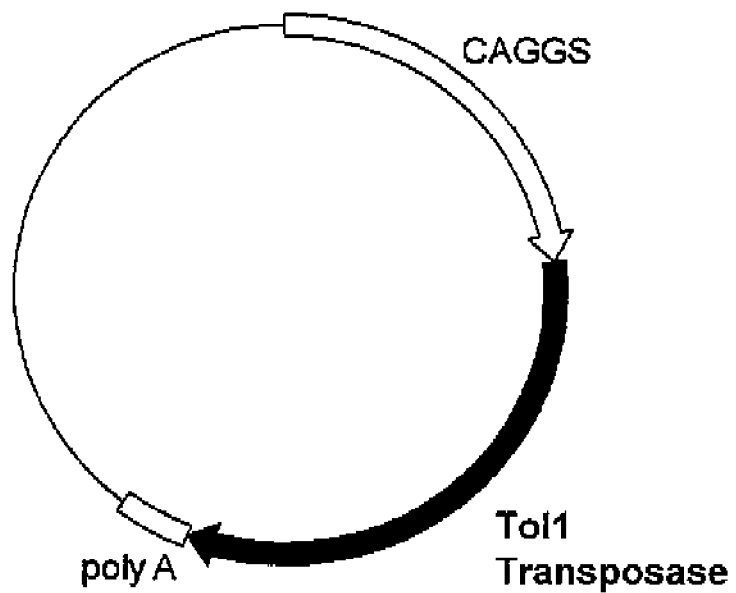
FIG. 6 shows a schematic illustration of a Tol1 transposase expression vector. CAGGS represents a CAGGS promoter, poly A represents a polyadenylation site, and TPase cDNA represents a Tol1 transposase cDNA.

The transposase was expressed using an expression vector independent from the expression vector of the antibody of interest. That is, a Tol1 transposase gene expression cassette in which a DNA fragment encoding a medaka fish-derived Tol1 transposase (SEQ ID NO:17) comprised of the nucleotide sequence represented by SEQ ID NO:16 was connected under the CMV enhancer/promoter control was inserted into pBluescriptII SK (+) (manufactured by Stratagene) and used as the Tol1 transposase expression vector pTol1ase (FIG. 6).

(3) Preparation of CHO Cell which Produces Antibody

Using the expression vectors prepared in the above (1) to (3), the introduction efficiency of the expression vector by Tol1 transposon was examined in the same manner as Example 3. The result was shown in Table 3.

TABLE 3

|  | Tol1 transposon vector |
|---|---|
| Tests 1 | 133/192 |
| Tests 2 | 67/192 |
| Tests 3 | 122/192 |

As shown in Table 3, when the Tol1 transposon vector for expressing the anti-human influenza M2 antibody was introduced into the suspension CHO-K1 cell, cycloheximide-resistant transformants were obtained at a high frequency as in the case with Example 3 in which the Tol2 transposon vector for expressing the anti-human influenza M2 antibody was introduced.

It was found based on these results that the antibody gene and cycloheximide resistance gene inserted between a pair of transposon sequences are efficiently transduced into the chromosome of the host cell, namely the suspension mammalian cell, in the case of using the Tol1 transposon, too.

(4) Examination on Antibody Production by Suspension CHO Cell

Antibody production efficiency of the suspension CHO cell was examined using the Tol1 transposon in the same manner as Example 3(3).

The antibody concentration in culture supernatant was measured in accordance with the method described in *FEMS Yeast Res.*, 7 (2007), 1307-1316. The results are shown in FIG. 7.

Figure 7:
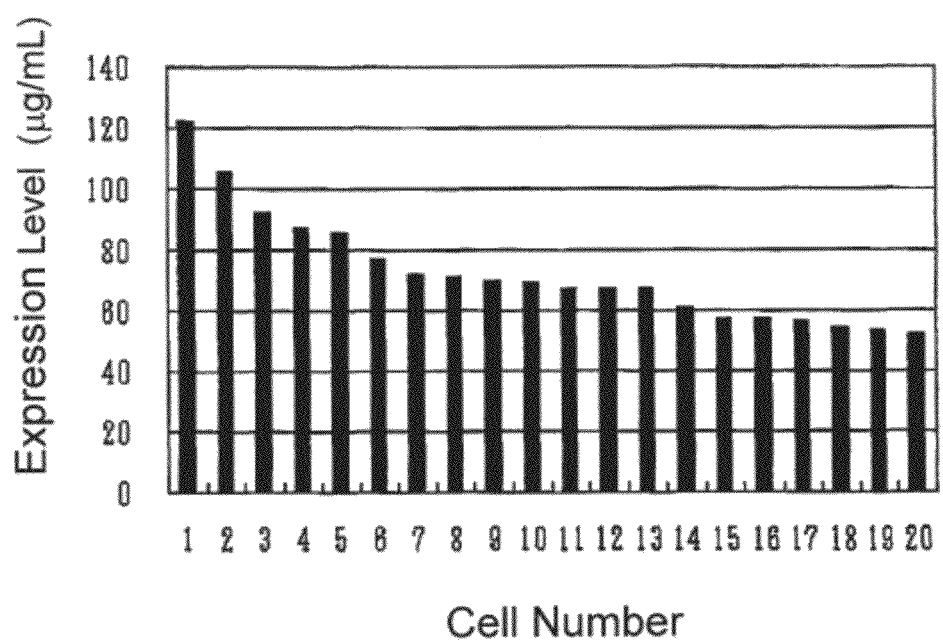
FIG. 7 shows a result of examining expression level of an anti-human influenza M2 antibody in a suspension CHO-K1 cell when a Tol1 transposon vector for expressing an anti-human influenza M2 antibody was used. The ordinate shows the amount of antibody production (μg/ml), and the abscissa shows the number of transgenic clones of each cell.

As shown in FIG. 7, a large number of cells showing a markedly high antibody expression level were also obtained in the case using the Tol1 transposon. From this result, it was found that similar to the case using the nucleotide sequence derived from Tol2 transposon, a suspension mammalian cell capable of highly expressing the protein of interest could also be obtained when a nucleotide sequence derived from Tol1 transposon is used as the transposon sequence.

Example 5

Preparation of Anti-Human CD98 Antibody (1) Preparation of Anti-Human CD98 Antibody Heavy Chain Expression Transposon Vector and Anti-Human CD98 Antibody Light Chain Expression Transposon Vector In order to prepare an anti-human CD98 antibody having the variable region H chain and L chain represented by the amino acid sequences of SEQ ID NOs:20 and 23, respectively, amino acid sequences of the H chain and L chain were prepared by connecting amino acid sequence of human IgG1 antibody constant region to each antibody variable region.

Figure 8:
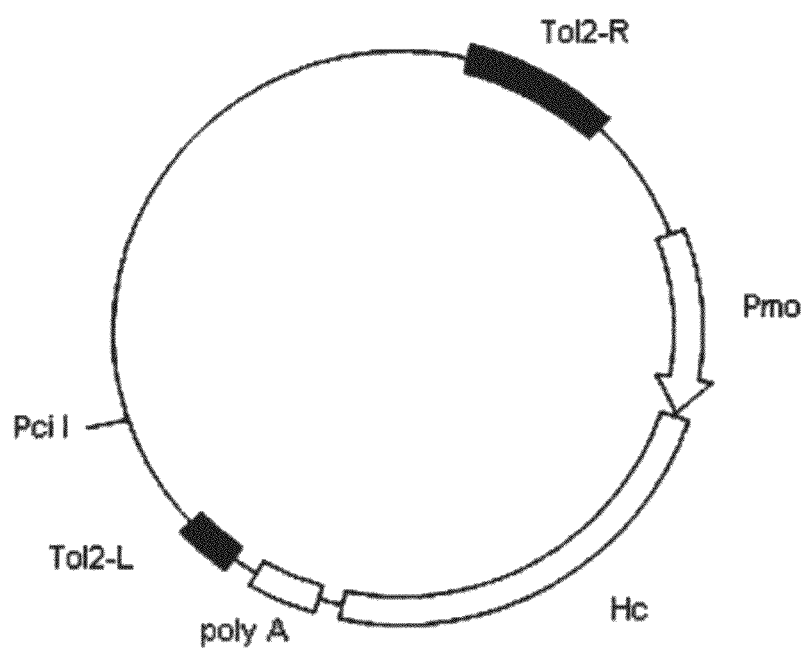
FIG. 8 shows a schematic illustration of a transposon vector for expressing an anti-human CD98 antibody heavy chain. Tol2-L represents a left end Tol2 transposon (SEQ ID NO:2), Tol2-R represents a right end Tol2 transposon (SEQ ID NO:3), Pmo represents a Moloney Murine Leukemia Virus promoter, poly A represents a polyadenylation site, and Hc represents an anti-human CD98 antibody heavy chain cDNA (SEQ ID NO:18).
Figure 9:
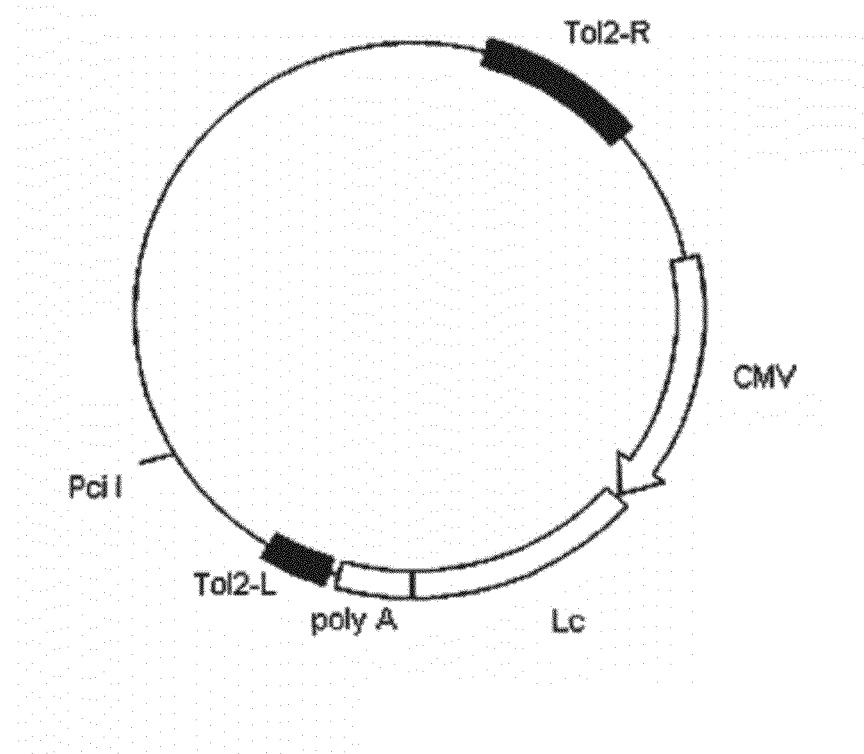
FIG. 9 shows a schematic illustration of a transposon vector for expressing anti-human CD98 antibody light chain. Tol2-L represents a left end Tol2 transposon (SEQ ID NO:2), Tol2-R represents a right end Tol2 transposon (SEQ ID NO:3), CMV represents a CMV promoter, poly A represents a polyadenylation site, and Lc represents an anti-human CD98 antibody light chain cDNA (SEQ ID NO:21).

Using the sequences integrated into a vector (N5KG1-Val C2IgG1NS/I117L) disclosed in Japanese Patent No. 4324637 as the gene sequences (SEQ ID Nos:18 and 21, respectively) of the anti-human CD98 antibody heavy chain variable region and light chain variable region to which a signal sequence had been connected, and using the transposon sequence, and promoter similar to those used in Example 1, an anti-human CD98 antibody heavy chain expression transposon vector (hereinafter, referred to as CD98H vector) and an anti-human CD98 antibody light chain expression transposon vector (hereinafter, referred to as CD98L vector) were respectively constructed (FIGS. 8 and 9).

The DNA fragment to be used was chemically synthesized in the artificial way based on the conventionally known sequence or obtained by preparing primers of its both terminal sequences and carrying out PCR using an appropriate DNA source as the template. A restriction enzyme digestion site was attached to a terminal of each primer for the sake of the later gene recombination operations.

(2) Preparation of Cycloheximide Resistance Gene Expression Transposon Vector

Figure 10:
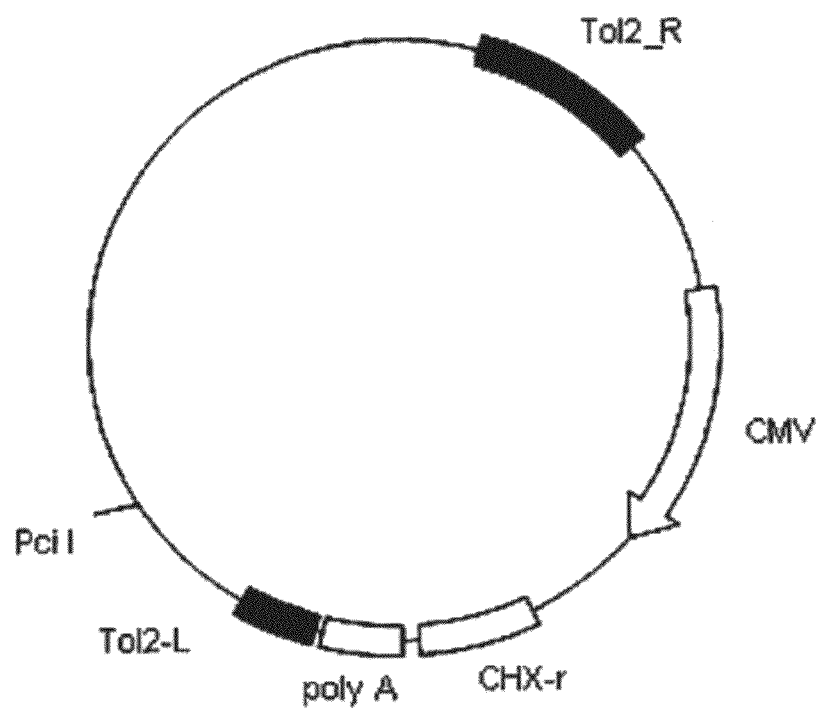
FIG. 10 shows a schematic illustration of a transposon vector for expressing a cycloheximide resistant gene. Tol2-L represents a left end Tol2 transposon (SEQ ID NO:2), Tol2-R represents a right end Tol2 transposon (SEQ ID NO:3), CMV represents a CMV promoter, poly A represents a polyadenylation site, and CHX-r represents a cycloheximide resistant gene (SEQ ID NO:7).

A cycloheximide resistance gene expression transposon vector (hereinafter, referred CHX vector) was constructed by connecting the sequence encoding a cycloheximide resistance gene (SEQ ID NO:7) under control of the CMV enhancer/promoter described in Example 1 and inserting a pair of transposon sequences (Tol-2L, Tol2-R) into both terminals of the cycloheximide resistance gene expression cassette (FIG. 10).

The DNA fragment to be used was artificially chemically synthesized based on the conventionally known sequence or obtained by preparing primers of its both terminal sequences and then carrying out PCR using an appropriate DNA source as the template. A restriction enzyme digestion site was attached to a terminal of each primer for the sake of the later gene recombination operations.

(3) Preparation of CHO Cell which Produces Anti-Human CD98 Antibody

The CD98H vector (FIG. 8), CD98L vector (FIG. 9) and CHX vector (FIG. 10) prepared in the above-mentioned (1) and (2) and the Tol2 vector (FIG. 3) prepared in Example 2 were introduced into CHO-K1 cell which was adapted to suspension culture, and the number of appeared cells capable of highly expressing the antibody was compared.

In the test plot, $4 \times 10^6$ cells of the CHO-K1 cell were suspended in 400 μl of PBS, and CD98H vector (10 μg), CD98L vector (10 μg), CHX vector (10 μg) and Tol2 vector (10 μg) were directly co-transfected in a form of circular DNA by electroporation. In order to express Tol2 transposase transiently and to prevent integration into the host chromosome, the Tol2 vector was introduced directly in the form of circular DNA. The electroporation was carried out using an electroporator (Gene Pulser Xcell system, manufactured by Bio-Rad) under conditions of voltage of 300 V, electrostatic capacity of 500 μF and room temperature and using a cuvette of 4 mm in gap width (manufactured by Bio-Rad).

Also, in the control plot, each of CD98H vector (10 μg), CD98L vector (10 μg) and CHX vector (10 μg) was linearlized using a restriction enzyme PciI (Takara Bio Inc.) and then electroporation was carried out in the same manner as the above.

After the gene introduction by electroporation, the cells in each cuvette were suspended in a CD OptiCHO medium supplemented with 0.5% soybean hydrolyzate (hereinafter, referred to as 0.5CD medium), inoculated onto one 96-well plate and cultured for 4 days in a $CO_2$ incubator. Next, from the medium exchange after 5 days of the gene introduction, culturing was carried out in the presence of cycloheximide using the 0.5CD medium supplemented with 3 μg/ml of cycloheximide (C4859, Sigma-Aldrich) followed by culturing for 4 weeks while carrying out the medium exchange at intervals of one week.

After 4 weeks of the culturing, expression of the antibody was determined by a sandwich method (LENCE™, Perkin-Elmer Corp) using FRET (fluorescence resonance energy transfer). Regarding the antibody high expression cells, clones expressing the antibody at a concentration in culture supernatant of 5.0 μg/ml or more were counted as the antibody-expressing cells, with the results shown in Table 4.

TABLE 4

| | Control plot | Test plot |
| --- | --- | --- |
| | The number of wells where the antibody is expressed | |
| Plate 1 | 10/96 | 29/96 |
| Plate 1 | 20/96 | 49/96 |

As shown in Table 4, large number of anti-human CD98 antibody expression cells were found in the test plot in which Tol2 vector was co-transfected into the suspension CHO-K1 cell together with anti-human CD98 heavy chain expression transposon vector, anti-human CD98 light chain expression transposon vector and cycloheximide resistance gene vector, but the anti-human CD98 antibody expression cells were not found in the control plot in which Tol2 vector was not co-transfected in spite of making the vectors into linear chains.

Example 6

Production of Anti-Human CD98 Antibody (1) Preparation of Expression Transposon Vector Comprising Anti-Human CD98 Antibody Heavy Chain Gene Fragment, Anti-Human CD98 Antibody Light Chain Gene Fragment and Cycloheximide Resistance Gene An expression transposon vector containing anti-human CD98 antibody heavy chain gene fragment, anti-human CD98 antibody light chain gene fragment and cycloheximide resistance gene (hereinafter, referred to as CD98-CHX tandem vector) was constructed using a synthetic DNA and a PCR method in the same manner as in the above by connecting the anti-human CD98 antibody heavy chain expression transposon vector prepared in Example 5(1) with the anti-human CD98 antibody light chain expression gene cassette prepared in Example 5(1) and the cycloheximide resistance gene cassette prepared in Example 5(2).

(2) Preparation of Expression Transposon Vector Comprising Anti-Human CD98 Antibody Heavy Chain Gene Fragment and Cycloheximide Resistance Gene An expression transposon vector comprising anti-human CD98 antibody heavy chain gene fragment and cycloheximide resistance gene (hereinafter, referred to as CD98H-CHX expression transposon vector) was constructed using a synthetic DNA and a PCR method in the same manner as in the above by connecting the anti-human CD98 antibody heavy chain expression transposon vector prepared in Example 5(1) with the cycloheximide resistance gene cassette prepared in Example 5(2).

(3) Preparation of CHO Cell Producing Anti-Human CD98 Antibody

Using the expression transposon vectors prepared in the above Example 5(1) and (2) and the above Example 6(1) and (2), the incidence of cells capable of highly expressing anti-CD98 antibody were compared on the case of gene-transferring H chain and L chain of anti-human CD98 antibody using the same expression vector (control plot), on the case of gene-transferring H chain or L chain of anti-human CD98 antibody or cycloheximide resistance gene respectively using different expression vectors (test plot 1) and on the case of gene-transferring H chain or L chain using different expression vectors (test plot 2).

In the test plot 1, $4 \times 10^6$ cells of the CHO-K1 cell were suspended in 400 μl of PBS, and CD98H vector (10 μg), CD98L vector (10 μg), CHX vector (10 μg) and Tol2 vector (10 μg) were directly co-transfected as circular DNA by electroporation.

In the test plot 2, $4 \times 10^6$ 6 cells of the CHO-K1 cell were suspended in 400 μl of PBS, and CD98H-CHX vector (10 μg), CD98L vector (10 μg) and Tol2 vector (10 μg) were directly co-transfected as circular DNA by electroporation.

In the control plot, $4 \times 10^6$ cells of the CHO-K1 cell were suspended in 400 μl of PBS, and CD98-CHX tandem vector (10 μg) and Tol2 vector (20 μg) were directly co-transfected as circular DNA by electroporation. Also, in all of the tests, in order to express Tol2 transposase transiently and to prevent integration into the host chromosome, the Tol2 vector was introduced directly in the form of circular DNA.

In the following method, the incidence of antibody producing cells was confirmed in the same manner as Example 5(3). Regarding the antibody producing cells, the clones in which the antibody concentration in culture supernatant was 3.0 μg/ml or more were counted as the antibody-expressing cells. The results are shown in Table 5.

TABLE 5

|  | Control plot | Test plot 1 | Test plot 2 |
| --- | --- | --- | --- |
|  | The number of wells where the antibody is expressed | | |
| Plate 1 | 18/96 | 82/96 | 95/96 |
| Plate 2 | 21/96 | 85/96 | 96/96 |
| Total | 39/192 | 167/192 | 191/192 |

In the test plot 1 in which CD98H vector, CD98L vector and CHX vector were introduced and the test plot 2 in which CD98H vector and CD98L vector were introduced, the incidence of the cells capable of highly expressing the anti-human CD98 antibody was markedly increased.

The above results show that cells having a high antibody productivity can be easily obtained and produced when different expression vectors in which the antibody heavy chain gene and antibody light chain gene are respectively inserted between transposon sequences are co-transfected into the suspension CHO cell, in comparison with a case in which an expression vector prepared by integrating the antibody heavy chain gene and antibody light chain gene into the same expression vector is introduced to the suspension CHO cell. In addition, it was revealed from the results of test plot 1 and test plot 2 that even when the vector to be introduced is two or more, at least one drug resistance gene (selectable marker gene) is enough. Further, it was revealed that the drug resistance gene may be present on an expression vector into which the antibody heavy chain gene is integrated or on a different independent vector.

The above results show that a transposon vector is effective as a means for efficiently introducing genes arranged on two or more vectors into a suspension of mammalian cells, which was conventionally difficult to achieve. Further, it is shown that for the purpose of achieving high productivity of a protein comprising more than one polypeptides or of more than one proteins, it is effective to introduce polypeptides and proteins using different transposon vectors.

(4) Culturing of CHO Cell which Produces Anti-Human CD98 Antibody

The top three cell lines having high antibody productivity were selected from each of the cells into which the CD98-CHX tandem vector obtained in the above-mentioned Example 6(3) was introduced and the cells into which the CD98H-CHX vector and CD98L vector were introduced, and their antibody expression levels were compared. Details of the tests are shown below.

The CHO-K1 cell obtained in Example 6(3) which was selected based on the cycloheximide resistance and also expresses the anti-CD98 antibody, was expansion-cultured using a 96-well plate, a 24-well plate and a 6-well plate (Corning Glassworks) in that order. After the expansion culturing, antibody concentration in each culture supernatant was measured, and the top three cell lines CHO cells having high level of anti-CD98 antibody expression were selected. Next, each of the thus selected three cell lines were suspended in 3 ml of 0.5% CD medium (Invitrogen), namely 0.5 CD medium, to a density of $2 \times 10^5$ cells/ml, and cultured on a shaker for 5 days in an atmosphere of 37° C. and 5% $CO_2$ using a 6-well plate. The amount of the antibody in the medium after 5 days of culturing was determined by HPLC (Waters Associates, Inc.). The results are shown in Table 6.

TABLE 6

|  | Cells derived from control plot | | | Cells derived from test plot 2 | | |
| --- | --- | --- | --- | --- | --- | --- |
| Expression level of antibody (mg/L) | 70 | 67 | 41 | 196 | 87 | 67 |

As shown in Table 6, the CHO-K1 cell into which CD98H vector and CD98L vector were co-transfected has a high antibody production level in comparison with the CHO-K1 cell into which CD98-CHX tandem vector was introduced.

The above results show that not only an antibody high producer cell line can be obtained and produced easily, but also the thus obtained cell has a high antibody productivity, when different expression vectors in which the antibody heavy chain gene and antibody light chain gene are respectively inserted between a pair of transposon sequences are co-transfected into the suspension CHO cell.

Example 7

Production of Anti-Human Tumor Necrosis Factor-Alpha (TNFα) Antibody (1) Preparation of Expression Transposon Vector Containing a TNFα Antibody Heavy Chain Gene Fragment, a TNFα Antibody Light Chain Gene Fragment and Cycloheximide Resistance Gene In order to prepare anti-human TNFα antibody having the amino acid sequence of SEQ ID NO:26 and SEQ ID NO:29, an anti-human TNFα antibody heavy chain gene fragment, an anti-human TNFα antibody light chain gene fragment and a cycloheximide resistance gene expression transposon vector (hereinafter, referred to as TNFα-CHX tandem vector) were constructed by replacing VH and VL gene fragments of the expression transposon vector comprising the anti-human CD98 heavy chain gene fragment and light chain gene fragment and cycloheximide resistance gene prepared in Example 6(1) (CD98-CHX tandem vector) by the anti-human TNFα antibody-derived VH and VL, respectively.

The sequences of anti-human TNFα antibody heavy chain gene and light chain gene were prepared using a synthetic DNA, by preparing amino acid sequences (SEQ ID NOs:26 and 29) in which a signal sequence was connected to the amino acid sequences (SEQ ID NOs:25 and 28) of the heavy chain variable region subunit or light chain variable region subunit of Adalimumab (recombinant) described in FIG. 1 and FIG. 2, respectively, of HUMIRA® subcutaneous injection 40 mg inspection report (Pharmaceutical and Medical Devices Agency, Feb. 14, 2008) and determining the nucleotide sequences in such a manner that the amino acid sequences did not change (SEQ ID NOs:24 and 27). For the sake of the latter gene manipulations, a restriction enzyme digestion site was added to the terminal of the artificial sequences.

(2) Preparation of Expression Transposon Vector Comprising Anti-Human TNFα Antibody Heavy Chain Fragment and Cycloheximide Resistance Gene An expression transposon vector containing anti-human TNFα antibody heavy chain fragment and cycloheximide resistance gene (hereinafter, referred to as TNFαH-CHX vector) was constructed by modifying a VH gene fragment region of the expression transposon vector containing anti-human CD98 antibody heavy chain fragment and cycloheximide resistance gene (CD98H-CHX vector) prepared in Example 6(2) to an anti-human TNFα antibody VH gene fragment. As the anti-human TNFα antibody heavy chain gene, a sequence of the same sequence shown in this item (1) was used.

(3) Preparation of Anti-Human TNFα Antibody Light Chain Gene Expression Transposon Vector An anti-human TNFα antibody light chain gene expression transposon vector (hereinafter, referred to as CD98L vector) was constructed by modifying the light chain gene region of the anti-human CD98 antibody light chain gene expression transposon vector prepared in Example 6(1) to anti-human TNFα antibody light chain. As the anti-human TNFα antibody VL gene, the same sequence as the sequence shown in this item (1) was used.

(4) Preparation of CHO Cell which Produces Anti-Human TNFα Antibody

In order to prepare CHO-K1 cell which produced anti-human TNFα antibody, the TNFα-CHX tandem vector (20 μg) prepared in the above-mentioned (1) and the Tol2 transposase expression vector (Tol2 vector) (10 μg) prepared in Example 2 were introduced into CHO-K1 cell adapted to suspension culturing prepared in Example 3 (control plot).

In the same manner, the TNFαH-CHX vector (10 μg), TNFα L vector (10 μg) and Tol2 vector (10 μg) prepared in the above-mentioned (2) and (3) were directly co-transfected in the form of circular DNA (test plot). The incidences of cells capable of highly expressing the antibody were compared by carrying out the gene introduction, cell culturing and the like in the same manner as in Example 6 except that culturing of the gene-introduced cells was carried out on five plates of the 96-well plate. Regarding the cell having a high antibody productivity, the clones in which the antibody concentration in culture supernatant was 3.0 μg/ml or more were counted as the antibody-expressing cells. The results are shown in Table 7.

TABLE 7

| | Control plot | Test plot |
|---|---|---|
| | The number of wells where the antibody is expressed | |
| Plate 1 | 20/96 | 83/96 |
| Plate 2 | 22/96 | 76/96 |
| Plate 3 | 21/96 | 82/96 |
| Plate 4 | 20/96 | 79/96 |
| Plate 5 | 27/96 | 81/96 |
| Total | 110/480 | 401/480 |

As shown in Table 7, as in the case of the anti-human CD98 antibody producing cell prepared in Example 6, the CHO-K1 cell into which TNFαH-CHX vector and TNFαL vector were co-transfected showed about 4 times higher incidence of cells in which the anti-human TNFα antibody was highly expressed, in comparison with the CHO-K1 cell into which TNFα-CHX tandem vector was introduced.

This result shows that, regarding any case of the antibody, a cell line having a high antibody productivity can be easily obtained and produced by co-transfecting the antibody heavy chain gene and the antibody light chain gene which are respectively inserted between a pair of transposon sequences introduced into different expression vectors, in the suspension CHO cell.

(5) Culturing of CHO Cell which Produces Anti-Human TNFα Antibody

Figure 11:
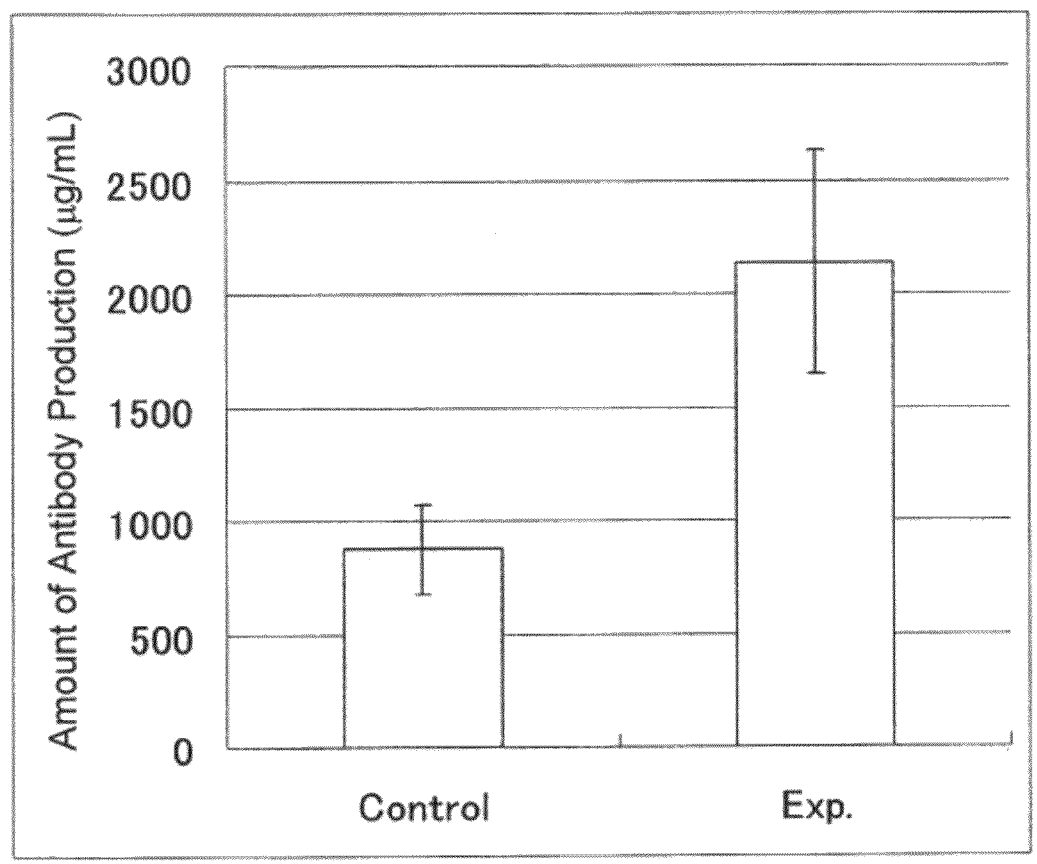
FIG. 11 shows production amount of anti-human TNFα antibody when TNFα-CHX tandem vector or TNFαH-CHX vector and TNFαL vector were gene-introduced into a CHO-K1 cell. The ordinate shows the concentration of the antibody (μg/ml) which is produced in the medium, the control plot is shown by Control, and the test plot is shown by Exp.

The cells which are selected based on the cycloheximide resistance from the TNFα-CHX tandem vector-introduced cells obtained in the above-mentioned (4) and the cells into which the TNFαH-CHX vector and TNFαL vector were co-transfected, and also expressing the anti-human TNFα antibody, were selected and expansion-cultured using 96-well plate, 24-well plate and 6-well plate in that order. Regarding 4 cell lines of the TNFα-CHX tandem vector-introduced cells succeeded in the expansion culturing and 52 cell lines into which the TNFαH-CHX vector and TNFαL vector were co-transfected, these cells were cultured in the same manner as in Example 6(4) except that the culturing period was 7 days, and the expression levels of the antibodies were measured. The results are shown in FIG. 11.

As a result, the CHO-K1 cell into which the TNFαH-CHX vector and TNFαL vector were co-transfected showed about 2.4 times higher antibody productivity than that of the CHO-K1 cell into which the TNFα-CHX tandem vector was introduced.

This result shows that, as in the case of Example 6(4), not only a cell having a high antibody productivity can be obtained and produced, but also the thus obtained cell has a high antibody productivity, when different expression vectors in which each of the antibody heavy chain gene and the antibody light chain gene are respectively inserted between a pair of transposon sequences are co-transfected into the suspension CHO cell.

Example 8

Production of Anti-Human CD20 Antibody

(1) Preparation of Expression Transposon Vector Comprising Anti-Human CD20 Antibody Heavy Chain Gene Fragment, Anti-Human CD20 Antibody Light Chain Gene Fragment and Cycloheximide Resistance Gene In order to prepare an anti-human CD20 antibody comprising VH and VL represented by the amino acid sequences of SEQ ID NOs:32 and 35, respectively, an expression transposon vector comprising an anti-human CD20 antibody heavy chain gene fragment, an anti-human CD20 antibody light chain gene fragment and a cycloheximide resistance gene (hereinafter, referred to as CD98-CHX tandem vector) was constructed by replacing antibody VH and VL gene regions of the CD98-CHX tandem vector prepared in Example 6(1) by the anti-human CD20 antibody-derived VH and VL, respectively.

The gene sequences of anti-human CD20 antibody VH region and VL region were prepared using a synthetic DNA, by preparing the nucleotide sequence described in GenBank accession No. AR000013 and amino acid sequences (SEQ ID NOs:31 and 34, respectively) in which a signal sequence was connected to the amino acid sequences (SEQ ID NOs:32 and 35, respectively) of the VH and VL of rituximab described in accompanying sheet of Rituxan® for injection 10 mg/ml inspection report (reported by National Institute of Health Sciences, No. 3395, Aug. 28, 2003) and determining the nucleotide sequences in such a manner that the amino acid sequences did not change (SEQ ID NOs:30 and 33). For the sake of the latter gene manipulations, a restriction enzyme digestion site was added to the terminal of the artificial sequences.

(2) Preparation of Expression Transposon Vector Comprising Anti-Human CD20 Antibody Heavy Chain Gene Fragment and Cycloheximide Resistance Gene An expression transposon vector comprising anti-human CD20 antibody heavy chain gene fragment and cycloheximide resistance gene (hereinafter, referred to as CD20H-CHX vector) was constructed by modifying the antibody VH gene region of the CD98H-CHX vector prepared in Example 6(2) to an anti-human CD20 antibody-derived VH. As the anti-human CD20 antibody heavy chain gene, the same sequence as a sequence shown in the above-mentioned (1) was used.

(3) Preparation of Anti-Human CD20 Antibody Light Chain Gene Expression Transposon Vector An anti-human CD20 antibody light chain gene expression transposon vector (hereinafter, referred to as CD20L vector) was constructed by modifying the VL gene regions of the anti-human CD98 antibody prepared in Example 6(1) to the anti-human CD20 antibody-derived VL. As the anti-human CD20 antibody heavy and light genes, the same sequences as a sequence shown in the above-mentioned (1) were used.

(4) Preparation of CHO Cell which Produces Anti-Human CD20 Antibody

In order to prepare CHO-K1 cell which produces anti-human CD20 antibody, the CD20-CHX tandem vector prepared in the above-mentioned (1) and the Tol2 transposase expression vector (Tol2 vector) prepared in Example 2 were introduced into CHO-K1 cell adapted to suspension culturing prepared in Example 3(1) (control plot).

In the same manner, the CD20H-CHX vector (10 μg) and CD20L vector (10 μg) prepared in the above-mentioned (2) and (3) were co-transfected into CHO-K1 cell together with Tol2 vector (10 μg) (test plot). The incidences of cells capable of highly expressing the antibody were compared by carrying out the gene introduction, cell culturing and the like in the same manner as Example 6 except that culturing of the gene-introduced cells was carried out on five plates of the 96-well plate. Also, antibody concentrations of 3.0 μg/ml or more were counted as the antibody-expressing wells. The results are shown in Table 8.

TABLE 8

| | Control plot | Test plot |
|---|---|---|
| | The number of wells where the antibody is expressed | |
| Plate 1 | 2/96 | 4/96 |
| Plate 2 | 2/96 | 9/96 |
| Plate 3 | 4/96 | 4/96 |
| Plate 4 | 1/96 | 8/96 |
| Plate 5 | 2/96 | 5/96 |
| Total | 11/480 | 30/480 |

As a result, the CHO-K1 cell into which the CD20H-CHX vector and CD20L vector were co-transfected showed about 3 times higher incidence of cells which highly expresses the anti-human CD20 antibody in comparison with the CHO-K1 cell into which the CD20-CHX tandem vector was introduced.

This result is similar to the result of the case of anti-human CD98 antibody and anti-human TNFα antibody carried out in Example 6(3) or Example 7(3) and shows that an antibody high level producer cell line can be easily obtained and produced regarding each case of the antibodies when different expression vectors in which each of the antibody heavy chain gene and the antibody light chain gene are respectively integrated between transposon sequences are co-transfected into the suspension CHO cell.

(5) Culturing of CHO Cell which Produces Anti-Human CD20 Antibody

The cells which are selected based on the cycloheximide resistance from the CD20-CHX tandem vector-introduced cells obtained in the above-mentioned (3) and the cells into which the CD20H-CHX vector and CD20L vector were co-transfected, and also expressing the anti-human CD20 antibody, were selected and expansion-cultured using 96-well plate, 24-well plate and 6-well plate in that order. Regarding 4 cell lines of the control plot cells succeeded in the expansion culturing and 50 cell lines of test plot cells, these cells were cultured in the same manner as in Example 6(4) except that the culturing period was 7 days, and their antibody expression levels were measured. The results are shown in FIG. 12.

Figure 12:
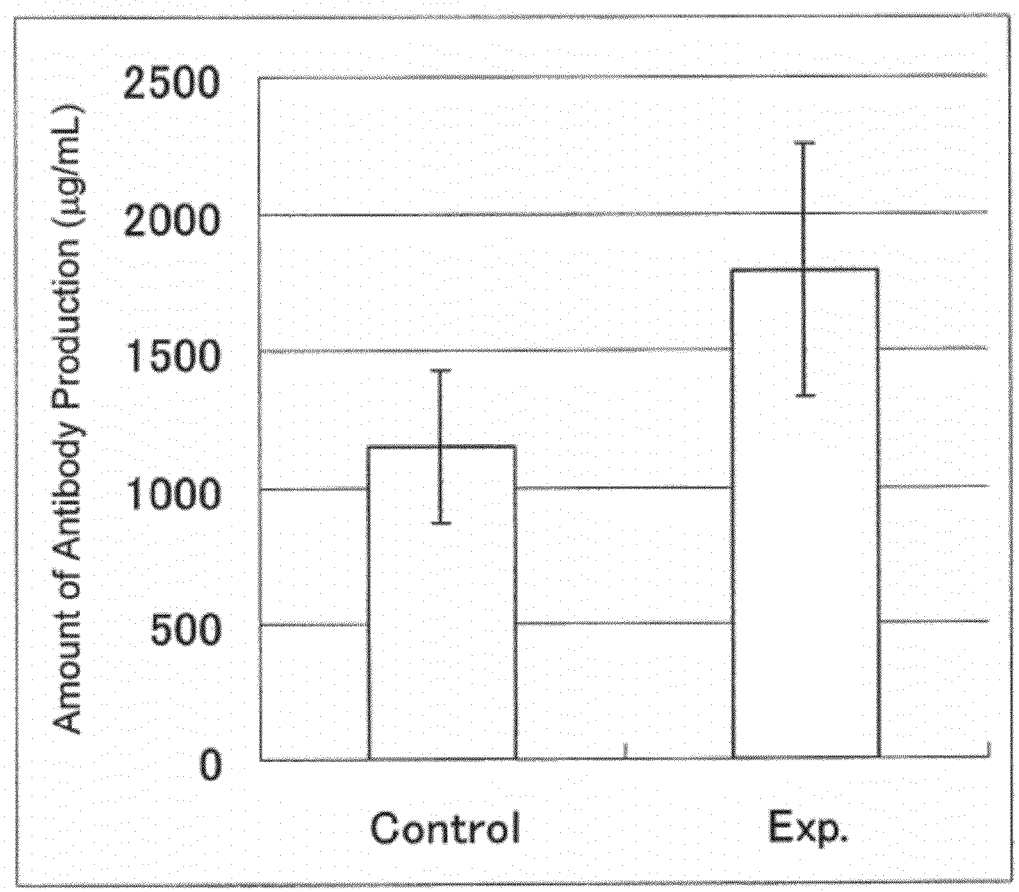
FIG. 12 shows production amount of anti-human CD20 antibody when CD20-CHX tandem vector or CD20H-CHX vector and CD20L vector were gene-introduced into a CHO-K1 cell. The ordinate shows the concentration of the antibody (μg/ml) which is produced in the medium, the control plot is shown by Control, and the test plot is shown by Exp.

As shown in FIG. 12, it was revealed that the CHO-K1 cell into which the CD20H-CHX vector and CD20L vector were co-transfected had about 1.6 times higher antibody productivity than the CHO-K1 cell into which the CD20-CHX tandem vector was introduced.

This result is similar to the result of the case of anti-human CD98 antibody and anti-human TNFα antibody carried out in Example 6(4) or Example 7(5) and shows that not only a cell line having a high antibody productivity can be easily obtained and produced when different expression vectors in which the antibody heavy chain gene and antibody light chain gene are respectively integrated between transposon sequences are co-transfected into the suspension CHO cell, but also the thus obtained cell has a high antibody productivity.

Example 9

Preparation of a Transposon Vector which Expresses Neomycin Resistance Gene and Anti-Human CD98 Antibody (1) Preparation of a Transposon Vector which Expresses Wild Type Neomycin Resistance Gene and Anti-Human CD98 Antibody A plasmid which comprised a gene expression cassette for mammalian cell use comprising an arbitrary human antibody gene and a drug resistance marker gene inserted between a pair of Tol2-derived nucleotide sequences was used as the plasmid vector for protein expression.

The DNA of the gene to be used was obtained by carrying out chemical synthesis in the artificial way based on a conventionally known nucleotide sequence or by preparing primers of its both terminal sequences and thereby carrying out PCR using an appropriate DNA source. For the sake of the latter gene manipulations, a restriction enzyme digestion site was added to the primer terminal.

In the non-autonomous Tol2 transposon nucleotide sequence (SEQ ID NO:1) disclosed by JP-A-2003-235575, a nucleotide sequence at positions 1 to 200 (Tol2-L sequence) (SEQ ID NO:2) and a nucleotide sequence at positions 2285 to 2788 (Tol2-R sequence) (SEQ ID NO:3) were used as the transposon sequences.

A DNA fragment comprising either of the Tol2-R sequence and Tol2-L sequence was synthesized.

A DNA fragment including a nucleotide sequence (SEQ ID NO:18) which encodes antibody H chain under control of CMV promoter, amplified based on the anti-human CD98 antibody N5KG1-Val C2IgG1NS/I117L vector (Japanese Patent No. 4324637), was prepared as the antibody heavy chain gene cassette, and a DNA fragment comprising a nucleotide sequence (SEQ ID NO:21) which encoded antibody light chain under control of SV40 promoter, amplified based on the anti-human CD98 antibody N5KG1-Val C2IgG1NS/I117L vector, as the antibody light chain gene cassette.

As the neomycin resistance gene cassette, a DNA fragment comprising a DNA which comprises a nucleotide sequence encoding a neomycin resistance gene under control of SV40 promoter (a DNA which encodes a neomycin phosphotransferase consisting of the nucleotide sequence represented by SEQ ID NO:36 and GenBank Accession No. U47120.2) was prepared.

Figure 13:
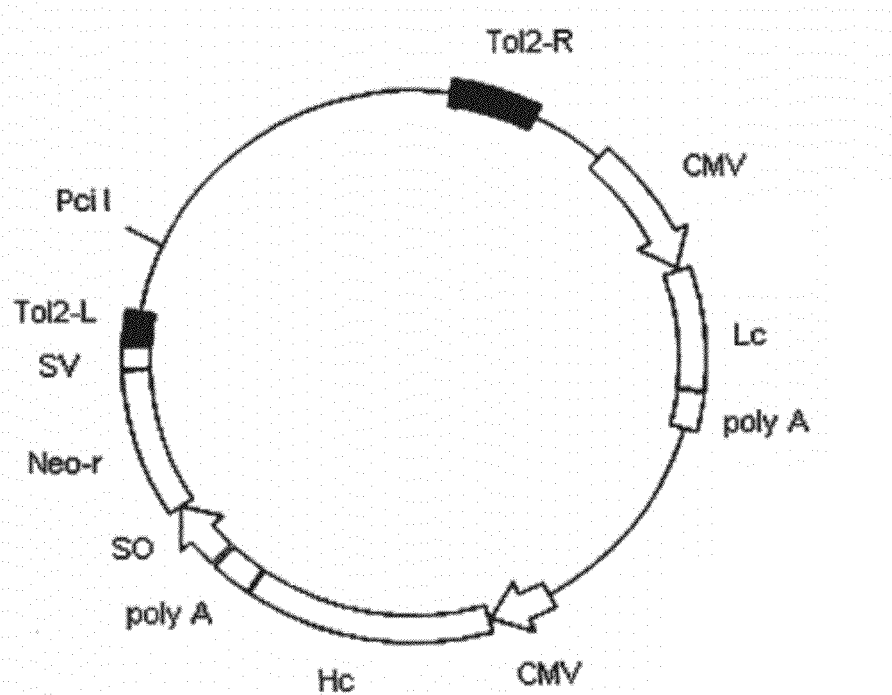
FIG. 13 shows structure of the antibody expression vector A.

An anti-CD98 antibody expression vector A was prepared by connecting the above-mentioned antibody heavy chain gene expression cassette, antibody light chain gene expression cassette and neomycin resistance gene expression cassette and further connecting its both terminals with a DNA fragment comprising a Tol2-R sequence and a DNA fragment comprising a Tol2-L sequence (FIG. 13).

(2) Preparation of Anti-Human CD98 Antibody Expression Transposon Vector Comprising a Modified Type Neomycin Resistance Gene 1

An anti-human CD98 antibody expression transposon vector B in which the neomycin resistance gene of the anti-human CD98 antibody expression transposon vector A obtained in (1) which comprises a wild type neomycin resistance gene was replaced by a modified type neomycin resistance gene 1 comprising the nucleotide sequence represented by SEQ ID NO:37 was prepared.

The modified type neomycin resistance gene 1 encodes an amino acid sequence identical to that of the wild type neomycin resistance gene and was modified to have a nucleotide sequence in which 167 bases corresponding to 22% of the entire were modified. Specifically, among the total of 32 leucine residues, codons corresponding to 25 leucine residues were modified so as to be TTA.

(3) Preparation of Anti-Human CD98 Antibody Expression Transposon Vector Comprising a Modified Type Neomycin Resistance Gene 2

An anti-human CD98 antibody expression transposon vector C in which the neomycin resistance gene of the anti-human CD98 antibody expression transposon vector A obtained in (1) which comprises a wild type neomycin resistance gene was replaced by a modified type neomycin resistance gene 2 comprising the nucleotide sequence represented by SEQ ID NO:38 was prepared.

The modified type neomycin resistance gene 2 encoded the amino acid sequence identical to that of the wild type neomycin resistance gene and had a nucleotide sequence in which the 180 bases corresponding to 23% of the entire were modified. Specifically, among the total of 32 leucine residues, codons corresponding to 28 leucine residues were modified so as to be TTA.

(4) Preparation of Anti-Human CD98 Antibody Expression Transposon Vector Having a Modified Type Neomycin Resistance Gene 3

An anti-human CD98 antibody expression transposon vector D in which the neomycin resistance gene of the anti-human CD98 antibody expression transposon vector A obtained in (1) which comprises a wild type neomycin resistance gene was replaced by a modified type neomycin resistance gene 3 comprising the nucleotide sequence represented by SEQ ID NO:39 was prepared.

The modified type neomycin resistance gene 3 encoded the amino acid sequence identical to that of the wild type neomycin resistance gene and had a nucleotide sequence in which 203 bases corresponding to 26% of the entire were modified. Specifically, among the total of 32 leucine residues, codons corresponding to 30 leucine residues were modified so as to be TTA.

Example 10

Antibody Production by Antibody Producer CHO Cells which Expresses Modified Type Neomycin Resistance Gene Antibody producing cells A to D were prepared by introducing each of the anti-human CD98 expression transposon vectors A to D prepared in Example 9(1) to (4) into the suspension CHO-K1 cell together with a vector pCAGGS-T2TP which expresses a Tol2 transposase comprising the amino acid sequence represented by SEQ ID NO:40 [Kwakami K. & Noda T., *Genetics*, 166, 895-899 (2004)].

Introduction of vectors into the suspension CHO cell was carried out by suspending the CHO cell ($4\times10^6$ cells) in 400 µl of PBS buffer and co-transfecting the anti-human CD98 antibody expression transposon vector (10 μg) and Tol2 transposase expression vector pCAGGS-T2TP (20 μg) directly in the form of circular DNA by electroporation.

In this case, the Tol2 transposase expression vector was also introduced directly as circular DNA in order to transiently express Tol2 transposase.

In addition, as a control which did not use Tol2 transposase, the anti-human CD98 antibody expression transposon vector D (10 μg) of Example 19(4) was linearlized using a restriction enzyme PciI (TARA BIO INC.) and then introduced into suspension CHO-K1 cell by electroporation.

The electroporation was carried out using an electroporator [Gene Pulser Xcell system (manufactured by Bio-Rad)] under conditions of voltage of 300 V, electrostatic capacity of 500 μF and room temperature and using a cuvette of 4 mm in gap width (manufactured by Bio-Rad).

After the gene introduction by electroporation, the cells in each cuvette were inoculated onto one 96-well plate and cultured for 3 days in a $CO_2$ incubator using a CD OptiCHO medium (Invitrogen) supplemented with 5% soybean hydrolyzate.

Next, from the medium exchange after 4 days of the gene introduction, culturing was carried out in the presence of G418 (Geneticin®, Invitrogen) by adding the G418 to give a final concentration of 500 μg/ml, and the culturing was carried out for 3 weeks while changing the medium at intervals of one week.

After the culturing, expression of the antibody was determined using LANCE® assay (Perkin-Elmer Corp) by a sandwich method to which FRET (fluorescence resonance energy introduction) was applied. The results are shown in Table 9.

TABLE 9

|  | Antibody producing cells | | | | |
| --- | --- | --- | --- | --- | --- |
|  | A (Wild Type) | B (Modified Type 1) | C (Modified Type 2) | D (Modified Type 3) | Control cell |
| Antibody expression level (mg/L) of cells showing maximum expression | 0.5 | 2.0 | 1.6 | 5.1 | — |
| Average antibody expression level (mg/L) of top 10 cells | 0.5 | 0.7 | 0.7 | 1.7 | — |

As shown in Table 9, expression levels of anti-human CD98 antibody of the cells B to D expressing the modified type neomycin resistance genes were higher than that of the cell A which expressed the wild type neomycin resistance gene.

Particularly, in the case of the anti-human CD98 antibody producing cell D which expresses the modified type neomycin resistance gene 3, the cell line showing the times higher expression level than that of the anti-human CD98 antibody producing cell A which expresses the wild type neomycin resistance gene was obtained.

In addition, even when the modified type neomycin resistance gene 3 was used, it was not able to obtain a cell which expresses the anti-human CD98 antibody by the control cell into which the Tol2 transposase expression vector was not co-transfected in spite of making the vector into linear form.

Example 11

Preparation of Transposon Vector Expressing Puromycin Resistance Gene and Anti-Human CD98 Antibody (1) Preparation of Anti-Human CD98 Antibody Expression Transposon Vector Comprising Modified Type Puromycin Resistance Gene 1

An anti-human CD98 antibody expression transposon vector E in which the neomycin resistance gene of the anti-human CD98 antibody expression transposon vector A obtained in Example 9(1) which comprised wild type neomycin resistance gene, was replaced by a modified type puromycin resistance gene 1 consisting of the nucleotide sequence represented by SEQ ID NO:41 was prepared.

The modified type puromycin resistance gene 1 encoded an amino acid sequence identical to that of the wild type puromycin resistance gene consisting of the nucleotide sequence represented by SEQ ID NO:42 (a puromycin-N-acetyltransferase gene, consists of the nucleotide sequence disclosed in GenBank Accession No. U07648.1) and had a nucleotide sequence in which 17 bases corresponding to the 3% of the entire bases are modified. Specifically, among the total of 28 alanine residues contained in the puromycin resistance gene, codons corresponding to 17 alanine residues were changed to GCG by the modification and, together with the codons which were already GCG in the wild type, the codons which correspond to all of the alanine residues were changed to GCG.

(2) Preparation of Anti-Human CD98 Antibody Expression Transposon Vector Comprising Modified Type Puromycin Resistance Gene 2

An anti-human CD98 antibody expression transposon vector F in which the neomycin resistance gene of the anti-human CD98 antibody expression transposon vector A obtained in Example 9(1) which comprises wild type neomycin resistance gene was replaced by a modified type puromycin resistance gene 2 comprising the nucleotide sequence represented by SEQ ID NO:43 was prepared. The modified type puromycin resistance gene 2 encodes an amino acid sequence identical to that of the wild type puromycin resistance gene and had a nucleotide sequence in which 79 bases corresponding to the 14% of the entire bases are modified. Specifically, in addition to the modification of codons which correspond to the alanine residues of the modified type puromycin resistance gene 1, the codons corresponding to leucine residues were changed so as to be TTA, and the codons corresponding to valine residues were changed so as to be GTA and the codon of serine were changed so as to be TCG.

Example 12

Antibody Production by Antibody Producing CHO Cell which Expresses Modified Type Puromycin Resistance Gene 1

Antibody producing cells E and F were prepared by introducing the anti-human CD98 antibody expression transposon vector E of Example 11(1) comprising the modified type puromycin resistance gene 1, the anti-human CD98 antibody expression transposon vector F of Example 11(2) comprising the modified type puromycin resistance gene 2 and the Tol2 transposase expression vector pCAGGS-T2TP into the suspension CHO-K1 cell.

Introduction of the vectors into suspension cell was carried out by suspending the suspension CHO cell ($4 \times 10^6$ cells) in 400 µl of PBS buffer and co-transfecting the anti-human CD98 antibody expression transposon vector comprising the modified type puromycin resistance gene in the form of circular DNA (10 µg) and the pCAGGS-T2TP (20 µg) directly by electroporation.

In this case, the Tol2 transposase expression vector pCAGGS-T2TP was also introduced directly in the form of circular DNA in order to transiently express Tol2 transposase.

The electroporation was carried out using an electroporator [Gene Pulser Xcell system (manufactured by Bio-Rad)] under conditions of voltage of 300 V, electrostatic capacity of 500 µF and room temperature and using a cuvette of 4 mm in gap width (manufactured by Bio-Rad).

After the gene introduction by electroporation, the cells in each cuvette were inoculated onto one 96-well plate and cultured for 3 days in a $CO_2$ incubator using a CD OptiCHO medium (Invitrogen) supplemented with 5% soybean hydrolyzate.

Next, from the medium exchange after 2 days of the gene introduction, culturing was carried out for 4 weeks while adding puromycin (P9620, Sigma-Aldrich) to give a final concentration of 5 µg/ml and carrying out the medium exchange to the puromycin-containing medium at intervals of one week.

After the culturing, expression level of the antibody was determined using LANCE® assay (Perkin-Elmer Corp) by a sandwich method to which FRET (fluorescence resonance energy transfer) was applied. The results are shown in Table 2.

TABLE 10

| | Antibody producing cells | |
|---|---|---|
| | E (Modification 1) | F (Modification 2) |
| Antibody expression level (mg/L) of cells showing maximum expression | 1.0 | 2.2 |
| Average antibody expression level (mg/L) of top 10 cells | 0.7 | 1.6 |

As shown in Table 10, the antibody producing cell F which expresses the modified type puromycin resistance gene 2 showed two times or more antibody productivity of the antibody producing cell E which expresses the modified type puromycin resistance gene 1.

Example 13

Antibody Production by Antibody Producing CHO Cell which Expresses Modified Type Puromycin Resistance Gene 2

The antibody producing cell F obtained in Example 12 which expresses the modified type puromycin resistance gene 2 was cultured using a conical flask to produce anti-human CD98 antibody.

Specifically, the antibody producing cell F was expansion-cultured using 96-well plate, 24-well plate and 6-well plate in that order. Two cell lines of the antibody producing cell F in which the number of cell was sufficiently increased (cell line 1 and cell line 2) were selected, and respectively suspended in 35 ml of the CD OptiCHO medium (Invitrogen) supplemented with 5% soybean hydrolyzate so as to give a cell density of $2 \times 10^5$ cells/ml and cultured for 1 week on a shaker using a 125 ml capacity of conical flask (with a bent cap, Corning Glassworks) in an atmosphere of 37° C. and 5% $CO_2$, thereby producing the anti-human CD98 antibody.

Amount of the antibody in the medium after culturing was determined by HPLC (Waters Associates, Inc.). The results are shown in Table 11.

TABLE 11

| | Cell line 1 | Cell line 2 |
|---|---|---|
| Antibody expression level (mg/l) | 15.6 | 14.8 |

The above results show that in the suspension CHO cell, the antibody gene inserted between a pair of transposon sequences and the modified type drug resistance gene are introduced efficiently into the host chromosome and also are effective for the selection of a high expression cell. In addition, it was found that the thus obtained cell can be expansion-cultured and production of the protein of interest under a suspension culturing condition is possible.

While the invention has been described in detail and with reference to specific embodiments thereof, it will be apparent to one skill in the art that various changes and modifications can be made therein without departing from the spirit and scope thereof.

This application is based on Japanese application No. 2010-279849, filed on Dec. 15, 2010, the entire contents of which are incorporated hereinto by reference. All references cited herein are incorporated in their entirety.

[Sequence Listing]
SEQ ID NO:1—Description of Artificial sequence; Nucleotide Sequence of Non-autonomous Tol2 Transposon
SEQ ID NO:2—Description of Artificial sequence; Tol2-L sequence
SEQ ID NO:3—Description of Artificial sequence; Tol2-R sequence
SEQ ID NO:7—Description of Artificial sequence; Nucleotide Sequence of Cycloheximide Resistance Gene
SEQ ID NO:8—Description of Artificial sequence; Amino Acid Sequence of Protein encoding Cycloheximide Resistance Gene
SEQ ID NO:9—Description of Artificial sequence; Nucleotide Sequence encoding M2Z3 Antibody H chain
SEQ ID NO:10—Description of Artificial sequence; Amino Acid Sequence of M2Z3 Antibody H chain
SEQ ID NO:11—Description of Artificial sequence; Nucleotide Sequence encoding M2Z3 Antibody L chain
SEQ ID NO:12—Description of Artificial sequence; Amino Acid Sequence of M2Z3 Antibody L chain
SEQ ID NO:13—Description of Artificial sequence; Nucleotide Sequence of Non-autonomous Tol1
SEQ ID NO:14—Description of Artificial sequence; Tol1-L sequence
SEQ ID NO:15—Description of Artificial sequence; Tol1-R sequence
SEQ ID NO:18—Description of Artificial sequence; Nucleotide Sequence encoding Anti-CD98 Antibody Heavy Chain Variable Region
SEQ ID NO:19—Description of Artificial sequence; Amino Acid Sequence of Anti-CD98 Antibody Heavy Chain Variable Region
SEQ ID NO:20—Description of Artificial sequence; Amino Acid Sequence of Anti-CD98 Antibody Heavy Chain Variable Region SEQ ID NO:21—Description of Artificial sequence; Nucleotide Sequence encoding Anti-CD98 Antibody Light Chain Variable Region
SEQ ID NO:22—Description of Artificial sequence; Amino Acid Sequence of Anti-CD98 Antibody Light Chain Variable Region
SEQ ID NO:23—Description of Artificial sequence; Amino Acid Sequence of Anti-CD98 Antibody Light Chain Variable Region
SEQ ID NO:24—Description of Artificial sequence; Nucleotide Sequence encoding Anti-human TNFα Antibody Heavy Chain Variable Region
SEQ ID NO:25—Description of Artificial sequence; Amino Acid Sequence of Anti-human TNFα Antibody Heavy Chain Variable Region
SEQ ID NO:26—Description of Artificial sequence; Amino Acid Sequence of Anti-human TNFα Antibody Heavy Chain Variable Region
SEQ ID NO:27—Description of Artificial sequence; Nucleotide Sequence encoding Anti-human TNFα Antibody Light Chain Variable Region
SEQ ID NO:28—Description of Artificial sequence; Amino Acid Sequence of Anti-human TNFα Antibody Light Chain Variable Region
SEQ ID NO:29—Description of Artificial sequence; Amino Acid Sequence of Anti-human TNFα Antibody Light Chain Variable Region
SEQ ID NO:30—Description of Artificial sequence; Nucleotide Sequence encoding Anti-human CD20 Antibody Heavy Chain Variable Region
SEQ ID NO:31—Description of Artificial sequence; Amino Acid Sequence of Anti-human CD20 Antibody Heavy Chain Variable Region
SEQ ID NO:32—Description of Artificial sequence; Amino Acid Sequence of Anti-human CD20 Antibody Heavy Chain Variable Region
SEQ ID NO:33—Description of Artificial sequence; Nucleotide Sequence encoding Anti-human CD20 Antibody Light Chain Variable Region
SEQ ID NO:34—Description of Artificial sequence; Amino Acid Sequence of Anti-human CD20 Antibody Light Chain Variable Region
SEQ ID NO:35—Description of Artificial sequence; Amino Acid Sequence of Anti-human CD20 Antibody Light Chain Variable Region
SEQ ID NO:36—Description of Artificial sequence; Nucleotide Sequence of Wild Type of Neomycin Resistance Gene
SEQ ID NO:37—Description of Artificial sequence; Nucleotide Sequence of Modified Type of Neomycin Resistance Gene
SEQ ID NO:38—Description of Artificial sequence; Nucleotide Sequence of Modified Type of Neomycin Resistance Gene
SEQ ID NO:39—Description of Artificial sequence; Nucleotide Sequence of Modified Type of Neomycin Resistance Gene
SEQ ID NO:41—Description of Artificial sequence; Nucleotide Sequence of Modified Type of Puromycin Resistance Gene
SEQ ID NO:42—Description of Artificial sequence; Nucleotide Sequence of Wild Type of Puromycin Resistance Gene
SEQ ID NO:43—Description of Artificial sequence; Nucleotide Sequence of Modified Type of Puromycin Resistance Gene
SEQ ID NO:44—Description of Artificial sequence; Nucleotide Sequence of Modified Type of Puromycin Resistance Gene
SEQ ID NO:45—Description of Artificial sequence; Nucleotide Sequence of Modified type of Zeocin resistance gene
SEQ ID NO:46—Description of Artificial sequence; Nucleotide Sequence of Modified type of Zeocin resistance gene
SEQ ID NO:47—Description of Artificial sequence; Nucleotide Sequence of Modified type of Hygromycin resistance gene
SEQ ID NO:48—Description of Artificial sequence; Nucleotide Sequence of Modified type of Hygromycin resistance gene

What is claimed is:

1. A method selected from the group consisting of (1)-(3):

(1) a method for producing a protein of interest, comprising introducing at least one expression vector which comprises a gene fragment containing a DNA sequence encoding the protein of interest, and which also comprises a pair of transposon sequences derived from a pair of Tol1 transposons or from a pair of Tol2 transposons at both terminals of the gene fragment, into a suspension mammalian cell capable of surviving and proliferating in a serum-free medium; integrating the gene fragment inserted between the pair of transposon sequences into a chromosome of the mammalian cell to obtain a mammalian cell which expresses the protein of interest; and suspension-culturing the mammalian cell;

(2) a method for producing a protein of interest, comprising the following steps (A) to (C):

(A) a step of simultaneously introducing the following expression vectors (a) and (b) into a suspension mammalian cell capable of surviving and proliferating in a serum-free medium:

(a) at least one expression vector which comprises a gene fragment containing a DNA sequence encoding a protein of interest, and which also comprises a pair of transposon sequences derived from a pair of Tol1 transposons or from a pair of Tol2 transposons at both terminals of the gene fragment, (b) an expression vector which comprises a DNA encoding a transposase which recognizes the transposon sequences and has an activity of transferring a gene fragment inserted between a pair of the transposon sequences into a chromosome, (B) a step of obtaining a suspension mammalian cell which expresses the protein of interest by expressing transiently the transposase from the expression vector which is introduced into the suspension mammalian cell in step (A), to integrate the gene fragment inserted between the pair of transposon sequences into a chromosome of the mammalian cell, and (C) a step of suspension-culturing the suspension mammalian cell which expresses the protein of interest obtained in step (B) to produce the protein of interest; and (3) a method for obtaining a suspension mammalian cell which expresses a protein of interest, comprising introducing, into a suspension mammalian cell capable of surviving and proliferating in a serum-free medium, at least one expression vector which comprises a gene fragment containing a DNA sequence encoding the protein of interest, and which also comprises transposon sequences derived from a pair of Tol1 transposons or from a pair of Tol2 transposons at both terminals of the gene fragment; and integrating the gene fragment inserted between the pair of transposon sequences into a chromosome of the mammalian cell, wherein the suspension mammalian cell is Chinese hamster ovary (CHO) cell, wherein the DNA encoding the protein of interest is a DNA encoding an antibody, wherein the nucleotide sequences derived from a pair of Tol2 transposons are a nucleotide sequence comprising the nucleotide sequence of SEQ ID NO:2 and the nucleotide sequence of SEQ ID NO:3, and wherein the nucleotide sequences derived from a pair of Tol1 transposons are the nucleotide sequences of SEQ ID NO: 14 and the nucleotide sequence of SEQ ID NO: 15.

2. The method according to claim 1, wherein at least one of said expression vectors which comprises a gene fragment containing a DNA sequence encoding the protein of interest also comprises a selectable marker gene within said gene fragment.

3. The method according to claim 1, wherein in addition to introducing into the suspension mammalian cell the at least one expression vector comprising a gene fragment containing a DNA sequence encoding a protein of interest, an expression vector which comprises a gene fragment containing a selectable marker gene, and which also comprises a pair of transposon sequences derived from a pair of Tol1 transposons or from a pair of Tol2 transposons at both terminals of the gene fragment, is introduced into the suspension mammalian cell.

4. The method according to claim 1, wherein the DNA encoding an antibody is at least one of a DNA encoding a H chain of the antibody and a DNA encoding a L chain of the antibody.

5. The method according to claim 2, wherein in said method, a vector(s) selected from the group consisting of (a) to (d) is introduced into a suspension mammalian cell:

(a) an expression vector which comprises a gene fragment containing a DNA sequence encoding a H chain of an antibody, and which also comprises a pair of transposon sequences derived from a pair of Tol1 transposons or from a pair of Tol2 transposons at both terminals of the gene fragment; an expression vector which comprises a gene fragment containing a DNA sequence encoding a L chain of an antibody, and which also comprises a pair of transposon sequences derived from a pair of Tol1 transposons or from a pair of Tol2 transposons at both terminals of the gene fragment and an expression vector which comprises a gene fragment containing a selectable marker gene, and which also comprises a pair of transposon sequences derived from a pair of Tol1 transposons or from a pair of Tol2 transposons at both terminals of the gene fragment, (b) an expression vector which comprises a gene fragment containing a DNA sequence encoding a H chain of an antibody and a selectable marker gene, and which also comprises a pair of transposon sequences derived from a pair of Tol1 transposons or from a pair of Tol2 transposons at both terminals of the gene fragment and an expression vector which comprises a gene fragment containing a DNA sequence encoding a L chain of an antibody, and which also comprises a pair of transposon sequences derived from a pair of Tol1 transposons or from a pair of Tol2 transposons at both terminals of the gene fragment, (c) an expression vector which comprises a gene fragment containing a DNA sequence encoding a L chain of an antibody and a selectable marker gene, and which also comprises a pair of transposon sequences derived from a pair of Tol1 transposons or from a pair of Tol2 transposons at both terminals of the gene fragment and an expression vector which comprises a gene fragment containing a DNA sequence encoding a H chain of an antibody, and which also comprises a pair of transposon sequences derived from a pair of Tol1 transposons or from a pair of Tol2 transposons at both terminals of the gene fragment, and (d) an expression vector which comprises a gene fragment containing a DNA sequence encoding a H chain and a L chain of an antibody and a selectable marker gene, and which also comprises a pair of transposon sequences derived from a pair of Tol1 transposons or from a pair of Tol2 transposons at both terminals of the gene fragment.

6. The method according to claim 2, wherein the selectable marker gene is a cycloheximide resistance gene.

7. The method according to claim 6, wherein the cycloheximide resistance gene is a ribosome protein.

8. A suspension mammalian cell, which produces a protein of interest, wherein said suspension mammalian cell is obtained by the following steps (A) and (B):

(A) a step of simultaneously introducing the following expression vectors (a) and (b) into a suspension mammalian cell capable of surviving and proliferating in a serum-free medium:

(a) at least one expression vector which comprises a gene fragment containing a DNA sequence encoding a protein of interest, and which also comprises a pair of transposon sequences derived from a pair of Tol1 transposons or from a pair of Tol2 transposons at both terminals of the gene fragment, (b) an expression vector which comprises a DNA encoding a transposase which recognizes the transposon sequences and has an activity of transferring a gene fragment inserted between a pair of the transposon sequences into a chromosome, (B) a step of obtaining the suspension mammalian cell which expresses the protein of interest by expressing transiently the transposase from the expression vector which is introduced into the suspension mammalian cell in step (A), to integrate the gene fragment inserted between the pair of transposon sequences into a chromosome of the mammalian cell, wherein the suspension mammalian cell is Chinese hamster ovary (CHO) cell, wherein the DNA encoding the protein of interest is a DNA encoding an antibody, wherein the nucleotide sequences derived from a pair of Tol2 transposons are a nucleotide sequence comprising the nucleotide sequence of SEQ ID NO:2 and the nucleotide sequence of SEQ ID NO:3, and wherein the nucleotide sequences derived from a pair of Tol1 transposons are the nucleotide sequences of SEQ ID NO: 14 and the nucleotide sequence of SEQ ID NO: 15.

9. The expression vector according to claim 1 or 8, wherein said expression vector comprises a gene fragment containing a DNA sequence encoding an antibody and a pair of transposon sequences derived from a pair of TOl1 transposons or from a pair of Tol2 transposons at both terminals of the gene fragment.

* * * * *